US008962912B2

(12) United States Patent
Sasgary et al.

(10) Patent No.: US 8,962,912 B2
(45) Date of Patent: Feb. 24, 2015

(54) TRANSGENIC NON-HUMAN ANIMALS EXPRESSING HUMAN BLOOD CLOTTING FACTORS AND USES THEREOF

(75) Inventors: Maria Sasgary, Vienna (AT); Maria Schuster, Vienna (AT); Hans-Peter Schwarz, Vienna (AT); Birgit Maria Reipert, Vienna (AT); Gerhard Antoine, Vienna (AT); Hartmut Ehrlich, Vienna (AT)

(73) Assignees: Baxter International Inc., Deerfield, IL (US); Baxter Healthcare SA, Glattpark (Opfikon) (CH)

(*) Notice: Subject to any disclaimer, the term of this patent is extended or adjusted under 35 U.S.C. 154(b) by 0 days.

(21) Appl. No.: 13/071,190

(22) Filed: Mar. 24, 2011

(65) Prior Publication Data
US 2012/0082987 A1    Apr. 5, 2012

Related U.S. Application Data

(62) Division of application No. 12/346,432, filed on Dec. 30, 2008, now abandoned.

(60) Provisional application No. 61/017,920, filed on Dec. 31, 2007.

(51) Int. Cl.
| A01K 67/027 | (2006.01) |
| G01N 33/00 | (2006.01) |
| C12N 15/00 | (2006.01) |
| C12N 15/85 | (2006.01) |
| C07K 14/745 | (2006.01) |
| C07K 14/755 | (2006.01) |
| C12N 9/64 | (2006.01) |

(52) U.S. Cl.
CPC ........ *C12N 15/8509* (2013.01); *A01K 67/0275* (2013.01); *C07K 14/745* (2013.01); *C07K 14/755* (2013.01); *C12N 9/64* (2013.01); *A01K 2207/15* (2013.01); *A01K 2217/00* (2013.01); *A01K 2217/15* (2013.01); *A01K 2227/105* (2013.01); *A01K 2267/02* (2013.01); *A01K 2267/03* (2013.01)
USPC ......... 800/18; 800/3; 800/21; 800/25; 800/22

(58) Field of Classification Search
USPC .......................................................... 800/20
See application file for complete search history.

(56) References Cited

U.S. PATENT DOCUMENTS

| 4,736,866 A | 4/1988 | Leder et al. |
| 4,757,006 A | 7/1988 | Toole, Jr. et al. |
| 4,873,191 A | 10/1989 | Wagner et al. |
| 5,446,143 A | 8/1995 | Simpson et al. |
| 5,470,560 A | 11/1995 | Martin, Jr. |
| 5,650,503 A | 7/1997 | Archibald et al. |
| 5,670,134 A | 9/1997 | Martin, Jr. |
| 5,880,327 A | 3/1999 | Lubon et al. |
| 6,130,203 A | 10/2000 | Voorberg |
| 6,156,888 A | 12/2000 | Voorberg |
| 6,316,226 B1 | 11/2001 | Van Ooyen et al. |
| 6,346,513 B1 | 2/2002 | Van Ooyen et al. |
| 6,492,575 B1 | 12/2002 | Wagner et al. |
| 6,958,322 B1 | 10/2005 | Himmelspach et al. |
| 7,294,755 B1 | 11/2007 | Readhead et al. |
| 2005/0229261 A1 | 10/2005 | Cheng et al. |
| 2006/0160948 A1 | 7/2006 | Scheiflinger et al. |
| 2007/0011752 A1 | 1/2007 | Paleyanda |
| 2009/0226893 A1 | 9/2009 | Baker |

FOREIGN PATENT DOCUMENTS

| EP | 1739170 A2 | 1/2007 |
| WO | WO-93/20242 | 10/1993 |
| WO | WO-95/16918 | 6/1995 |
| WO | WO-95/30642 | 11/1995 |
| WO | WO-02/072023 A2 | 9/2002 |
| WO | WO-02/077161 A2 | 10/2002 |
| WO | WO-2005/056769 | 6/2005 |
| WO | WO-2006/056769 | 6/2006 |

OTHER PUBLICATIONS

Gorman Curr Opin Biotechnol. Oct. 1990;1(1):36-47.*
Godwin et al , PNAS, 1998, 95:13042-47.*
Niemann et al (Rev. Sci, Tech. Off. Int. Spiz. 2005, (24), 285-298.*
Clark et al , Nature Reviews: Genetics. 2003, 825-833.*
Wheeler Theriogenology. 2001, (56), 1345-1369.*
Prelle, Anat. Histol. Embryol. 2002, vol. 31, 169-186.*
Smith Journal of Biotechnology, 99:1-22, 2002.*
Reipert Thromb Haemost, 2000,84:826-832.*
Cao et al. J. of Exp. Zoo., 311A: 368-376, 2009.*
Paris et al. Theriogenology, 74: 516-524, 2010.*
"Complete sequence and gene map of a human major histocompatibility complex. The MHC sequencing consortium", *Nature*, 401:921-3 (1999).
Alexander et al., "Circulating human factor IX produced in keratin-promoter transgenic mice: a feasibility study for gene therapy of haemophilia B", *Hum. Mol. Genet.*, 4:993-9 (1995).
Alvarado et al., "Acquired hemophilia: a case report of 2 patients with acquired factor VIII inhibitor treated with rituximab plus a short course of steroid and review of the literature", *Clin. Appl. Thromb. Hemost.*, 13:443-8 (2007).
Ao et al., "Fluoroimmunoassay for antigen based on fluorescence quenching signal of gold nanoparticles", *Anal. Chem.*, 78:1104-6 (2006).
Baribault et al., "Embryonic stem cell culture and gene targeting in transgenic mice", *Mol. Biol. Med.*, 6:481-92 (1989).
Bauer, "Treatment of factor VII deficiency with recombinant factor VIIa", *Haemostasis*, 26 Suppl 1:155-8 (1996).

(Continued)

*Primary Examiner* — Valarie Bertoglio
(74) *Attorney, Agent, or Firm* — Marshall, Gerstein & Borun LLP

(57) ABSTRACT

The present invention relates, in general, to development of non-human transgenic animals expressing a human blood clotting factor, such as Factor VIII, Factor VII, Factor IX and von Willebrand factor. The invention further provides methods of detecting immunogenic events against human blood clotting factor using the transgenic animals described.

11 Claims, 9 Drawing Sheets

(56) References Cited

OTHER PUBLICATIONS

Bigger et al., "Permanent partial phenotypic correction and tolerance in a mouse model of hemophilia B by stem cell gene delivery of human factor IX", *Gene Ther.*, 13:117-26 (2006).
Bodine et al., "Combination of interleukins 3 and 6 preserves stem cell function in culture and enhances retrovirus-mediated gene transfer into hematopoietic stem cells", *Proc. Natl. Acad. Sci. USA*, 86:8897-901 (1989).
Bouvry et al., Acquired hemophilia. *Haematologica*, 79: 550-6 (1994).
Bril et al., Tolerance to factor VIII in a transgenic mouse expressing human factor VIII cDNA carrying an Arg(593) to Cys substitution. *Thromb. Haemost*, 95: 341-7 (2006).
Brinster et al., "Regulation of metallothionein—thymidine kinase fusion plasmids injected into mouse eggs", *Nature*, 296:39-42 (1982).
Capecchi, "The new mouse genetics: altering the genome by gene targeting", *Trends Genet*, 5:70-6 (1989).
Chen et al., "A gold nanoparticles/sol-gel composite architecture for encapsulation of immunoconjugate for reagentless electrochemical immunoassay", *Biomaterials*, 27:2313-21 (2006).
Cheng et al., "Characterization of HLA DR2 and DQ8 transgenic mouse with a new engineered mouse class II deletion, which lacks all endogenous class II genes", *J. Autoimmun.*, 21:195-9 (2003).
Collins, "Novel therapies for immune tolerance in haemophilia A", *Haemophilia*, 12 Suppl 6:94-100 (2006).
Cui et al., "Synthesis of AgcoreAushell bimetallic nanoparticles for immunoassay based on surface-enhanced Raman spectroscopy", *J. Phys. Chem. B*, 110:4002-6 (2006).
Dai et al., "Electrochemical sensor for immunoassay of carcinoembryonic antigen based on thionine monolayer modified gold electrode", *Cancer Detect Prev.*, 29:233-40 (2005).
Denis et al., "A mouse model of severe von Willebrand disease: defects in hemostasis and thrombosis", *Proc. Natl. Acad. Sci. USA*, 95:9524-9 (1998).
Diaz et al., "Exchange of viral promoter/enhancer elements with heterologous regulatory sequences generates targeted hybrid long terminal repeat vectors for gene therapy of melanoma", *J. Virol.*, 72:789-95 (1998).
DiMichele, "Acquired hemophilia: a case report of 2 patients with acquired factor VIII inhibitor treated with rituximab plus a short course of steroid and review of the literature", *Br. J. Haematol.*, 138:305-15 (2007).
Doetschman et al., "Targetted correction of a mutant HPRT gene in mouse embryonic stem cells", *Nature*, 330:576-8 (1987).
Eglitis et al., "Retroviral-mediated gene transfer into hemopoietic cells", *Adv. Exp. Med. Biol.*, 241:19-27 (1988).
Escobar et al., "Induction in transgenic mice of HLA-A2.1-restricted cytotoxic T cells specific for a peptide sequence from a mutated p21ras protein", *Clin. Exp. Immunol.*, 116:214-9 (1999).
Franchini et al., "Drug-induced anti-factor VIII antibodies: a systematic review", *Med. Sci. Monit.*, 13:RA55-61 (2007).
Franchini et al., Acquired factor VIII inhibitors. *Blood*, 112: 119-25 (2006).
Franchini et al., The use of recombinant activated factor VII in congenital and acquired von Villebrand disease. *Blood Coagul. Fibrinolysis*, 17: 516-9 (2006).
Franchini, "Acquired hemophilia A", *Hematology*, 11:119-25 (2006).
Fugger et al., "Expression of HLA-DR4 and human CD4 transgenes in mice determines the variable region beta-chain T-cell repertoire and mediates an HLA-DR-restricted immune response", *Proc. Natl. Acad. Sci. USA*, 91:6151-5 (1994).
GenBank accession No. NM_000131, *Homo sapiens* coagulation factor VII (serum prothrombin conversion accelerator) (F7), transcript variant 1, mRNA, Mar. 22, 2009.
GenBank accession No. NM_000552, *Homo sapiens* von Willebrand factor (VWF), mRNA, Mar. 22, 2009.

GenBank accession No. NP_000119, platelet coagulation factor XI precursor [*Homo sapiens*], Jan. 25, 2009.
GenBank accession No. NP_000120, coagulation factor XIII A1 subunit precursor [*Homo sapiens*], Jan. 25, 2009.
GenBank accession No. NP_000121, coagulation factor V precursor [*Homo sapiens*], Mar. 1, 2009.
GenBank accession No. NP_000303, protein C (inactivator of coagulation factors Va and VIIIa) [*Homo sapiens*], Mar. 1, 2009.
GenBank accession No. NP_000479, serpin peptidase inhibitor, Glade C, member 1 [*Homo sapiens*], Feb. 21, 2009.
GenBank accession No. NP_000496, coagulation factor XII precursor [*Homo sapiens*], Feb. 15, 2009.
GenBank accession No. NP_000497, coagulation factor II preproprotein [*Homo sapiens*], Mar. 1, 2009.
GenBank accession No. NP_001985, coagulation factor XIII B subunit precursor [*Homo sapiens*], Feb. 1, 2009.
Ghindilis, "Direct electron transfer catalysed by enzymes: application for biosensor development", *Biochem. Soc. Trans.*, 28:84-9 (2000).
Gilboa, "Retroviral gene transfer: applications to human therapy", *Adv. Exp. Med. Biol.*, 241 :29-33 (1988).
Gilles et al., "Anti-factor VIII antibodies of hemophiliac patients are frequently directed towards nonfunctional determinants and do not exhibit isotypic restriction", *Blood*, 82:2452-61 (1993).
Gordon, "Transgenic animals", *Int. Rev. Cytol.*, 115:171-229 (1989).
Gorman, Mammalian cell expression. *Curr. Opin. Biotechnol.*, 1(1): 36-47 (1990).
Hallet et al., "Transposition and site-specific recombination: adapting DNA cut-and-paste mechanisms to a variety of genetic rearrangements", *FEMS Microbiol. Rev.*, 21:157-78 (1997).
Haren et al., "Integrating DNA: transposases and retroviral integrases", *Annu. Rev. Microbiol.*, 53:245-81 (1999).
Hay et al., Factor VIII inhibitors in mild and moderate-severity haemophilia A. *Haemophilia*, 4: 558-63 (1998).
Hoess pp. 99-109, In: Eckstein et al. (eds.), *Nucleic Acid and Molecular Biology*, vol. 4, Berlin: Springer-Verlag (1990).
Hogan et al., Manipulating the Mouse Embryo: A Laboratory Manual, Cold Spring Harbor, NY: Cold Spring Harbor Laboratory (1986).
Hu et al., "Development of an adenovirus vector with tetracycline-regulatable human tumor necrosis factor alpha gene expression", *Cancer Res.*, 57:3339-43 (1997).
Hwang et al., "Fish as bioreactors: transgene expression of human coagulation factor VII in fish embryos", *Mar. Biotechnol. (NY)*, 6:485-92 (2004).
Ivics et al., "Genetic applications of transposons and other repetitive elements in zebrafish", *Methods Cell Biol.*, 60:99-131 (1999).
Jin et al., "Structures of the toll-like receptor family and its ligand complexes", *Immunity*, 29:182-91 (2008).
Jorgez et al., "Inhibin alpha-iCre mice: Cre deleter lines for the gonads, pituitary, and adrenal", *Genesis*, 44:183-8 (2006).
Kellendonk et al., "Hepatocyte-specific expression of Cre recombinase", *Genesis*, 26:151-3 (2000).
Kim et al., "Transcriptional targeting of replication-defective adenovirus transgene expression to smooth muscle cells in vivo", *J. Clin. Invest.*, 100:1006-14 (1997).
Lacroix-Desmazes et al., "Catalytic IgG from patients with hemophilia A inactivate therapeutic factor VIII", *J. Immunol.*, 177:1355-63 (2006).
Lam, "Application of combinatorial library methods in cancer research and drug discovery", *Anticancer Drug Des.*, 12:145-67 (1997).
Ledermann, "Embryonic stem cells and gene targeting", *Exp. Physiol.*, 85:603-13 (2000).
Lemischka et al., "Developmental potential and dynamic behavior of hematopoietic stem cells", *Cell*, 45:917-27 (1986).
Lindgren et al., "Characterization of inhibitors to FVIII with an ELISA in congenital and acquired haemophilia A", *Haemophilia*, 8:644-8 (2002).
Liu et al., "Solid-substrate room-temperature phosphorescence immunoassay based on an antibody labeled with nanoparticles containing dibromofluorescein luminescent molecules and analytical application", *J. Immunol. Methods*, 307:34-40 (2005).

(56) References Cited

OTHER PUBLICATIONS

Lowe, "Factor IX and thrombosis", *Br. J. Haematol.*, 115:507-13 (2001).

Madsen et al., "A humanized model for multiple sclerosis using HLA-DR2 and a human T-cell receptor", *Nat. Genet.*, 23:343-7 (1999).

Madsen et al., "Mice lacking all conventional MHC class II genes", *Proc. Natl. Acad. Sci. USA*, 96:10338-43 (1999).

Mahendroo et al., "Tissue-specific and hormonally controlled alternative promoters regulate aromatase cytochrome P450 gene expression in human adipose tissue", *J. Biol. Chem.*, 268:19463-70 (1993).

Miyatake et al., "Transcriptional targeting of herpes simplex virus for cell-specific replication", *J. Virol.*, 71:5124-32 (1997).

Mohri et al., "Clinical significance of inhibitors in acquired von Willebrand syndrome", *Blood*, 91:3623-9 (1998).

Moreadith et al., "Gene targeting in embryonic stem cells: the new physiology and metabolism", *J. Mol. Med.*, 75:208-16 (1997).

Mori et al., "Total body irradiation as a method of preparation for bone marrow transplantation: a new technique and review", *Jpn J. Clin. Oncol.*, 14 Suppl 1:457-63 (1984).

Nagy et al., "Derivation of completely cell culture-derived mice from early-passage embryonic stem cells", *Proc. Natl. Acad. Sci. USA*, 90:8424-8 (1993).

Niemann et al., Expression of human blood clotting factor VIII in the mamary gland of transgenic sheep. *Transgenic Res.* 8: 237-47 (1999).

Osterud, "Factor VII and haemostasis", *Blood Coagul Fibrinolysis*, 1:175-81 (1990).

Ozaki et al., "Use of von Willebrand factor promoter to transduce suicidal gene to human endothelial cells, HUVEC", *Hum. Gene Ther.*, 7:1483-90 (1996).

Pitas et al., "Anti-phencyclidine monoclonal antibody binding capacity is not the only determinant of effectiveness, disproving the concept that antibody capacity is easily surmounted", *Drug Metab. Dispos.*, 34:906-12 (2006).

Reding, "Immunological aspects of inhibitor development", Haemophilia, 12 Suppl 6: 30-35 (2006).

Reipert et al., "Mechanisms of action of immune tolerance induction against factor VIII in patients with congenital haemophilia A and factor VIII inhibitors", *Br. J. Haematol.*, 136:12-25 (2007).

*Remington's Pharmaceutical Sciences*, 19th ed., Easton, Pa: Mack Publishing Co. (1995).

Reznikoff et al., "Tn5: A molecular window on transposition", *Biochem. Biophys. Res. Commun.*, 266:729-34 (1999).

Rulicke et al., "Germ line transformation of mammals by pronuclear microinjection", *Exp. Physiol.*, 85:589-601 (2000).

Saenko et al., "Strategies towards a longer acting factor VIII", *Haemophilia*, 12 Suppl 3: 42-51 (2006).

Sahud et al., "ELISA system for detection of immune responses to FVIII: a study of 246 samples and correlation with the Bethesda assay", *Haemophilia*, 13:317-22 (2007).

Sallah, Inhibitors to clotting factors. *Ann. Hematol.*, 75:1-7 (1997).

Sambrook et al. (eds.), *Molecular Cloning a Laboratory Manual*, 2nd ed., Cold Spring Harbor Laboratory Press (1989).

Schnieke et al., "Human factor IX transgenic sheep produced by transfer of nuclei from transfected fetal fibroblasts", *Science*, 278:2130-3 (1997).

Schultz et al., "Single-target molecule detection with nonbleaching multicolor optical immunolabels", *Proc. Natl. Acad. Sci. USA*, 97:996-1001 (2000).

Seung et al., "Genetic radiotherapy overcomes tumor resistance to cytotoxic agents", *Cancer Res.*, 55:5561-5 (1995).

Shi et al., "Factor VIII ectopically targeted to platelets is therapeutic in hemophilia A with high-titer inhibitory antibodies", *J. Clin. Invest.*, 116:1974-82 (2006).

Shi et al., "Modulation of the specificity and activity of a cellular promoter in an adenoviral vector", *Hum. Gene Ther.*, 8:403-10 (1997).

Simpson et al., "Tissue-specific promoters regulate aromatase cytochrome P450 expression", *Clin. Chem.*, 39:317-24 (1993).

Soff et al., "Autoantibody to von Willebrand factor in systemic lupus erythematosus", *J. Lab. Clin. Med.*, 121:424-30 (1993).

Sun et al., "Single-event analysis of the packaging of bacteriophage T7 DNA concatemers in vitro", *Biophys. J.*, 77:1627-37 (1999).

Suzuki et al., "Regulatable promoters for use in gene therapy applications: modification of the 5'-flanking region of the CFTR gene with multiple cAMP response elements to support basal, low-level gene expression that can be upregulated by exogenous agents that raise intracellular levels of cAMP", *Hum. Gene Ther.*, 7:1883-93 (1996).

Tang et al., "A Cre/loxP-deleter transgenic line in mouse strain 129S1/SvlmJ", *Genesis*, 32:199-202 (2002).

Van Helden et al., Immune tolerance to human factor VIII induced by liver-specific expression of a human factor VIII transgene in hemophilic mice. *Blood*, 112(1): 1162 (2008).

Von Depka, Immune tolerance therapy in patients with acquired hemophilia. *Hematology*, 9: 245-57 (2004).

Waddington et al., "In utero gene transfer of human factor IX to fetal mice can induce postnatal tolerance of the exogenous clotting factor", *Blood*, 101:1359-66 (2003).

Wales et al., "Targeting intracellular signaling: a novel approach to vaccination", *Expert Rev. Vaccines*, 6:971-80 (2007).

Wood et al., "Expression of active human factor VIII from recombinant DNA clones", *Nature*, 312:330-7 (1984).

Yagi et al., "A novel ES cell line, TT2, with high germline-differentiating potency", *Anal. Biochem.*, 214:70-6 (1993).

Zakarija et al., Acquired hemophilia: Diagnosis and management. *Curr. Hematol. Rep.*, 1: 27-33 (2002).

International Search Report, PCT/US2008/088564, European Patent Office, dated Aug. 13, 2009.

\* cited by examiner

FIGURE 3

```
GAATTCCCGCAGCCCTCATTTGCAGGGGAAGATGATTCCTCCCAGATTTGCCGGGGTGCTGCTTGCTCTGGCCCT
CATTTTGCCAGGGACCCTTTGTGCAGAAGCAACTCGCGGCAGGTCATCCACGGCCCGATGCAGCCTTTTCGGAAG
TGACTTCGTCAACACCTTTGATGGGAGCATGTACAGCTTTGCGGGATACTGCAGTTACCTCCTGGCAGGGGCTG
CCAGAAACGCTCCTTCTCGATTATTGGGGACTTCCAGAATGGCAAGAGAGTGAGCCTCTCCGTGTATCTTGGGGA
ATTTTTTGACATCCATTTGTTTGTCAATGGTACCGTGACACAGGGGGACCAAAGAGTCTCCATGCCCTATGCCTC
CAAAGGGCTCTATCTAGAAACTGAGGCTGGGTACTACAAGCTGTCCGGTGAGGCCTATGGCTTTGTGGCCAGGAT
CGATGGCAGCGGCAACTTTCAAGTCCTGCTGTCAGACAGATACTTCAACAAGACCTGCGGGCTGTGTGGCAACTT
TAACATCTTTGCTGAAGATGACTTTATGACCCAAGAAGGGACCTTGACCTCGGACCCTTATGACTTTGCCAACTC
ATGGGCTCTGACCAGTGGAGAACAGTGGTGTGAACGGGCATCTCCTCCCAGCAGCTCATGCAACATCTCCTCTGG
GGAAATGCAGAAGGGCCTGTGGGAGCAGTGCCAGCTTCTGAAGAGCACCTCGGTCTTTGCCCGCTGCCACCCTCT
GGTGGACCCCGAGCCTTTTGTGGCCCTGTCTGAAGACTTTGTGTGAGTGTGCTGGGGGGCTGGAGTGCGCCTG
CCCTGCCCTCCTGGAGTACGCCCGGACCTGTGCCCACCAGGGAATGGTGCTGTACGGCTGGACCGACCACAGCGC
GTGCAGCCCAGTGTGCCCTGCTGGTATGGAGTATAGGCAGTGTGTGTCCCCTTGCGCCAGGACCTGCCAGAGCCT
GCACATCAATGAAATGTGTCAGGAGCGATGCGTGGATGGCTGCAGCTGCCCTGACCGACAGCTCCTGGATGAAGG
CCTCTGCGTGGAGAGCACCGAGTGTCCCTGCGTGCATTCCGGAAAGCGCTACCCTCCCGGCACCTCCCTCTCTCG
AGACTGCAACACCTGCATTTGCCGAAAACAGCCAGTGGATCTGCAGCAATGAAGAATGTCCAGGGGAGTGCCTTGT
CACAGGTCAATCACACTTCAAGAGCTTTGACAACAGATACTTCACCTTCAGTGGGATCTGCCAGTACCTGCTGGCC
CCGGGATTGCCAGGACCACTCCTTCTCCATTGTCATTGAGACTGTCCAGTGTGCTGATGACCGCGACGCTGTGTG
CACCCGCTCCGTCACCGTCCGGCTGCCTGGCCTGCACAACAGCCTTGTGAAACTGAAGCATGGGGCAGGAGTTGC
CATGGATGGCCAGGACGTCCAGCTCCCCCTCCTGAAAGGTGACCTCCGCATCCAGCATACAGTGACGGCCTCCGT
GCGCCTCAGCTACGGGGAGGACCTGCAGATGGACTGGGATGGCCGCGGGAGGCTGCTGGTGAAGCTGTCCCCCGT
CTATGCCCGGAAGACCTGCGGCCTGTGTGGAATTACAATGGCAACCAGGGCGACGACTTCCTTACCCCCTCTGG
GCTGGCGGAGCCCCGGGTGGAGGACTTCGGGAACGCCTGGAAGCTGCACGGGGACTGCCAGGACCTGCAGAAGCA
GCACAGCGATCCCTGCGCCCTCAACCCCGCATGACCAGGTTCTCCGAGGAGGCGTGCGCGGTCCTGACGTCCCC
CACATTCGAGGCCTGCCATCGTGCCGTCAGCCCCGCTGCCCTACCTGCGGAACTGCGCTACGACGTGTGCTCCTG
CTCGGACGGCCGCGAGTGCCTGTGCGGCGCCCTGGCCAGCTATGCCGCGGCCTGCGCGGGGACAGGCGTGCGCGT
CGCCGTGGCGCGAGCCAGGCCGCTGTGAGCTGAACTGCCCGAAAGCCCAGGTGTACCTGCAGTGCGGGACCCCCTG
CAACCTGACCTGCCGCTCTCTCTCTTACCCGGATGAGGAATGCAATGAGGCCTGCCTCGAGGGCTGCTTCTGCCC
CCCAGGGCTCTACATGGATGAGAGGGGGGACTGCGTCCCAAGGCCCAGTGCCCCTGTTACTATGACGGTCAGAT
CTTCCAGCCAGAAGACATCTTCTCAGACCATCACACCATGTGCTACTGTGAGGATGGCTTCATGCACTGTACCAT
GAGTGGAGTCCCCGGAAGCTTGCTGCCTGACGCTGTCCTCAGCAGTCCCCTGTCTCATCGCAGCAAAAGGAGCCT
ATCCTGTCGGCGCCCCATGGTGAAGCTGGTGTCTCCCGCTCACAACCTGCGGGCTGAAGGGCTCGAGTGTACCAA
AACGTGCCAGAACTATGCCTGGAGTGCATGAGCATGGGCTGTGTCTCTGGCTGCCTCTGCCCCCGGGCATGGT
CCGGCATGAGAACAGATGTGTGGCCCTGGAAAGGTGTCCCTGCTTCCATCAGGGCAAGGACTATGCCCCTGGAGA
AACAGTGAAGATTGGCTGCAACACTTGTGTCTGTCGGGACCGGAAGTGGAACTGCACAGACCATGTGTGTGATGC
CACGTGCTCCACGATCGGCATGGCCCACTACCTCACCTTCGACGGGCTCAAATACCTGTTCCCCGGGAGTGCCA
GTACGTTCTGGTGCAGGATTACTGCGGCACTAACCCTGGGACCTTTCGGATCCTAGTGGGGAATAAGGGATGCAG
CCACCCCTCAGTGAAATGCAAGAAACGGGTCACCATCCTGGTGGAGGGAGGAGAGATTGAGCTGTTTGACGGGGA
GGTGAATGTGAAGAGGCCCATGAAGGATGAGACTCACTTTCAGCTCGTGGAGTCTGGCCGGTACATCATTCTGCT
GCTGGGCAAAGCCCTCTCCGTGGTCTGGGACGCCACCCTGGACATCTCCCGTGCTGGAAGCAGACATACCAGGA
GAAAGTGTGTGGCCTGTGTGGGAATTTTGATGGCATCCAGAACAATGACCTCACCAGCAGCAACCTCCAAGTGGA
CGAAGACCCTGTGGACTTTGGGAACTCCTGGAAAGTGAGCTCGCAGTGTGCTGACACCAGAAAAGTGCCTCTGGA
CTCATCCCCTGCCACCTGCCATAACAACATCATGAAGCAGACGATGGTGGATTCCTCCTGTAGAATCCTTACCAG
TGACGTCTTCCAGGACTGCAACAAGCTGGTGGACCCCGAGCCATATCTGGATGTCTGCATTTACGACACCTGCTC
CTGTGAGTCCATTGGGGACTGCGCCTGCTTCTGCGACACCATTGCTGCCTATGCCCACGTGTGTGCCCAGCATGG
CAAGGTGGTGACCTGGAGGACGGCCACATTGTGCCCCAGACCTGCGAGGAGAGGAATCTCCGGGAGAACGGGTA
TGAGTGTGAGTGGCGCTATAACAGCTGTGCACCTGCCTGTCAAGTCACGTGTCAGCACCCTCAGCCACTGGCCTG
CCCTGTGCAGTGTGTGGAGGGCTGCCATGCCCACTGCCCTCCAGGGAAAATCTGGATGAGCTTTTGCAGACCTG
CGTTGACCCTGAAGACGTCCAGTGTGTGAGGTGGCTGCCGGCGTTTGCCTCAGGAAAGAAAGTCACCTTGAA
TCCCAGTGACCCTGAGCACTGCCAGATTTGCCACTGTGATGTTGTCAACCTCACCTGTGAAGCCTGCCAGGAGCC
GGGAGGCCTGGTGGTGCCTCCCACAGATGCCCCGGTGAGCCCCACCACTCTGTATGTGGAGGACATCTCGGAACC
GCCCGTTGCACGATTTCTACTGCAGCAGGCTACTGGACCTGGTCTTCCTGCTGGATGGCTCCTCCAGGCTGTCCGA
GGCTGAGTTTGAAGTGCTGAAGGCCTTTGTGGTGGACATGATGGAGCGGCTGCGCATCTCCCAGAAGTGCGTCCG
CGTGGCCGTGGTGGAGTACCACGACGGCTCCCACGCCTACATCGGGCTCAAGGACCGGAAGCGACCGTCAGAGCT
GCGGCGCATTGCCAGCCAGGTGAAGTATGCGGGCAGCCAGGTGGCCTCCACCAGGGAGGTCTTGAAATACACACT
GTTCCAAATCTTCAGCAAGATCGACCGCCCTGAAGCCTCCCGCATCGCCCTGCTCCTGATGGCCAGCCAGGAGCC
CCAACGGATGTCCCGGAACTTTGTCCCGCTACGTCCAGGGCCTGAAGAAGAAGAAGGTCATTGTGATCCCGGTGGG
CATTGGGCCCCATGCCAACCTCAAGCAGATCCGCCTCATCGAGAAGCAGGCCCCTGAGAACAAGGCCTTCGTGCT
```

```
GAGCAGTGTGGATGAGCTGGAGCAGCAAAGGGACGAGATCGTTAGCTACCTCTGTGACCTTGCCCCTGAAGCCCC
TCCTCCTACTCTGCCCCCCCACATGGCACAAGTCACTGTGGGCCCGGGGCTCTTGGGGGTTTCGACCCTGGGCCC
CAAGAGGAACTCCATGGTTCTGGATGTGGCGTTCGTCCTGGAAGGATCGGACAAAATTGGTGAAGCCGACTTCAA
CAGGAGCAAGGAGTTCATGGAGGAGGTGATTCAGCGGATGGATGTGGGCCAGGACAGCATCCACGTCACGGTGCT
GCAGTACTCCTACATGGTGACCGTGGAGTACCCCTTCAGCGAGGCACAGTCCAAAGGGGACATCCTGCAGCGGGT
GCGAGAGATCCGCTACCAGGGCGGCAACAGGACCAACACTGGGCTGGCCCTGCGGTACCTCTCTGACCACAGCTT
CTTGGTCAGCCAGGGTGACCGGGAGCAGGCGCCCAACCTGGTCTACATGGTCACCGGAAATCCTGCCTCTGATGA
GATCAAGAGGCTGCCTGGAGACATCCAGGTGGTGCCCATTGGAGTGGGCCCTAATGCCAACGTGCAGGAGCTGGA
GAGGATTGGCTGGCCCAATGCCCCTATCCTCATCCAGGACTTTGAGACGCTCCCCCGAGAGGCTCCTGACCTGGT
GCTGCAGAGGTGCTGCTCCGGAGAGGGGCTGCAGATCCCCACCCTCTCCCTGCACCTGACTGCAGCCAGCCCCT
GGACGTGATCCTTCTCCTGGATGGCTCCTCCAGTTTCCCAGCTTCTTATTTTGATGAAATGAAGAGTTTCGCCAA
GGCTTTCATTTCAAAAGCCAATATAGGGCCTCGTCTCACTCAGGTGTCAGTGCTGCAGTATGGAAGCATCACCAC
CATTGACGTGCCATGGAACGTGGTCCCGGAGAAAGCCCATTTGCTGAGCCTTGTGGACGTCATGCAGCGGGAGGG
AGGCCCCAGCCAAATCGGGGATGCCTTGGGCTTTGCTGTGCGATACTTGACTTCAGAAATGCATGGTGCCAGGCC
GGGAGCCTCAAAGGCGGTGGTCATCCTGGTCACGGACGTCTCTGTGGATTCAGTGGATGCAGCAGCTGATGCCGC
CAGGTCCAACAGAGTGACAGTGTTCCCTATTGGAATTGGAGATCGCTACGATGCAGCCCAGCTACGGATCTTGGC
AGGCCCAGCAGGCGACTCCAACGTGGTGAAGCTCCAGCGAATCGAAGACCTCCCTACCATGGTCACCTTGGGCAA
TTCCTTCCTCCACAAACTGTGCTCTGGATTTGTTAGGATTTGCATGGATGAGGATGGGAATGAGAAGAGGCCCGG
GGACGTCTGGACCTTGCCAGACCAGTGCCACACCGTGACTTGCCAGCCAGATGGCCAGACCTTGCTGAAGAGTCA
TCGGGTCAACTGTGACCGGGGGCTGAGGCCTTCGTGCCCTAACAGCCAGTCCCTGTTAAAGTGGAAGAGACCTG
TGGCTGCCGCTGGACCTGCCCCTGCGTGTGCACAGGCAGCTCCACTCGGCACATCGTGACCTTTGATGGGCAGAA
TTTCAAGCTGACTGGCAGCTGTTCTTATGTCCTATTTCAAAACAAGGAGCAGGACCTGGAGGTGATTCTCCATAA
TGGTGCCTGCAGCCCTGGAGCAAGGCAGGGCTGCATGAAATCCATCGAGGTGAAGCACAGTGCCCTCTCCGTCGA
GCTGCACAGTGACATGGAGGTGACGGTGAATGGGAGACTGGTCTCTGTTCCTTACGTGGGTGGGAACATGGAAGT
CAACGTTTATGGTGCCATCATGCATGAGGTCAGATTCAATCACCTTGGTCACATCTTCACATTCACTCCACAAAA
CAATGAGTTCCAACTGCAGCCTCAGCCCCAAGACTTTTGCTTCAAAGACGTATGGTCTGTGTGGGATCTGTGATGA
GAACGCAGCCAATGACTTCATGCTGAGGCATGGCACAGTCACCACAGACTGGAAAACACTTGTTCAGGAATGGAC
TGTGCAGCGGCCAGGGCAGACGTGCCAGCCCATCCTGGAGGAGCAGTGTCTTGTCCCCGACAGCTCCCACTGCCA
GGTCCTCCTCTTACCACTGTTTGCTGAATGCCACAAGGTCCTGGCTCCAGCCACATTCTATGCCATCTGCCAGCA
GGACAGTTGCCACCAGGAGCAAGTGTGTGAGGTGATCGCCTCTTATGCCCACCTCTGTCGGACCAACGGGGTCTG
CGTTGACTGGAGGACACCTGATTTCTGTGCTATGTCATGCCCACCATCTCTGGTCTACAACCACTGTGAGCATGG
CTGTCCCCGGCACTGTGATGGCAACGTGAGCTCCTGTGGGGACCATCCCTCCGAAGGCTGTTTCTGCCCTCCAGA
TAAAGTCATGTTGGAAGGCAGCTGTGTCCCTGAAGAGGCCTGCACTCAGTGCATTGGTGAGGATGGAGTCCAGCA
CCAGTTCCTGGAAGCCTGGGTCCCGGACCACCAGCCCTGTCAGATCTGCACATGCCTCAGCGGGCGGAAGGTCAA
CTGCAACAACAGCCCTGCCCCACGGCCAAAGCTCCCACGTGTGGCCTGTGTGAAGTAGCCCGCTCCGCCAGAA
TGCAGACCAGTGCTGCCCCGAGTATGAGTGTGTGTGACCCAGTGAGCTGTGACCTGCCCCCAGTGCCTCACTG
TGAACCTGGCCTCCAGCCCACACTGACCAACCCTGGCGAGTGCAGACCCAACTTCACCTGCCCTGCAGGAAGGA
GGAGTGCAAAAGAGTGTCCCCACCCTCCTGCCCCCCGCACCGTTTGCCCACCCTTCGGAAGACCCAGTGCTGTCA
TGAGTATGAGTGTGCCTGCAACTGTGTCAACTCCACAGTGAGCTGTCCCCTTGGGTACTTGGCCTCAACCGCCAC
CAATGACTGTGGCTGTACCACAACCACCTGCCTTCCCGACAAGGTGTGTGTCCACCGAAGCACCATCTACCCTGT
GGGCCAGTTCTGGAGGAGGGCTGCGATGTGTGCACCTGCACCGACATGGAGGATGCCGTGATGGGCCTCCGCGT
GGCCCAGTGCTCCCAGAAGCCCTGTGAGGACAGCTGTCGGTCGGCTTCACTTACGTTCTGCATGAAGGCGAGTG
CTGTGGAAGGTGCCTGCCATCTGCCTGTGAGGTGGTGACCGGCTCACCGCGGGGGGACTCCCAGTCTTCCTGGAA
GAGTGTCGGCTCCCAGTGGGCCTCCCCGGAGAACCCTGCCTCATCAATGAGTGTGTCCGAGTGAAGGAGGAGGT
CTTTATACAACAAAGGAACGTCTCCTGCCCCAGCTGGAGGTCCCTGTCTGCCCCTCGGGCTTTCAGCTGAGCTG
TAAGACCTCAGCCGTGCTGCCCAAGCTGTCGCTGTGAGCCCATGGAGGCCTGCATGCTCAATGGCACTGTCATTGG
GCCCGGGAAGACTGTGATGATCGATGTGTGCACGACCTGCCGCTGCATGGTGCAGGTGGGGGTCATCTCTGGATT
CAAGCTGGAGTCCACGAAGACCACCTGCAACCCCTGCCCCCTGGGTTACAAGGAAGAAAATAACACAGGTGAATG
TTGTGGGAGATGTTTGCCTACGGCTTGCACCATTCAGCTAAGAGGAGGACAGATCATGACACTGAAGCGTGATGA
GACGCTCCAGGATGGCTGTGATACTCACTTCTGCAAGGTCAATGAGAGAGGGAGTACTTCTGGGAGAAGAGGGT
CACAGGCTGCCCACCCTTTGATGAACACAAGTGTCTGGCTGAGGGAGGTAAAATTATGAAAATTCCAGGCACCTG
CTGTGACACATGTGAGGAGCCTGAGTGCAACGACATCACTGCCAGGCTGCAGTATGTCAAGGTGGGAAGCTGTAA
GTCTGAAGTAGAGGTGGATATCCACTACTGCCAGGGCAAATGTGCCAGCAAAGCCATGTACTCCATTGACATCAA
CGATGTGCAGACGAGCTGTCCTGCTCCTCCGACACGGACGGACCCCATGCAGGTGGCCCTGCACTGCACCAA
TGGCTCTGTTGTGTACCATGAGGTTCTCAATGCCATGGAGTGCAAATGCTCCCCCAGGAAGTGCAGCAAGTGAGG
CTGCTGCAGCTGCATGGGTGCCTGCTGCTGCCGG<u>AATTC</u> (SEQ ID NO: 16)
```

FIGURE 3 (CONTINUED)

For all subtypes, 8 i.v. doses, weekly intervals

SEQUENCE LISTING

```
<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: LAdi - A1

<400> SEQUENCE: 1
actatgcctg cggctcttga tgg                                              23

<210> SEQ ID NO 2
<211> LENGTH: 25
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: B1

<400> SEQUENCE: 2
tcgtggtctc tgtgtgttca cagcc                                            25

<210> SEQ ID NO 3
```

```
<211> LENGTH: 25
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: LApr - C1

<400> SEQUENCE: 3
tgtgcaggct gttgagtggc taagg                                      25

<210> SEQ ID NO 4
<211> LENGTH: 28
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: D1

<400> SEQUENCE: 4
ccatcacatg gtacaatcct gtgctacc                                   28

<210> SEQ ID NO 5
<211> LENGTH: 24
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: SA - E1

<400> SEQUENCE: 5
ttctgagaat gtggagggca gtgg                                       24

<210> SEQ ID NO 6
<211> LENGTH: 28
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: F1

<400> SEQUENCE: 6
tccacctaga gaaggagcct gtgtaagg                                   28

<210> SEQ ID NO 7
<211> LENGTH: 294
<212> TYPE: DNA
<213> ORGANISM: Artificial Sequence
<220> FEATURE:
<223> OTHER INFORMATION: Synthetic Polynucleotide

<400> SEQUENCE: 7
ggtaccggac gcgtgttaac caattgccga tatccactac tgccagggca aatgtgccag      60
caaagccatg tactccattg acatcaacga tgtgcaggac cagtgctcct gctgctctcc     120
gacacggacg gagcccatgc aggtggccct gcactgcacc aatggctctg ttgtgtacca     180
tgaggttctc aatgccatgg agtgcaaatg ctcccccagg aagtgcagca agtgaggctg     240
ctgcagctgc atgggtgcct gctgctgccg gcttcgaatc gaattctgga gctc          294
```

```
<210> SEQ ID NO 8
<211> LENGTH: 906
<212> TYPE: DNA
<213> ORGANISM: Artificial Sequence
<220> FEATURE:
<223> OTHER INFORMATION: Synthetic Polynucleotide

<400> SEQUENCE: 8
attaattaag tttaaacgag ttaactagaa ttctggcttt attaatctct gttcttcaca      60
ttcttccatg cacttttgtc tgaagtctga caaatacgag aaccttaaaa tactctgcga     120
ttgtcactgc cctttgtgcc tactgtctag ttctctggct ccaccttgtt ctccttttta     180
cgtcttttc ttgaaaccgt accgtaagca ttgcccatct tcctgcctca gcccctgtt      240
tatttattac tttaactttt taatttctca ctattactgt tattgtctta tgaagtcact     300
gcctgttcac atttacctca taactaccaa attctctgtt gattttttt tttttttg      360
agacagggtt tctctgtgta gccctggctg tcctggaact cactctgtag accaggctgg     420
cctcaaactc agagatccgc ctgcctctgc ctcccgagtg ctgggattaa aggcatgcgc     480
caccactgcc aggcctctct gttgcttttt atttctagca ttttctctct gggtttaact     540
tccttcttcc tgaagaacct tctttagcag tccattcagc aaggcagggg atggcaagct     600
catcttttc tggcaagaga agatggccct aactctgaat gatgacttag ttctgggaac     660
tagttactac gccctcttcc acagcactca gacctaactc atctgagacc gatctctgtg     720
actatgtgca ggctgttgag tggctaagga aacagtcctg gctagcacat gcattgatgg     780
tagcttgtcc ttgccacctc tctggacggt gagaaccagc tcatttcctt tttattttat     840
tttatttgc agacgcgttg caattgcgta cgcttacgta gtcctaggaa tcgcgattgg     900
cgcgcc                                                                906

<210> SEQ ID NO 9
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 9
ctacttccat ttgtcacgtc ctgcacg                                          27

<210> SEQ ID NO 10
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 10
cagctcctgc cttgttactg tgaccc                                           26

<210> SEQ ID NO 11
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: huFVII MS2

<400> SEQUENCE: 11
gaatggagct cagttgtg                                                    18
```

<210> SEQ ID NO 12
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: huFVII MS2 rev

<400> SEQUENCE: 12
atcaggttcc tccagttc                                                18

<210> SEQ ID NO 13
<211> LENGTH: 23
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: huFVIII-FAM

<400> SEQUENCE: 13
ccaaagctgg aatttggcgg gtg                                          23

<210> SEQ ID NO 14
<211> LENGTH: 25
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: forward huFVIII

<400> SEQUENCE: 14
ggcactgtac aatctctatc caggt                                        25

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: reverse huFVIII

<400> SEQUENCE: 15
gatgctcgcc aataaggcat                                              20

<210> SEQ ID NO 16
<211> LENGTH: 8514
<212> TYPE: DNA
<213> ORGANISM: Artificial Sequence
<220> FEATURE:
<223> OTHER INFORMATION: Synthetic Polynucleotide

<400> SEQUENCE: 16
gaattcccgc agccctcatt tgcaggggaa gatgattcct gccagatttg ccggggtgct    60
gcttgctctg gccctcattt tgccagggac cctttgtgca gaaggaactc gcggcaggtc   120
atccacggcc cgatgcagcc tttttcggaag tgacttcgtc aacaccttg atggagcat    180 gtacagcttt gcgggatact gcagttacct cctggcaggg ggctgccaga aacgctcctt   240

-continued

| | |
|---|---|
| ctcgattatt ggggacttcc agaatggcaa gagagtgagc ctctccgtgt atcttgggga | 300 |
| atttttgac atccatttgt ttgtcaatgg taccgtgaca caggggacc aaagagtctc | 360 |
| catgccctat gcctccaaag ggctgtatct agaaactgag gctgggtact acaagctgtc | 420 |
| cggtgaggcc tatggctttg tggccaggat cgatggcagc ggcaactttc aagtcctgct | 480 |
| gtcagacaga tacttcaaca agacctgcgg gctgtgtggc aactttaaca tctttgctga | 540 |
| agatgacttt atgacccaag aagggacctt gacctcggac ccttatgact ttgccaactc | 600 |
| atgggctctg agcagtggag aacagtggtg tgaacgggca tctcctccca gcagctcatg | 660 |
| caacatctcc tctggggaaa tgcagaaggg cctgtgggag cagtgccagc ttctgaagag | 720 |
| cacctcggtg tttgcccgct gccaccctct ggtggacccc gagccttttg tggccctgtg | 780 |
| tgagaagact ttgtgtgagt gtgctggggg gctggagtgc gcctgccctg ccctcctgga | 840 |
| gtacgcccgg acctgtgccc aggagggaat ggtgctgtac ggctggaccg accacagcgc | 900 |
| gtgcagccca gtgtgccctg ctggtatgga gtataggcag tgtgtgtccc cttgcgccag | 960 |
| gacctgccag agcctgcaca tcaatgaaat tgtgtcagga cgatgcgtgg atggctgcag | 1020 |
| ctgccctgag ggacagctcc tggatgaagg cctctgcgtg gagagcaccg agtgtccctg | 1080 |
| cgtgcattcc ggaaagcgct accctcccgg cacctccctc tctcgagact gcaacacctg | 1140 |
| catttgccga aacagccagt ggatctgcag caatgaagaa tgtccagggg agtgccttgt | 1200 |
| cacaggtcaa tcacacttca agagctttga caacagatac ttcaccttca gtgggatctg | 1260 |
| ccagtacctg ctggcccggg attgccagga ccactccttc tccattgtca ttgagactgt | 1320 |
| ccagtgtgct gatgaccgcg acgctgtgtg cacccgctcc gtcaccgtcc ggctgcctgg | 1380 |
| cctgcacaac agccttgtga aactgaagca tgggcagga gttgccatgg atggccagga | 1440 |
| cgtccagctc cccctcctga aggtgacct ccgcatccag catacagtga cggcctccgt | 1500 |
| gcgcctcagc tacggggagg acctgcagat ggactgggat ggccgcggga ggctgctggt | 1560 |
| gaagctgtcc cccgtctatg ccgggaagac ctgcggcctg tgtgggaatt acaatggcaa | 1620 |
| ccagggcgac gacttcctta ccccctctgg gctggcggag cccgggtgg aggacttcgg | 1680 |
| gaacgcctgg aagctgcacg gggactgcca ggacctgcag aagcagcaca gcgatccctg | 1740 |
| cgccctcaac ccgcgcatga ccaggttctc cgaggaggcg tgcgcggtcc tgacgtcccc | 1800 |
| cacattcgag gcctgccatc gtgccgtcag cccgctgccc tacctgcgga actgccgcta | 1860 |
| cgacgtgtgc tcctgctcgg acggccgcga gtgcctgtgc ggcgccctgg ccagctatgc | 1920 |
| cgcggcctgc gcggggagag gcgtgcgcgt cgcgtggcgc gagccaggcc gctgtgagct | 1980 |
| gaactgcccg aaaggccagg tgtacctgca gtgcgggacc cctgcaacc tgacctgccg | 2040 |
| ctctctctct tacccggatg aggaatgcaa tgaggcctgc ctggagggct gcttctgccc | 2100 |
| cccagggctc tacatggatg agagggggga ctgcgtgccc aaggcccagt gccctgttta | 2160 |
| ctatgacggt gagatcttcc agccagaaga catcttctca gaccatcaca ccatgtgcta | 2220 |
| ctgtgaggat ggcttcatgc actgtaccat gagtggagtc cccggaagct tgctgcctga | 2280 |
| cgctgtcctc agcagtcccc tgtctcatcg cagcaaaagg agcctatcct gtcggccccc | 2340 |
| catggtcaag ctggtgtgtc ccgctgacaa cctgcgggct gaagggctcg agtgtaccaa | 2400 |
| aacgtgccag aactatgacc tggagtgcat gagcatgggc tgtgtctctg gctgcctctg | 2460 |
| cccccccggc atggtccggc atgagaacag atgtgtggcc ctggaaaggt gtccctgctt | 2520 |
| ccatcagggc aaggagtatg cccctggaga aacagtgaag attggctgca acacttgtgt | 2580 |
| ctgtcgggac cggaagtgga actgcacaga ccatgtgtgt gatgccacgt gctccacgat | 2640 |

```
cggcatggcc cactacctca ccttcgacgg gctcaaatac ctgttccccg gggagtgcca    2700
gtacgttctg gtgcaggatt actgcggcag taaccctggg acctttcgga tcctagtggg    2760
gaataaggga tgcagccacc cctcagtgaa atgcaagaaa cgggtcacca tcctggtgga    2820
gggaggagag attgagctgt ttgacgggga ggtgaatgtg aagaggccca tgaaggatga    2880
gactcacttt gaggtggtgg agtctggccg gtacatcatt ctgctgctgg caaagccct    2940 ctccgtggtc tgggaccgcc acctgagcat tccgtggtc ctgaagcaga cataccagga    3000
gaaagtgtgt ggcctgtgtg ggaattttga tggcatccag aacaatgacc tcaccagcag    3060
caacctccaa gtgaggaag accctgtgga ctttgggaac tcctggaaag tgagctcgca    3120
gtgtgctgac accagaaaag tgcctctgga ctcatcccct gccacctgcc ataacaacat    3180
catgaagcag acgatggtgg attcctcctg tagaatcctt accagtgacg tcttccagga    3240
ctgcaacaag ctggtggacc ccgagccata tctggatgtc tgcatttacg acacctgctc    3300
ctgtgagtcc attggggact cgcctgctt ctgcgacacc attgctgcct atgcccacgt    3360
gtgtgcccag catggcaagg tggtgacctg gaggacggcc acattgtgcc cccagagctg    3420
cgaggagagg aatctccggg agaacgggta tgagtgtgag tggcgctata cagctgtgc    3480 acctgcctgt caagtcacgt gtcagcaccc tgagccactg gcctgccctg tgcagtgtgt    3540
ggagggctgc catgcccact gccctccagg gaaaatcctg gatgagcttt tgcagacctg    3600
cgttgaccct gaagactgtc cagtgtgtga ggtggctggc cggcgttttg cctcaggaaa    3660
gaaagtcacc ttgaatccca gtgaccctga gcactgccag atttgccact gtgatgttgt    3720
caacctcacc tgtgaagcct gccaggagcc gggaggcctg gtggtgcctc ccacagatgc    3780
cccggtgagc cccaccactc tgtatgtgga ggacatctcg gaaccgccgt tgcacgattt    3840
ctactgcagc aggctactgg acctggtctt cctgctggat ggctcctcca ggctgtccga    3900
ggctgagttt gaagtgctga aggcctttgt ggtggacatg atggagcggc tgcgcatctc    3960
ccagaagtgg gtccgcgtgg ccgtggtgga gtaccacgac ggctcccacg cctacatcgg    4020
gctcaaggac cggaagcgac cgtcagagct gcggcgcatt gccagccagg tgaagtatgc    4080
gggcagccag gtggcctcca ccagcgaggt cttgaaatac acactgttcc aaatcttcag    4140
caagatcgac cgccctgaag cctcccgcat cgccctgctc ctgatggcca gccaggagcc    4200
ccaacggatg tcccggaact tgtccgcta cgtccagggc ctgaagaaga agaaggtcat    4260
tgtgatcccg gtgggcattg ggccccatgc caacctcaag cagatccgcc tcatcgagaa    4320 gcaggccccct gagaacaagg ccttcgtgct gagcagtgtg gatgagctgg agcagcaaag    4380
ggacgagatc gttagctacc tctgtgacct tgcccctgaa gcccctcctc ctactctgcc    4440
cccccacatg gcacaagtca ctgtgggccc gggctcttg ggggtttcga ccctgggcc    4500 caagaggaac tccatggttc tggatgtggc gttcgtcctg gaaggatcgg acaaaattgg    4560
tgaagccgac ttcaacagga gcaaggagtt catggaggag gtgattcagc ggatggatgt    4620
gggccaggac agcatccacg tcacggtgct gcagtactcc tacatggtga ccgtggagta    4680
ccccttcagc gaggcacagt ccaaagggga catcctgcag cgggtgcgag agatccgcta    4740
ccagggcggc aacaggacca acactgggct ggccctgcgg tacctctctg accacagctt    4800
cttggtcagc cagggtgacc gggagcaggc gcccaacctg gtctacatgg tcaccggaaa    4860
tcctgcctct gatgagatca gagggctgcc tggagacatc caggtggtgc ccattggagt    4920
gggccctaat gccaacgtgc aggagctgga gaggattggc tggcccaatg ccctatcct    4980
```

```
catccaggac tttgagacgc tcccccgaga ggctcctgac ctggtgctgc agaggtgctg    5040
ctccggagag gggctgcaga tccccaccct ctcccctgca cctgactgca gccagcccct    5100
ggacgtgatc cttctcctgg atggctcctc cagtttccca gcttcttatt ttgatgaaat    5160
gaagagtttc gccaaggctt tcatttcaaa agccaatata gggcctcgtc tcactcaggt    5220
gtcagtgctg cagtatggaa gcatcaccac cattgacgtg ccatggaacg tggtcccgga    5280
gaaagcccat ttgctgagcc ttgtggacgt catgcagcgg gagggaggcc ccagccaaat    5340
cggggatgcc ttgggctttg ctgtgcgata cttgacttca gaaatgcatg gtgccaggcc    5400
gggagcctca aaggcggtgg tcatcctggt cacggacgtc tctgtggatt cagtggatgc    5460
agcagctgat gccgccaggt ccaacagagt gacagtgttc cctattggaa ttggagatcg    5520
ctacgatgca gcccagctac ggatcttggc aggcccagca ggcgactcca acgtggtgaa    5580
gctccagcga atcgaagacc tccctaccat ggtcaccttg gcaattcct tcctccacaa     5640
actgtgctct ggatttgtta ggatttgcat ggatgaggat gggaatgaga agaggcccgg    5700
ggacgtctgg accttgccag accagtgcca caccgtgact gccagccag atggccgac     5760
cttgctgaag agtcatcggg tcaactgtga ccggggctg aggccttcgt gccctaacag     5820
ccagtccccct gttaaagtgg aagagacctg tggctgccgc tggacctgcc ctgcgtgtg    5880
cacaggcagc tccactcggc acatcgtgac ctttgatggg cagaatttca agctgactgg    5940
cagctgttct tatgtcctat ttcaaaacaa ggagcaggac ctggaggtga ttctccataa    6000
tggtgcctgc agccctggag caaggcaggg ctgcatgaaa tccatcgagg tgaagcacag    6060
tgccctctcc gtcgagctgc acagtgacat ggaggtgacg tgaatggga gactggtctc     6120
tgttccttac gtgggtggga acatggaagt caacgtttat ggtgccatca tgcatgaggt    6180
cagattcaat caccttggtc acatcttcac attcactcca caaaacaatg agttccaact    6240
gcagctcagc cccaagactt tgcttcaaa gacgtatggt ctgtgtggga tctgtgatga     6300
gaacggagcc aatgacttca tgctgaggga tggcacagtc accacagact ggaaaacact    6360
tgttcaggaa tggactgtgc agcggccagg gcagacgtgc cagcccatcc tggaggagca    6420
gtgtcttgtc cccgacagct cccactgcca ggtcctcctc ttaccactgt ttgctgaatg    6480
ccacaaggtc ctggctccag ccacattcta tgccatctgc cagcaggaca gttgccacca    6540
ggagcaagtg tgtgaggtga tcgcctctta tgcccacctc tgtcggacca acggggtctg    6600
cgttgactgg aggacacctg atttctgtgc tatgtcatgc ccaccatctc tggtctacaa    6660
ccactgtgag catggctgtc cccggcactg tgatggcaac gtgagctcct gtggggacca    6720
tccctccgaa ggctgtttct gccctccaga taaagtcatg ttggaaggca gctgtgtccc    6780
tgaagaggcc tgcactcagt gcattggtga ggatggagtc cagcaccagt tcctggaagc    6840
ctgggtcccg gaccaccagc cctgtcagat ctgcacatgc ctcagcgggc ggaaggtcaa    6900
ctgcacaacg cagccctgcc ccacggccaa agctcccacg tgtggcctgt gtgaagtagc    6960
ccgcctccgc cagaatgcag accagtgctg ccccgagtat gagtgtgtgt gtgacccagt    7020
gagctgtgac ctgcccccag tgcctcactg tgaacgtggc ctccagccca cactgaccaa    7080
ccctggcgag tgcagaccca acttcacctg cgcctgcagg aaggaggagt gcaaaagagt    7140
gtccccaccc tcctgccccc cgcaccgttt gccaccctt cggaagaccc agtgctgtga     7200
tgagtatgag tgtgcctgca actgtgtcaa ctccacagtg agctgtcccc ttgggtactt    7260
ggcctcaacc gccaccaatg actgtggctg taccacaacc acctgccctt ccgacaaggt    7320
gtgtgtccac cgaagcacca tctaccctgt gggccagttc tgggaggagg gctgcgatgt    7380
```

```
gtgcacctgc accgacatgg aggatgccgt gatgggcctc cgcgtggccc agtgctccca    7440
gaagccctgt gaggacagct gtcggtcggg cttcacttac gttctgcatg aaggcgagtg    7500
ctgtggaagg tgcctgccat ctgcctgtga ggtggtgacc ggctcaccgc gggggggactc   7560 ccagtcttcc tggaagagtg tcggctccca gtgggcctcc ccggagaacc cctgcctcat    7620
caatgagtgt gtccgagtga aggaggaggt ctttatacaa caaaggaacg tctcctgccc    7680
ccagctggag gtccctgtct gcccctcggg ctttcagctg agctgtaaga cctcagcgtg    7740
ctgcccaagc tgtcgctgtg agcgcatgga ggcctgcatg ctcaatggca ctgtcattgg    7800
gcccgggaag actgtgatga tcgatgtgtg cacgacctgc cgctgcatgg tgcaggtggg    7860
ggtcatctct ggattcaagc tggagtgcag gaagaccacc tgcaaccct gccccctggg     7920 ttacaaggaa gaaaataaca caggtgaatg ttgtgggaga tgtttgccta cggcttgcac    7980
cattcagcta agaggaggac agatcatgac actgaagcgt gatgagacgc tccaggatgg    8040
ctgtgatact cacttctgca aggtcaatga gagaggagag tacttctggg agaagagggt    8100
cacaggctgc ccacccttg atgaacacaa gtgtctggct gagggaggta aaattatgaa     8160
aattccaggc acctgctgtg acacatgtga ggagcctgag tgcaacgaca tcactgccag    8220
gctgcagtat gtcaaggtgg gaagctgtaa gtctgaagta gaggtggata tccactactg    8280
ccagggcaaa tgtgccagca aagccatgta ctccattgac atcaacgatg tgcaggacca    8340
gtgctcctgc tgctctccga cacggacgga gcccatgcag gtggccctgc actgcaccaa    8400
tggctctgtt gtgtaccatg aggttctcaa tgccatggag tgcaaatgct cccccaggaa    8460
gtgcagcaag tgaggctgct gcagctgcat gggtgcctgc tgctgccgga attc           8514
```

TRANSGENIC NON-HUMAN ANIMALS EXPRESSING HUMAN BLOOD CLOTTING FACTORS AND USES THEREOF

This application is a divisional of U.S. patent application Ser. No. 12/346,432, filed Dec. 30, 2008, now abandoned, which claims the priority benefit of U.S. Provisional Patent Application No. 61/017,920, filed Dec. 31, 2007, and which are incorporated herein by reference.

FIELD OF THE INVENTION

The present invention relates generally to transgenic non-human animals expressing human blood clotting factors, the production and uses thereof.

BACKGROUND OF THE INVENTION

Blood coagulation is a complex process including the sequential interaction of a series of components, in particular of fibrinogen, Factor II, Factor V, Factor VII, Factor VIII, Factor IX, Factor X, Factor XI, Factor XII and von Willebrand's factor. The loss of one of these components or the inhibition of its functionality may cause either an increased tendency of blood coagulation or an inability to clot, which may be life-threatening in some patients.

Factor VIII is a protein found in blood plasma which acts as a cofactor in the cascade of reactions leading to blood coagulation. A deficiency in the amount of Factor VIII activity in the blood results in the clotting disorder hemophilia A, an inherited condition primarily affecting males. Hemophilia A is currently treated with therapeutic preparations of Factor VIII derived from human plasma or manufactured using recombinant DNA technology. Such preparations are administered either in response to a bleeding episode or at frequent, regular intervals to prevent uncontrolled bleeding (prophylaxis).

Von Willebrand factor (vWF) circulates in plasma complexed with factor VIII. vWF complexed with Factor VIII stabilizes the Factor VIII protein and protects it from proteolytic degradation. Due to its function in platelet aggregation, vWF also directly interferes in blood coagulation. Von Willebrand deficiency (vWD) (also known as von Willebrand syndrome) results from either a deficiency or overexpression of vWF. Deficiency of vWF results in a disease similar to hemophilia due to the rapid degradation of Factor VIII lacking vWF cofactor.

Conventional methods for a therapy of Hemophilia A and von Willebrand syndrome use Factor VIII or vWF recovered from plasma or produced by recombinant sources, and there are a number of attempts to treat patients with purified Factor VII, vWF or factor VIII/vWF-complex. The development of antibodies against the administered exogenous protein can decrease the efficacy of treatment and presents a challenge to treatment of these patients. For example, anti-FVIII antibodies are especially prevalent in patients with severe and moderately severe hemophilia, which develop anti-FVIII antibodies at a frequency of 50% (Gilles et al., *Blood* 82:2452-61, 1993; Lacroix-Desmazes et al., *J. Immunol.* 177:1355-63, 2006).

Transgenic animal technology presents a unique opportunity to study the characteristics of human proteins in non-human animals. Recombinant DNA and genetic engineering techniques have made it possible to introduce and express a desired sequence or gene in a recipient animal making it possible to study the effects of a particular molecule in vivo and study agents that bind to the molecule. One procedure for producing transgenic mice requires the recovery of fertilized eggs from newly mated female mice and microinjection of the DNA of the gene of interest into the male pronucleus of the egg. The microinjected eggs are then implanted in the oviducts of one-day pseudopregnant foster mothers and allowed to proceed to term. See, for example, Wagner et al. P.N.A.S. U.S.A. 78:6376-6380 (1981), U.S. Pat. Nos. 4,873,191, and 7,294,755. Another procedure uses embryonic stem cells that are transfected with the gene of interest. Transfected embryonic stem cells are then injected into mouse blastocysts where they take part in the formation of all tissues, including the germ line, thus generating transgenic offspring. This approach, in combination with the homologous recombination technology, offers the possibility of altering embryonic stem cells in a controlled manner and therefore, of generating transgenic mice with a predetermined genome. See, for example: Baribault and Kemler. Embryonic stem cell culture and gene targeting in transgenic mice. Mol Biol Med. 6:481-92, 1989; Ledermann B. Embryonic stem cells and gene targeting. Exp Physiol. 85:603-13, 2000; Moreadith and Radford. Gene targeting in embryonic stem cells: the new physiology and metabolism. J Mol Med. 75:208-16, 1997.

Transgenic mice may be generated to express or overexpress a protein of interest (knock-in mice) or may be generated to delete a gene of interest (knock-out mice). Transgenic mice which express a human protein molecule allow for study of the human molecules in vivo. For example, Shi et al. (J Clin Invest. 116:1974-82, 2006) describe transgenic mice expressing a modified human FVIII protein (lacking the B-domain) designed to circumvent the problem of FVIII inhibitory antibodies which inhibit the activity of recombinant FVIII.

The advent of transgenic technology also allows for development of screening methods which would not be possible without the transgenic animals. For example, in order to study the development of antibodies to an exogenous protein, it is useful to have a model in which the subject is naturally tolerant to the molecule of interest. U.S. Pat. No. 5,470,560 describes a method for screening for the immunogenicity of a polypeptide using a transgenic mouse expressing the protein of interest and tolerant to the protein, administering the exogenous protein to the animal, and screening for antibodies specific for the polypeptide. International Patent Application No. WO2006/056769 describes a method for testing the immunogenicity of a mammalian antigen in an animal transgenic for the cognate MHC class II molecules which would naturally present the mammalian antigen.

Development of antibodies to protein therapeutics is a persistent problem when biopharmaceuticals are used for treatment of disorders. These antibodies often inhibit the activity of the protein therapeutic thereby reducing the efficacy of the treatment or requiring increasing doses of drug to maintain therapeutic levels. Because blood disorders such as hemophilia are often lifelong conditions, the appearance of antibodies specific for therapeutic blood clotting factors is particularly trying for the patients receiving the treatment and challenging for doctors treating these patients.

Thus, there exists a need in the art to develop methods to study the activity of human blood coagulation factors in vivo without study on human patients. Further, there remains a need in the art to determine if administration of exogenous therapeutic protein to a patient will result in production of antigen-specific antibodies which inhibit protein activity in vivo.

SUMMARY OF THE INVENTION

The present invention addresses one or more needs in the art relating to treatment of blood clotting disorders by providing a method for detecting antibodies against exogenously administered human blood clotting polypeptides, fragments variants or analogs thereof. The invention provides transgenic animals expressing human blood clotting factors in place of the endogenous blood clotting factor and methods for detecting antibodies to the human proteins.

In one aspect, the invention provides a transgenic non-human animal having a genome which comprises a polynucleotide sequence encoding a human blood clotting factor selected from the group consisting of Factor VIII (FVIII), Factor VII (FVII), Factor IX (FIX), and von Willebrand Factor (vWF), Factor II (FII), Factor V (FV), Factor X (FX), Factor XI, (FXI), Factor XII (FXII), and Factor XIII (FVIII). In one embodiment, the transgenic animal does not express all or part of a polynucleotide encoding an endogenous blood clotting factor corresponding to the human transgene. In a related embodiment, the transgenic animal does express a polynucleotide encoding an endogenous blood clotting factor corresponding to the human transgene. In one embodiment, the transgenic animal is a non-human animal selected from the group consisting of mouse, rat, rabbit, sheep, hamsters, gerbils, guinea pig, pig, bovine and non-human primate. In one embodiment, the non-human transgenic animal is a mouse.

In one embodiment, the transgenic animal is homozygous for the human transgene. In a further embodiment, the transgenic animal is heterozygous for the human transgene.

In another embodiment, the polynucleotide sequence encoding the blood clotting factor is operably linked to a promoter region. It is contemplated that in a transgenic animal of the invention, the promoter is a liver-specific promoter, a muscle-specific promoter, a pancreatic-specific promoter, a neural-specific promoter, an endothelial cell-specific promoter, a smooth muscle-cell specific promoter, a tyrosinase-specific promoter, a blood clotting factor promoter, or an adipose tissue promoter or an inducible promoter. In a related embodiment, the promoter is selected from the group consisting of an alpha-fetoprotein promoter, an albumin promoter, a CMV promoter, and an endogenous blood clotting factor promoter.

In a further embodiment, the polynucleotide sequence encoding the blood clotting factor further comprises a poly A sequence.

In various aspects, the invention provides a non-human transgenic animal comprising a polynucleotide encoding a human blood clotting factor selected from the group consisting of Factor VIII, Factor VII, Factor IX, von Willebrand Factor, Factor II (FII), Factor V (FV), Factor X (FX), Factor XI, (FXI), Factor XII (FXII), and Factor XIII (FXIII), wherein the human blood clotting factor retains physiological activity of the human blood clotting factor, wherein the transgenic mammal has stably integrated into its genome an exogenous gene construct comprising: (a) transcriptional regulatory polynucleotide sequences, (b) DNA encoding said human blood clotting factor, and (c) a polyadenylation signal, that result in the expression of the DNA encoding the blood clotting factor, wherein (a), (b) and (c) are operably linked in the exogenous gene construct to obtain production of the human blood clotting factor in the transgenic animal. In one embodiment, the transgenic animals docs not express all or part of an endogenous blood clotting factor corresponding to the human transgene. In a further embodiment, the transcriptional regulatory polynucleotide sequences are selected from the group consisting of 5' transcriptional regulatory polynucleotide sequences, 3' transcriptional regulatory polynucleotide sequences, internal transcriptional regulatory polynucleotide sequences, and combinations thereof.

In one embodiment, the 5' regulatory sequence of the exogenous gene construct is a promoter, optionally comprising an enhancer region. In a related aspect, the promoter is a promoter region as described herein.

In a further aspect, it is contemplated that any of the non-human transgenic animals described herein optionally also comprises a polynucleotide encoding a human major histocompatibility (MHC) class II gene in place of a MHC class II gene endogenous to the transgenic non-human animal. In one embodiment, the human MHC class II gene is any HLA gene suitable for expression in a non-human transgenic animal, including but not limited to, HLA-DQ, HLA-DR, HLA-DP, HLA-DO, LMP, TAP and TAPBP. In a related embodiment, a transgenic animal of the invention expressing a human blood clotting factor is made to express a human MHC class II gene by breeding a transgenic mouse expressing a human MHC class II gene with a transgenic animal of the invention expressing a human blood clotting factor. Alternatively, a transgenic animal of the invention expressing a human blood clotting factor is made to express a human MHC class II gene by introducing a polynucleotide sequence encoding an MHC class II gene into the genomic DNA of the non human transgenic animal of the invention. It is contemplated that introducing the transgene is carried out by any methods known in the art. In one embodiment, the introducing is carried out by microinjection or by viral vector.

In a further embodiment, the introducing comprises introducing a polynucleotide sequence encoding an human major histocompatibility class II gene into the genomic DNA of the non-human animal to replace all or part of a major histocompatibility class II gene endogenous to the animal.

In one embodiment, a non-human transgenic animal of the invention expresses a human vWF gene and a human MHC class II gene, and does not express endogenous vWF and MHC class II genes. In a related embodiment, a non-human transgenic animal of the invention expresses a human FVIII gene and a human Class II gene and does not express endogenous FVIII and MHC class II genes. In a further embodiment, a non-human transgenic animal of the invention expresses a human FVII gene and a human Class II gene and does not express endogenous FVII and MHC class II genes. In a still further embodiment, it is contemplated that a non-human transgenic animal of the invention expresses a human FIX gene and a human Class II gene and does not express endogenous FIX and MHC class II genes.

The invention further contemplates a method of producing a transgenic non-human animal expressing a human blood clotting factor selected from the group consisting of FVIII, FVII, FIX, vWF, FII, FV, FX, FXI, FXII, and FXIII in place of an endogenous blood clotting factor, the method comprising introducing a polynucleotide sequence encoding the human blood clotting factor into the genomic DNA of the non-human animal, wherein the transgenic non-human animal comprises a polynucleotide encoding the human blood clotting factor and not a corresponding blood clotting factor endogenous to the transgenic animal. In one embodiment, the introducing is carried out by any methods known in the art. In various aspects, the introducing is carried out by microinjection or by viral vector.

In a related embodiment, in the method of producing a transgenic animal, the nucleotide sequence is operably linked to a promoter region as described herein. It is further contemplated that the promoter is selected from the group consisting of an alpha-fetoprotein promoter, an albumin promoter, a CMV promoter and an endogenous blood clotting factor promoter. In another embodiment, the nucleotide sequence comprises a poly A sequence.

In a further aspect, the invention provides a method for producing a transgenic non-human animal expressing a human blood clotting factor comprising: a) providing a polynucleotide sequence encoding a human blood clotting factor selected from the group consisting of FVIII, FVII, FIX, vWF, FII, FV, FX, FXI, FXII, and FXIII, and a positive selectable marker gene, the marker gene being flanked by loxP sites; b) introducing the polynucleotide sequence into an embryonic stem cell from the same animal species as the non-human animal under conditions such that said polynucleotide sequence is homologously recombined into a genomic locus of said embryonic stem cell to produce an embryonic stem cell containing a polynucleotide encoding a human blood clotting factor selected from the group consisting of FVIII, FVII, FIX, vWF, FII, FV, FX, FXI, FXII, and FXIII and said selectable marker gene; c) injecting the homologously recombined embryonic stem cell into a blastocyst of the non-human animal; d) introducing the injected blastocyst into a pseudo-pregnant female non-human animal; and e) permitting the pseudo-pregnant female animal to deliver one or more transgenic animals containing the homologously recombined DNA sequence, wherein the transgenic mice express the human blood clotting factor selected from the group consisting of FVIII, FVII, FIX, vWF, FII, FV, FX, FXI, FXII, and FXIII. In one embodiment, in step (b) the human transgene polynucleotide sequence is homologously recombined into a genomic locus encoding all or part of at least one naturally-occurring blood clotting factor gene in the genome of the embryonic stem cell.

In one embodiment, the polynucleotide sequence encoding the blood clotting factor of the method above further comprises a promoter operably linked to the human blood clotting factor gene. In a related embodiment, the promoter is selected from the group consisting of an alpha-feto protein promoter, an albumin promoter, a CMV promoter and an endogenous blood clotting factor promoter. In another embodiment, the polynucleotide sequence encoding the blood clotting factor comprises a polyA sequence.

In various aspects it is contemplated that the selectable marker is selected from the group consisting of green fluorescent protein, a neomycin (neo) resistance gene, a puromycin (Puro) resistance gene, a diphtheria toxin resistance gene, hygromycin phosphotransferase, xanthineguanine phosphoribosyl transferase, the Herpes simplex virus type 1 thymidine kinase, adenine phosphoribosyltransferase and hypoxanthine phosphoribosyltransferase. In one embodiment, the selectable marker is a neomycin resistance gene, neo. In another embodiment, the selectable marker is diphtheria toxin.

In a related embodiment, a transgenic animal of the invention is crossed with a Cre-deleter strain of mouse.

In a related aspect, the method of making a transgenic animal further comprises introducing a polynucleotide sequence encoding a human major histocompatibility (MHC) class II gene into the genomic DNA of the non-human animal, said polynucleotide sequence encoding a human major histocompatibility class II gene replacing all or part of a major histocompatibility class II gene endogenous to the transgenic animal such that the transgenic animal does not express its endogenous major histocompatibility class II gene. In one embodiment, the introducing is carried out by any methods known in the art. In a specific embodiment the introducing is carried out by microinjection or by viral vector.

In a still further aspect, the invention contemplates a method for screening for antibodies against a human blood clotting factor in a non-human transgenic comprising a polynucleotide transgene expressing a human blood clotting factor selected from the group consisting of FVIII, FVII, FIX, vWF, FII, FV, FX, FXI, FXII, and FXIII, the method comprising, administering to the animal a composition comprising the human blood clotting factor polypeptide, fragment, analog or variant thereof corresponding to the human transgene encoding the human blood clotting factor expressed in the animal, and detecting antibodies specific for the human blood clotting factor in a test sample from the transgenic animal.

In one embodiment, the detecting step is performed using radioimmunoassay, enzyme linked immunosorbant assay (ELISA), flow cytometry, or magnetic beads. In a specific embodiment, the detecting is performed by ELISA.

In another embodiment, the human blood clotting factor in the composition administered in the screening methods of the invention is modified by chemical linkage to water soluble polymers. In one embodiment, the water soluble polymer is any water soluble known in the art. In a related embodiment, the water soluble polymer is a polyethylene glycol moiety. Further, the chemical linkage, includes, but is not limited to, glycosylation, PEGylation, polysialylation, or addition of a second polypeptide sequence to form a fusion protein. In another embodiment, the human blood clotting factor comprises a polysialyl moiety. In still another specific embodiment, the human blood clotting factor in the composition is a fusion protein, and in various aspects, the fusion protein comprises the human blood clotting factor and a second therapeutic agent. In other aspects, the second agent is a second human blood clotting factor selected from the group consisting of FVII, FVII, FIX, vWF, FII, FV, FX, FXI, FXII, and FXIII.

The invention provides that the test sample in the contemplated screening methods is selected from the group consisting of immune cells and serum. In one embodiment, the sample is serum. In another embodiment, the sample is an immune cell isolated from the transgenic animal.

In another aspect, the invention provides a method for screening for immunogenicity of a human blood clotting factor in a non-human transgenic animal comprising a transgene expressing a human blood clotting factor which is selected from the group consisting of FVIII, FVII, FIX, vWF, FII, FV, FX, FXI, FXII, and FXIII the method comprising, administering to the animal a composition comprising a human blood clotting factor corresponding to the human blood clotting factor expressed by the transgene expressed in the animal, and detecting an immunogenic event in the animal subsequent to the administration of the human blood clotting factor polypeptide.

In various aspects, the immunogenic event is associated with the production of antibodies against the human blood clotting factor. In one embodiment, the immunogenic event is selected from the group consisting of alloantibody production and an allergic reaction.

It is further contemplated that the human blood clotting factor in the composition administered in the screening methods of the invention comprises a fragment, analog or variant of the human blood clotting factor transgene expressed by the animal. In another embodiment, the composition further comprises a pharmaceutically acceptable carrier. In still another embodiment, the composition optionally comprises an adjuvant.

It is contemplated that the administering step is performed intravenously, subcutaneously, intramuscularly, orally, parenterally or via inhalation.

In a further aspect, the invention contemplates a method for determining the effect of a test compound on an human blood clotting factor comprising: administering the test compound to a non-human transgenic animal comprising a transgene expressing a human blood clotting factor selected from the group consisting of FVIII, FVII, FIX, vWF, FII, FV, FX, FXI, FXII, and FXIII, and detecting a change in human blood clotting factor activity in the presence of the compound compared to the activity in the absence of the compound. In various embodiments, the human blood clotting factor activity is selected from the group consisting of expression of the blood clotting factor, blood clotting activity, and protein binding activity. In a related embodiment, the blood clotting factor is vWF and the clotting factor activity is FVIII binding.

In another aspect, the invention provides an experimental animal model that is a non-human transgenic animal expressing at least one human blood clotting factor, wherein the animal does not generate a significant antibody titer against the human blood clotting factor when the (native) blood clotting factor is administered. However, the animal model produces antibodies against the blood clotting factor if the blood clotting factor carries neoantigens or if the blood clotting factor is injected together with impurities that activate the innate immune system. In one embodiment, the animal is susceptible to induction of an acquired blood clotting factor disorder.

In one embodiment, the animal model is an experimental animal model for acquired hemophilia A. Acquired hemophilia A is induced by injecting human FVIII that carries neoantigens or by injecting human FVIII together with ligands for toll-like receptors. In a related embodiment, the animal model is an experimental animal model for acquired hemophilia B.

In a further embodiment, the experimental animal model comprises a human blood clotting factor selected from the group consisting of Factor VIII, Factor VII, Factor IX, von Willebrand Factor, Factor II, Factor V, Factor X, Factor XI, Factor XII and Factor XIII.

In a further aspect, the invention contemplates a method for identifying an agent which induces a break of tolerance to a blood clotting factor (a tolerance-breaking agent), comprising: administering a candidate agent to the transgenic non-human animal as described herein expressing a human blood clotting factor, and lacking a significant anti-blood clotting factor response to the human blood clotting factor, administering the human blood clotting factor for which the animal is transgenic; and, detecting anti-blood clotting factor response in the animal, wherein the candidate agent is a tolerance-breaking agent if the administration of the candidate agent permits production of an anti-blood clotting factor response.

In one embodiment, the anti-blood clotting factor response is production of anti-blood clotting factor inhibitors. In a related embodiment, the response is an immune response. In a further embodiment, the immune response is production of antibodies against the human blood clotting factor.

In certain embodiments, the candidate agent is selected from the group consisting of penicillin, fludarabine, interferon-alpha, a chemotherapeutic agent, an antibiotic, an antipsychotic agent, ligands for toll-like receptors, pro-inflammatory cytokines and any other compound that induces the release of proinflammatory cytokines in vivo.

In one embodiment, the blood clotting factor is selected from the group consisting of Factor VIII, Factor VII, Factor IX, von Willebrand Factor, Factor II, Factor V, Factor X, Factor XI, Factor XII and Factor XIII.

BRIEF DESCRIPTION OF THE FIGURES

FIG. 3 shows the sequence of the vWF insert including leader sequence and start and stop codons (in BOLD) (SEQ ID NO: 16).

DETAILED DESCRIPTION OF THE INVENTION

Figure 1A:
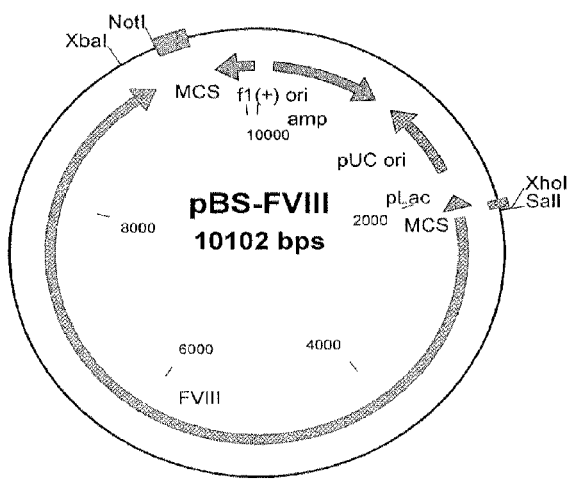
FIGS. 1A and 1B illustrate plasmids comprising a human Factor VIII polynucleotide for insertion into a non-human animal genome.

The present invention addresses the need in the art for improved compositions useful to treat blood clotting disorders, as well as methods to screen for antibodies that may be generated in response to the exogenously administered blood clotting factor compositions. The present invention also provides transgenic animals expressing human blood clotting factors, in some instances in place of a blood clotting factor endogenous to the animal, and optionally one or more human major histocompatibility complex genes, in order to analyze the development of antibodies to human clotting factor therapeutics.

DEFINITIONS

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

As used herein, the following terms have the meanings ascribed to them unless specified otherwise.

As used herein, a "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

As used herein a "gene" refers to a DNA sequence that encodes or a particular sequence of amino acids which comprise all or part of one or more polypeptides, proteins or enzymes, and may or may not include introns, and regulatory DNA sequences, such as promoter or enhancer sequences, 5'-untranslated region, or 3'-untranslated region which affect, for example, the conditions under which the gene is expressed. Some genes, which are not structural genes, may be transcribed from DNA to RNA, but are not translated into an amino acid sequence. Other genes may function as regulators of structural genes or as regulators of DNA transcription.

As used herein a "promoter" or "promoter sequence" is a DNA regulatory region capable of binding RNA polymerase in a cell and initiating transcription of a coding sequence. In one aspect, the promoter sequence is bound at its 3' terminus by a transcription initiation site and extends upstream (5' direction) to include the minimum number of bases or elements necessary to initiate transcription at levels detectable above background. In a related aspect, within the promoter sequence is found a transcription initiation site (conveniently defined for example, by mapping with nuclease S 1), as well as protein binding domains (consensus sequences) responsible for the binding of RNA polymerase. The promoter may be operatively associated with other expression control sequences, including enhancer and repressor sequences.

In one aspect, promoters used to control gene expression include, but are not limited to, cytomegalovirus (CMV) promoter (U.S. Pat. No. 5,385,839 and No. 5,168,062), the SV40 early promoter region (Benoist and Chambon, Nature 290: 304-3101981), the promoter contained in the 3' long terminal repeat of Rous sarcoma virus (Yamamoto, et al., Cell 22:787-797, 1980), the herpes thymidine kinase promoter (Wagner et al., Proc. Natl. Acad. Sci. USA 78:1441-1445, 1981), the regulatory sequences of the metallothionein gene (Brinster et al., Nature 296:39-42, 1982); promoter elements from yeast or other fungi such as the Gal 4 promoter, the ADC (alcoho) dehydrogenase) promoter, PGK (phosphoglycerol kinase) promoter, alkaline phosphatase promoter; and transcriptional control regions that exhibit neuronal or brain specific expression, such as the gonadotropic releasing hormone gene control region which is active in the hypothalamus (Mason et al., Science 234:1372-1378, 1986), the Thy1.2 "pan-neuronal" promoter, and synapsin I promoter (Howland et al., Brain Neurobiol Aging 16: 685-699, (995), active in neurons. It is also contemplated that the promoter is an endogenous blood clotting factor promoter. The worker of ordinary skill in the art will understand that any promoter known in the art is useful, and that the cell type in which expression is desired can dictate use of a particular promoter.

As used herein a coding sequence is "under the control of," "operably linked to" or "operatively associated with" transcriptional and translational control sequences in a cell when RNA polymerase transcribes the coding sequence into RNA, which is then trans-RNA spliced (if it contains introns) and translated, in the case of mRNA, into the protein encoded by the coding sequence.

As used herein the terms "express" and "expression" refer to allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed." An expression product is, in various aspects, characterized as intracellular, extracellular or secreted. The term "intracellular" means inside a cell. The term "extracellular" means outside a cell, such as a transmembrane protein. A substance is "secreted" by a cell if it appears in significant measure outside the cell, from somewhere on or inside the cell.

As used herein "transfection" refers to the introduction of a foreign nucleic acid into a cell. The term "transformation" refers to the introduction of a "foreign" (i.e. exogenous, heterologous, extrinsic or extracellular) gene, DNA or RNA sequence to an embryonic stem (ES) cell or pronucleus, so that the cell will express the introduced gene or sequence to produce a desired substance in a transgenic animal.

As used herein the terms "vector," "cloning vector" and "expression vector" refer to a vehicle by which a DNA or RNA sequence (e.g., a foreign gene) is introduced into a host cell so as to transform the host and promote expression (e.g., transcription and translation) of the introduced sequence. The term "vector" is used herein interchangeably with the term "plasmid."

As used herein "selectable marker" refers to a gene encoding an enzyme or other protein that confers upon the cell or organism in which it is expressed an identifiable phenotypic change such as resistance to a drug, antibiotic or other agent, such that expression or activity of the marker is selected for (for example, but without limitation, a positive marker, such as the neo gene) or against (for example, and without limitation, a negative marker, such as the dipteheria gene). A heterologous selectable marker refers to a selectable marker gene that has been inserted into the genome of an animal in which it would not normally be found.

Examples of selectable markers include, but are not limited to, an antibiotic resistance gene such as neomycin (neo), puromycin (Puro), diphtheria toxin, phosphotransferase, hygromycin phosphotransferase, xanthineguanine phosphoribosyl transferase, the Herpes simplex virus type 1 thymidine kinase, adenine phosphoribosyltransferase and hypoxanthine phosphoribosyltransferase. The worker of ordinary skill in the art will understand any selectable marker known in the art is useful in the method.

As used herein "heterologous" refers to a combination of elements not naturally occurring. For example, heterologous DNA refers to DNA not naturally located in the cell, or in a chromosomal site of the cell. It is contemplated that the heterologous DNA includes a gene foreign to the cell. A heterologous expression regulatory element is such an element operatively associated with a different gene than the one it is operatively associated with in nature.

As used herein, the term "homologous" refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Optimal alignment of sequences for comparison is conducted, for example and without limitation, by the local homology algorithm of Smith & Waterman, Adv. Appl. Math. 2:482, 1981; by the homology alignment algorithm of Needleman & Wunsch, J. Mol. Biol. 48:443, 1970; by the search for similarity method of Pearson & Lipman, Proc. Natl. Acad. Sci. USA 85:2444, 1988; by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). Another example of algorithm that is suitable for determining percent sequence identity and sequence similarity is the BLAST algorithm, which is described in Altschul et al., J. Mol. Biol. 215:403-410, 1990. Software for performing BLAST analyses is publicly available through the National Center for Biotechnology Information. In addition to calculating percent sequence identity, the BLAST algorithm also performs a statistical analysis of the similarity between two sequences (see, e.g., Karlin & Altschul, Proc. Nat'l. Acad. Sci. USA 90:5873-5787, 1993).

As used herein "endogenous" refers to a polypeptide or polynucleotide or other compound that is expressed naturally in the host organism, or originates within a cell, tissue or organism. "Exogenous" refers to a polypeptide, polynucleotide or other compound that originates outside a cell, tissue or organism.

As used herein a "polypeptide" refers to a polymer composed of amino acid residue linked via peptide bonds. Synthetic polypeptides are synthesized, in one aspect, using an automated polypeptide synthesizer. The term "protein" typically refers to large polypeptides. The term "peptide" typically refers to short polypeptides.

As used herein a "fragment" of a polypeptide refers to any portion of the polypeptide smaller than the full-length polypeptide or protein expression product. Fragments are typically deletion analogs of the full-length polypeptide wherein one or more amino acid residues have been removed from the amino terminus and/or the carboxy terminus of the full-length polypeptide. Accordingly, "fragments" are a subset of deletion analogs described below.

As used herein an "analog" refers to a polypeptide substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence. Substitutions are conservative or non-conservative based on the physicochemical or functional relatedness of the amino acid that is being replaced and the amino acid replacing it.

As used herein an "allelic variant" refers to any of two or more polymorphic forms of a gene occupying the same genetic locus. Allelic variations arise naturally through mutation, and may result in phenotypic polymorphism within populations. In certain aspects, gene mutations are silent (no change in the encoded polypeptide) or may encode polypeptides having altered amino acid sequences. "Allelic variants" also refer to cDNAs derived from mRNA transcripts of genetic allelic variants, as well as the proteins encoded by them.

As used herein a "variant" refers to a polypeptide, protein or analog thereof that is modified to comprise additional chemical moieties not normally a part of the molecule. Such moieties, in various aspects, modulate the molecule's solubility, absorption, and/or biological half-life. The moieties in various other aspects, alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art. For example, the variant may be a blood clotting factor having a chemical modification which confers a longer half-life in vivo to the protein. In one embodiment, the polypeptides are modified by addition of a water soluble polymer known in the art. In a related embodiment, polypeptides are modified by glycosylation, PEGylation, and/or polysialylation.

As used herein, "tolerance" refers to the lack of an antigen-recipient's immune response which would otherwise occur, e.g., in response to the introduction of a non-self MHC antigen into the recipient. Tolerance involves, in various aspects, humoral, cellular, or both humoral and cellular responses. Tolerance, as used herein, refers not only to complete immunologic tolerance to an antigen or compound, i.e., no immune response, but also to partial immunologic tolerance, i.e., a limited immune response which does not completely eliminate, inhibit, or otherwise suppress the response to the compound. For instance, in some aspects, a tolerant subject exhibits a detectable immune response to a compound, but it is significantly less than, or decreased compared to, a non-tolerant subject's immune response when exposed to the same compound.

As used herein, "breaking tolerance" or "to break tolerance" refers to an acquired absence of tolerance to an antigen to which the recipient was either naturally tolerant or tolerant via induction through biological means. A subject in which tolerance has been broken responds to the presence of the antigen or compound to which the recipient was previously tolerant, and a response against the antigen or compound is detectable in a subject in whom tolerance is broken. In one aspect, the recipient's response is an immunological response.

A "tolerance-breaking agent" or "an agent to break tolerance" is an agent that, when administered to a recipient, allows for or permits the production of a response to an antigen to which the recipient was either naturally tolerant or tolerant via induction through biological means. Tolerance-breaking agents for a specific antigen include those that permit in the recipient response, e.g., a negative or detrimental response, including without limitation production of an inhibitor to the antigen and/or an anti-antigen immune response, including the production of antibodies, when that antigen is administered to the subject after tolerance is broken, and to which the subject was previously tolerant and exhibited no significant response prior to tolerance breaking.

Candidate tolerance breaking agents are any agents that are tested for the ability to permit induction of an anti-antigen response, e.g., production of an inhibitor and/or anti-antigen antibodies. The candidate agent is found in nature or is synthesized. In various aspects, a candidate agent is selected from a chemical library, a natural product library, or a combinatorial library. Chemical libraries consist of structural analogs of known compounds. Natural product libraries are collections of microorganism, animal, plants or marine organisms or proteins or small molecules isolated therefrom, which are used to create mixtures for screening for candidate agents. Combinatorial libraries are comprised of large numbers of peptides, oligonucleotides or organic compounds. Methods of making or synthesizing a chemical, natural product or combinatorial library are known in the art. Additionally, chemical and combinatorial libraries are commercially available. In certain embodiments, the candidate agent is selected from the group consisting of a chemotherapeutic agent, an antibiotic, an anti-psychotic agent, penicillin, fludarabine, interferon-alpha, ligands for toll-like receptors, pro-inflammatory cytokines and any other compound that induces proinflammatory cytokines in vivo. However, the animal model produces antibodies against the blood clotting factor if the blood clotting factor carries neoantigens.

As used herein a "detectable moiety" or "label" refers to a composition detectable by spectroscopic, photochemical, biochemical, immunochemical, chemical or other means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that is used to quantitate the amount of bound detectable moiety in a sample.

Blood Clotting Factors

Factor VIII (FVIII) is a blood plasma glycoprotein of about 260 kDa molecular mass produced in the liver of mammals. It is a critical component of the cascade of coagulation reactions that lead to blood clotting. Within this cascade is a step in which Factor IXa, in conjunction with FVIII, converts Factor X to an activated form, Factor Xa. FVIII acts as a cofactor at this step, being required with calcium ions and phospholipid for the activity of Factor IXa. The two most common hemophilic disorders are caused by a deficiency of functional FVIII (Hemophilia A, about 80% of all cases) or functional Factor IXa (Hemophilia B or Christmas Factor disease).

Until recently, the standard treatment of Hemophilia A involved frequent infusion of preparations of FVIII concentrates derived from the plasmas of human donors. While this replacement therapy is generally effective, such treatment puts patients at risk for virus-transmissible diseases such as hepatitis and AIDS. Although this risk has been reduced by further purification of FVIII from plasma by immunopurification using monoclonal antibodies, and by inactivating viruses by treatment with either an organic solvent or heat, such preparations have greatly increased the cost of treatment and are not without risk. For these reasons, patients have been treated episodically, rather than prophylactically. A further complication is that about 15% of patients develop inhibitory antibodies to plasma-derived FVIII.

An important advance in the treatment of Hemophilia A has been the isolation of cDNA clones encoding the complete 2,351 amino acid sequence of human FVIII (see, Wood et al, Nature, 312: 330 (1984) and U.S. Pat. No. 4,757,006, Jul. 12, 1988) and the provision of the human FVIII gene DNA sequence and recombinant methods for its production. However, patients receiving recombinant FVIII may still develop FVIII-specific antibodies which interfere with treatment of the disease. Factor VIII products for the treatment of hemophilia include, but are not limited to: ADVATE® (Antihemophilic Factor (Recombinant), Plasma/Albumin-Free Method, rAHF-PFM), recombinant Antihemophilic Factor (BIOCLATE™, GENARC®, HELIXATE FS®, KOATE®, KOGENATE FS®, RECOMBINATE®): MONOCLATE-P®, purified preparation of Factor VIII:C, Antihemophilic Factor/von Willebrand Factor Complex (Human) HUMATE-P® and ALPHANATE®, Anti-hemophilic Factor/von Willebrand Factor Complex (Human); and HYATE C®, purified pig Factor VIII.

von Willebrand Factor exists in plasma in a series of multimer forms of a molecular weight of from $1 \times 10^6$ to $20 \times 10^6$ Dalton. vWF is a glycoprotein primarily formed in the endothelial cells of mammals and subsequently secreted into circulation. In this connection, starting from a polypeptide chain having a molecular weight of approximately 220 kD, a vWF dimer having a molecular weight of 550 kD is produced in the cells by the formation of several sulfur bonds. Further polymers of the vWF with increasing molecular weights, up to 20 million Dalton, are formed from the vWF dimers by linking. It is presumed that particularly the high-molecular vWF multimers have an essential importance in blood coagulation.

vWF syndrome manifests clinically when there is either an underproduction or an overproduction of vWF. Overproduction of vWF causes increased thrombosis (formation of a clot or thrombus inside a blood vessel, obstructing the flow of blood) while reduced levels of, or lack of, high-molecular forms of vWF causes increased bleeding and an increased bleeding time due to inhibition of platelet aggregation and wound closure.

A vWF deficiency may also cause a phenotypic hemophilia A since vWF is an essential component of functional factor VIII. In these instances, the half-life of Factor VIII is reduced to such an extent that its function in the blood coagulation cascade is impaired. Patients suffering from von Willebrand disease (vWD) or vWF syndrome frequently exhibit a Factor VIII deficiency. In these patients, the reduced Factor VIII activity is not the consequence of a defect of the X chromosomal gene, but an indirect consequence of the quantitative and qualitative change of vWF in plasma. The differentiation between hemophilia A and vWD may normally be effected by measuring the vWF antigen or by determining the ristocetin-cofactor activity. Both the vWF antigen content and the ristocetin cofactor activity are lowered in most vWD patients, whereas they are normal in hemophilia A patients. vWF products for the treatment of vWF syndrome include, but are not limited to: HUMATE-P; and, IMMUNATE®, INNOBRAND®, and 8Y®, which therapies comprising FVIII/VWF concentrate from plasma.

Factor VII (proconvertin), a serine protease enzyme, is one of the central proteins in the blood coagulation cascade. The main role of Factor VII (FVII) is to initiate the process of coagulation in conjunction with tissue factor (TF). Upon vessel injury, TF is exposed to the blood and circulating Factor VII. Once bound to TF, FVII is activated to FVIIa by different proteases, among which are thrombin (Factor IIa), activated Factor X and the FVIIa-TF complex itself. Recombinant human Factor VIIa (NOVOSEVEN®) has been introduced for use in uncontrollable bleeding in hemophilia patients who have developed inhibitors against replacement coagulation factor. Transgenic organisms expressing human Factor VII have been developed by Hwang et al., (Mar Biotechnol 6:485-92, 2004), which describe transgenic fish expressing human FVII.

Factor IX (FIX, Christmas Factor) is a serine protease that is inactive unless activated by Factor XIa or Factor VIIa (of the tissue factor pathway). When activated into Factor IXa, it acts by hydrolyzing an arginine-isoleucine bond in Factor X to form Factor Xa. Factor VIII is a required cofactor for FIX protease activity (Lowe G D, Br. J. Haematol. 115: 507-13, 2002). Deficiency of Factor IX causes hemophilia B or Christmas disease. Transgenic animals expressing human Factor IX have been disclosed. See for example Schnieke et al., (Science 278:2130-33, 1997), which discloses transgenic sheep expressing human Factor IX in sheep's milk, and Alexander et al., (Hum Mol Genet. 4:993-9, 1995), which discloses expression of human FIX in transgenic mice. Also, Bigger et al., (Gene Ther. 2006 13(2):117-26, 2006) disclose administration of hematopoietic stem cells expressing human Factor IX in a mouse model of hemophilia B which induces tolerance to the protein for up to a year in some animals. Waddington et al., (Blood. 2003 101:1359-66), disclose in utero administration of an adenoviral vector expressing human FIX to mice in order to induce tolerance to human protein in recipient animals.

Additional blood factors amendable to use methods of the invention include without limitation Factor II (as know in the art as thrombin) (Genbank Accession No. NP_000497), deficiencies of which cause thrombosis and dysprothrombinemia; Factor V, (Genbank Accession No. NP_000121), deficiencies of which cause hemorrhagic diathesis or a form of thrombophilia, which is known as activated protein C resistance, Factor XI (Genbank Accession No. NP_000119), deficiencies of which cause Rosenthal's syndrome (hemophilia C), and Factor XIII subunit A (Genbank Accession No. NP_000120) and subunit B (Genbank Accession No. NP_001985), deficiencies of which are characterized as a type I deficiency (deficiency in both the A and B subunits) and type II deficiency (deficiency in the A subunit alone), either of which can result in a lifelong bleeding tendency, defective wound healing, and habitual abortion Factor XII (Genbank Accession No. NP_000496); protein C (Genbank Accession No. NP_000303); antithrombin III (Genbank Accession No. NP_000479), and activated forms thereof.

Fragments, Variants and Analogs of Human Blood Clotting Factors

In order to assess the therapeutic efficacy of a human blood clotting factor protein in the treatment of a blood clotting disorder, the human blood clotting factor polypeptide or a fragment, variant or analog thereof, is administered to a transgenic mouse described herein.

Methods for preparing polypeptide fragments, variants or analogs are well-known in the art. Fragments of a polypeptide are prepared using, without limitation, including enzymatic cleavage (e.g., trypsin, chymotrypsin) and also using recombinant means to generate a polypeptide fragments having a specific amino acid sequence. Using a polynucleotide encoding a desired fragment, polypeptide fragments may be generated comprising a region of the protein having a particular activity, such as a ligand binding domain, a receptor binding domain, a dimerization or multimerization domain, or any other identifiable domain known in the art.

Methods of making polypeptide analogs are also well-known. Amino acid sequence analogs of a polypeptide are substitutional, insertional or deletion variants. Deletion analogs, including fragments of a polypeptide, lack one or more residues of the native protein which are not essential for function or immunogenic activity. Insertional analogs involve the addition of material at a non-terminal point in the polypeptide. This may include the insertion of an immunoreactive epitope or simply a single residue.

Analogs may be substantially homologous or substantially identical to the blood clotting factors from which they are derived and described herein. Contemplated analogs are those which retain at least some of the biological activity of the wild-type polypeptide, e.g. blood clotting activity.

Substitutional analogs typically exchange one amino acid of the wild-type for another at one or more sites within the protein, and may be designed to modulate one or more properties of the polypeptide, as described herein, without the loss of other functions or properties. In one aspect, substitutions are conservative substitutions. By "conservative amino acid substitution" is meant substitution of an amino acid with an amino acid having a side chain of a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine).

Polynucleotides encoding fragments and analogs may be readily generated by a worker of skill to encode biologically active fragments, variants, or analogs of the naturally-occurring molecule that possess the same or similar biological activity to the naturally-occurring molecule. This may be done by PCR techniques, digestion of DNA encoding molecule, and the like. Thus, one of skill in the art will be able to generate single base changes in the DNA strand to result in an altered codon and a missense mutation.

Exemplary blood clotting factor analogs are described, for example, in U.S. Pat. No. 6,346,513, U.S. Pat. No. 6,316,226, U.S. Pat. No. 6,156,888, U.S. Pat. No. 6,130,203, and U.S. Pat. No. 6,958,322, herein incorporated by reference.

Human blood clotting factor variants contemplated include polypeptides chemically modified by such techniques as ubiquitination, glycosylation, conjugation to therapeutic or diagnostic agents, labeling (e.g., with radionuclides or various enzymes), covalent polymer attachment such as PEGylation (derivatization with polyethylene glycol), introduction of non-hydrolyzable bonds, and insertion or substitution by chemical synthesis of amino acids such as ornithine, which do not normally occur in human proteins. Variants retain the binding properties of non-modified molecules of the invention.

Preparing PEGylated blood clotting factor analogs will generally comprise the steps of (a) reacting the polypeptide with polyethylene glycol (such as a reactive ester or aldehyde derivative of PEG) under conditions whereby the binding construct polypeptide becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-PEGylated product. In some embodiments, the binding construct will have a single PEG moiety at the N-terminus.

Polyethylene glycol (PEG) may be attached to the blood clotting factor to provide a longer half-life in vivo. The PEG group may be of any convenient molecular weight and may be linear or branched. The average molecular weight of the PEG ranges from about 2 kiloDalton ("kD") to about 100 kDa, from about 5 kDa to about 50 kDa, or from about 5 kDa to about 10 kDa. The PEG groups are attached to the blood clotting factor via acylation or reductive alkylation through a natural or engineered reactive group on the PEG moiety (e.g., an aldehyde, amino, thiol, or ester group) to a reactive group on the blood clotting factor (e.g., an aldehyde, amino, or ester group) or by any other technique known in the art.

Polypeptide variants useful in the methods of the present invention include polypeptide comprising polysialylate (PSA) moieties. Methods for preparing polysialylated polypeptide are described in United States Patent Publication 20060160948 and Saenko et al., Haemophilia 12:42-51, 2006.

It is further contemplated that the human blood clotting factor for use in the methods of the invention may be a fusion protein with a second agent which is a polypeptide. In one embodiment, the second agent which is a polypeptide, without limitation, is an enzyme, a growth factor, a cytokine, a chemokine, a cell-surface receptor, the extracellular domain of a cell surface receptor, a cell adhesion molecule, or fragment or active domain of a protein described above. In a related embodiment, the second agent is a blood clotting factor such as Factor VIII, Factor VII, Factor IX and von Willebrand factor. The fusion protein contemplated is made by chemical or recombinant techniques well-known in the art.

Blood Clotting Factor Compositions for Administration

To administer blood clotting factor polypeptides (including fragments, analogs or variants) described herein to test subjects, blood clotting factor polypeptides are formulated in a composition comprising one or more pharmaceutically acceptable carriers. The phrase "pharmaceutically or pharmacologically acceptable" refers to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

In addition, compounds may form solvates with water or common organic solvents. Such solvates are contemplated as well.

The blood clotting factor compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Formulation of the pharmaceutical composition will vary according to the route of administration selected (e.g., solution, emulsion). An appropriate composition comprising the composition to be administered is prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

Pharmaceutical compositions useful in the methods of the present invention containing a blood clotting factor as an active ingredient may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention.

A variety of aqueous carriers, e.g., water, buffered water, 0.4% saline, 0.3% glycine, or aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

In some embodiments, the blood clotting factor compositions are lyophilized for storage and reconstituted in a suitable carrier prior to use. This technique has been shown to be effective with conventional immunoglobulins. Any suitable lyophilization and reconstitution techniques known in the art are employed. It is appreciated by those skilled in the art that lyophilization and reconstitution leads to varying degrees of antibody activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

In certain embodiments, the concentration of blood clotting factor in these formulations varies widely, for example from less than about 0.5%, usually at or at least about 1% to as much as 15 or 20% by weight and will be selected primarily based on fluid volumes, viscosities, etc., in accordance with the particular mode of administration selected. Thus, for example, and without limitation, a typical pharmaceutical composition for parenteral injection is made up to contain 1 ml sterile buffered water, and 50 mg of blood clotting factor. A typical composition for intravenous infusion could be made up to contain 250 ml of sterile Ringers solution, and 150 mg of blood clotting factor. Actual methods for preparing parenterally administrable compositions are known or apparent to those skilled in the art and are described in more detail in, for example, Remington's Pharmaceutical Science, 15th ed., Mack Publishing Company, Easton, Pa. (1980). An effective dosage of bispecific antibody is within the range of 0.01 mg to 1000 mg per kg of body weight per administration.

In various aspects, the pharmaceutical compositions are in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In some embodiments, the carrier is a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity is maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms is brought about by various antibacterial and antifungal agents, for example, parabens, chlorobutanol, phenol, sorbic acid, thimerosal, and the like. In many cases, it will be desirable to include isotonic agents, for example, sugars or sodium chloride. In certain aspects, prolonged absorption of the injectable compositions is brought about by the use in the compositions of agents delaying absorption, for example, aluminum monostearate and gelatin.

Compositions useful for administration may be formulated with uptake or absorption enhancers to increase their efficacy. Such enhancers, include, for example, salicylate, glycocholate/linoleate, glycholate, aprotinin, bacitracin, SDS, caprate and the like. See, e.g., Fix (J. Pharm. Sci., 85:1282-1285, 1996) and Oliyai and Stella (Ann. Rev. Pharmacol. Toxicol., 32:521-544, 1993).

In addition, the properties of hydrophilicity and hydrophobicity of the compositions contemplated for use in the methods or the invention are well balanced, thereby enhancing their utility for both in vitro and especially in vivo uses, while other compositions lacking such balance are of substantially less utility. Specifically, compositions contemplated for use in the invention have an appropriate degree of solubility in aqueous media which permits absorption and bioavailability, in the body, while also having a degree of solubility in lipids which permits the compounds to traverse the cell membrane to a putative site of action.

Transgenic Animal Preparation

In general, transgenic animals of the invention include any transformable species except humans. Of particular interest are mammals, including known transformable species such as mouse, rat, rabbit, sheep, hamsters, gerbils, guinea pig, and pig, and others, as transformation methods are developed, including bovine and non-human primates.

The transgenic animals of the invention are genetically modified animals in which at least one foreign gene has been inserted into the genome. These animals allow regulatory processes on the cellular level to be examined and influenced in a systematic and specific manner not achievable with other test systems. Transgenic animals of the type described are useful for analyzing in vivo effects of administration of therapeutic blood clotting factors, including but not limited to Factor VIII (FVIII), Factor VII (FVII), Factor IX (FIX), von Willebrand Factor (vWF), Factor II (FII), Factor V (FV), Factor X (FX), Factor XI, (FXI), Factor XII (FXII), and Factor XIII (FXIII). The transgenic animals serve as excellent models for evaluating the effect of compounds, i.e., purified clotting proteins or variants thereof, on causing the development of anti-self antibodies in context of a putative tolerant host immune system. Such understanding is essential to the design and testing of agents for treatment of blood clotting disorders including, but not limited to, hemophilia, von Willebrand syndrome, and the like.

It is further contemplated that, in certain aspects, transgenic animals expressing human blood clotting factors also express human major histocompatibility complex (MHC) genes. MHC genes are involved in expressing foreign antigen on the cell surface and presenting antigen to either CD8+ (MHC class I) or CD4+ (MHC class II) T cells. Both human MHC class I transgenic mice (Escobar et al., Clin Exp Immunol. 116:214-9, 1999) and human MHC class II transgenic mice (WO 2006/056769 and Fugger et al., Proc. Natl. Acad. Sci. USA. 91, 6151-6155, 1994) have been described in the art, the disclosures of which are hereby incorporated by reference.

The human MHC class II gene includes, any human leukocyte antigen (HLA) gene suitable for expression in a non-human transgenic animal, including but not limited to, HLA-DQ, HLA-DR, HLA-DP-, HLA-DO, LMP, TAP and TAPBP (the MHC Consortium, Nature 401:921-923, 1999, herein incorporated by reference).

The transgenes herein comprise a coding sequence (e.g., cDNA, a synthetic coding sequence, or genomic DNA) for an human blood clotting factor or an human MHC class II gene protein flanked by natural regulatory (expression control) sequences, or associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The coding sequence may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides contain, in certain aspects, one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, in some embodiments, the polynucleotides herein are modified with a label capable of providing a detectable signal, either directly or indirectly. Exemplary labels include radioisotopes, fluorescent molecules, biotin, and the like.

The control of gene expression is accomplished by a variety of means well-known in the art. Expression of a transgene is constitutive or regulated to be inducible or repressible by known means, typically by choosing a promoter that is responsive to a given set of conditions, e.g., presence of a given compound, or a specified substance, or change in an environmental condition such as tissue type or temperature. The term "inducible expression" extends to any means for causing gene expression to take place under defined conditions, the choice of means and conditions being chosen on the basis of convenience and appropriateness for the host organism.

Transformation is carried out by a variety of known techniques, depending on the organism, on characteristics of the organism's cells and of its biology. Stable transformation involves DNA entry into cells and into the cell nucleus. For organisms that are regenerated from single cells (which includes some mammals), transformation is carried out in in vitro culture, followed by selection for transformants and regeneration of the transformants. Methods often used for transferring DNA or RNA into cells include micro-injection, particle gun bombardment, forming DNA or RNA complexes with cationic lipids, liposomes or other carrier materials, electroporation, and incorporating transforming DNA or RNA into virus vectors. Other techniques are known in the art. DNA transfer into the cell nucleus occurs by cellular processes, and can sometimes be aided by choice of an appropriate vector, by including integration site sequences which are acted upon by an intracellular transposase or recombinase (see e.g., [Craig, Ann. Rev. Genet. 1988, 22:77; Cox. In Genetic Recombination (R. Kucherlapati and G. R. Smith, eds.) 1988, American Society for Microbiology, Washington, D.C., pages 429-493; Hoess. In Nucleic Acid and Molecular Biology (F. Eckstein and D. M. J. Lilley eds.) Vol. 4, 1990, Springer-Verlag, Berlin, pages 99-109.

The genetic background of mouse strains from which the various ES cells are derived are known in the art, including ES cells originating from mouse strain 129: R1 cells originate from a mouse blastocyst from a cross between the sub-strains 129/Sv and 129/Sv-CP (Nagy et al., Proc Natl Acad Sci USA. 90:8424-8, 1993); GS1 cells originate from 129/Sv/Ev. D3-cells (Doetschman et al., Nature 330:576-8, 1987) and J1 cells originate from 129/Sv or 129/terSv. TT2 cells which also yielded ES mice originated from an F1 hybrid strain (C57BL/6×CBA) (Yagi et al., Anal Biochem. 14:70-6, 1993).

Expression vectors and nucleic acids used to express a blood clotting factor in some aspect also contain a tissue-specific promoter. Such promoters are known in the art and include, but are not limited to liver-specific promoters (e.g., albumin; Miyatake et al., J. Virol. 1:5124-32, 1997; α-feto-protein), muscle-specific promoters (e.g., myosin light chain 1 (Shi et al., Hum Gene Ther. 8:403-10, 1997, α-actin), pan-creatic-specific promoter (e.g., insulin or glucagon promoters), neural-specific promoters (e.g., the tyrosine hydroxylase promoter or the neuron-specific enolase promoter), endothelial cell-specific promoters (e.g., von Willebrand factor; Ozaki et al., Hum Gene Ther. 7:1483-90, 1996), and smooth muscle-cells specific promoters (e.g., 22a; Kim et al., J Clin Invest. 100:1006-14, 1997). Other tissue specific promoters include promoters are also being used in developing cancer therapies, including tyrosinase-specific promoters (Diaz et al., J. Virol. 72:789-95, 1998), an adipose tissue promoter derived from human aromatase cytochrome p450 (p450arom) (see U.S. Pat. No. 5,446,143; Mahendroo et al., J. Biol. Chem. 268:19463 19470, 1993; and Simpson et al., Clin. Chem. 39:317 324, 1993). It is further contemplated that the promoter is an endogenous blood clotting factor promoter. The vectors and other nucleic acid molecules useful in the methods of the invention can also include sequences that limit the temporal expression of the transgene. For example, the transgene is controlled by drug inducible promoters by, for example including cAMP response element enhancers in a promoter and treating the transfected or infected cell with a cAMP modulating drug (Suzuki et al., Hum Gene Ther. 7:1883-93, 1996). Alternatively, repressor elements can prevent transcription in the presence of the drug (Hu et al., Cancer Res 57:3339-43, 1997). Spatial control of expression has also been achieved by using ionizing radiation (radiotherapy) in conjunction with the erg1 gene promoter (Seung et al., Cancer Res 55:5561-5, 1995).

The recombinant nucleic acid constructs encoding human blood clotting factors or human MHC class genes may be inserted into any suitable plasmid, bacteriophage, or viral vector for amplification, and may thereby be propagated using methods known in the art, such as those described in Molecular Cloning A Laboratory Manual, 2nd Ed., ed. by Sambrook, Fritsch and Maniatis (Cold Spring Harbor Laboratory Press: 1989). In one embodiment, expression vectors compatible with eukaryotic cells, such as vertebrate cells, are used. Eukaryotic cell expression vectors are well known in the art and are available from commercial sources. Contemplated expression vectors contain both prokaryotic sequences (to facilitate the propagation of the vector in bacteria), and one or more eukaryotic transcription units that are functional in swine cells. Typically, such vectors provide convenient restriction sites for insertion of the desired recombinant DNA molecule. The pcDNAI, pSV2, pSVK, pMSG, pSVL, pPVV-1/PML2d and pTDT1 (ATCC No. 31255) derived vectors are examples of mammalian expression vectors suitable for transfection of non-human cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) are used for expression of proteins in swine cells. The various methods employed in the preparation of the plasmids and the transformation of host cells are well known in the art. For other suitable expression systems for useful in the present invention, as well as general recombinant procedures, see Molecular Cloning A Laboratory Manual, 2nd Ed., ed. by Sambrook, Fritsch and Maniatis (Cold Spring Harbor Laboratory Press: 1989).

Techniques for creating a transgenic animal, particularly a mouse or rat are well known (Gordon, International Review of Cytology 115:171-229, 1989). Various approaches to introducing transgenes are available, including microinjection of nucleic acids into cells, retrovirus vector methods, and gene transfer into embryonic stem (ES) cells. If fertilized oocytes are used for generating a transgenic, desired foreign DNA or transgene is incorporated into the oocytes. Incorporation of the transgene into the oocyte is carried out by several methods such as via an appropriate retroviral vector, or by microinjection. Transgenic mice are generated routinely in the art by microinjection of DNA into blastocysts isolated from pregnant mice, as described in U.S. Pat. No. 4,736,866 issued to Leder et al., and as provided by B. Hogan et al. entitled "Manipulating the Mouse Embryo: A Laboratory Manual", Cold Spring Harbor Laboratory, Cold Spring Harbor, N.Y., U.S.A. (1986). See also, e.g., Haren et al, Annu. Rev. Microbiol. 53:245-281, 1999; Reznikoff et al., Biochem. Biophys. Res. Commun., 266(3):729-734, 1999; Ivies et al, Methods Cell Bid., 60:99-131, 1999; Han et al., FEMS Microbiol. Rev. 21:157-178 1997. U.S. Pat. No. 6,492,575 describes a method to of making transgenic mice by transforming ES cells and inject the transformed cells into a tetraplid blastocyst. By interbreeding heterozygous siblings, homozygous animals carrying the desired gene are obtained.

Additionally, Capecchi et al. describe a method by which transgenes are incorporated into embryonic, fetal or adult pluripotent stem cells (Science 244:1288-1292, 1991). In this method, embryonic stem cells are isolated from blastocysts cultivated in vitro. These embryonic stem cells are kept stable in culture over many cell generations without differentiation. The transgene is then incorporated into the embryonic stem cells by electroporation or other methods of transformation. Stem cells carrying the transgene are selected for and injected into the inner cell mass of blastocysts. The blastocysts are then implanted into pseudopregnant females. Since not all the cells of the inner cell mass of the blastocysts carry the transgenes, the animals are chimeric with respect to the transgenes. Crossbreeding of the chimeric animals allows for the production of animals which carry the transgene. An overview of the process is provided by Capecchi, Trends in Genetics 1989, 5:70-76.

Delivery of the transgene may be accomplished by a retroviral delivery system, see e.g., Eglitis et al., Adv. Exp. Med. Biol. 241:19, 1988. In one aspect, a retroviral construct is one in which the structural genes of the virus are replaced by a single gene which is then transcribed under the control of regulatory elements contained in the viral long terminal repeat (LTR). A variety of single-gene-vector backbones have been used, including the Moloney murine leukemia virus (MoMuLV). In one embodiment, retroviral vectors which permit multiple insertions of different genes such as a gene for a selectable marker and a second gene of interest, under the control of an internal promoter are derived from this type of backbone, see e.g., Gilboa, Adv. Exp. Med Biol. 241:29, 1988.

The elements of the construction of vectors for the expression of a protein product are known to those skilled in the art. Efficient expression from retroviral vectors is observed when "strong" promoters are used to control transcription, such as the SV 40 promoter or LTR promoters, reviewed in Chang et al., Int. J. Cell Cloning 7:264, 1989. These promoters are constitutive and do not generally permit tissue-specific expression. Other suitable promoters are discussed herein.

The use of packaging cell lines can increase the efficiency and the infectivity of the produced recombinant virions, see Miller, 1990, Human Gene Therapy 1:5. Murine retroviral vectors have been useful for transferring genes efficiently into murine embryonic, see e.g., Wagner et al., 1985, EMBO J. 4:663; Griedley et al., Trends Genet. 3:162, 1987, and hematopoietic stem cells, see e.g., Lemischka et al., Cell 45:917-927, 1986; Dick et al., Trends in Genetics 2:165-170, 1986.

An additional retroviral technology which permits attainment of much higher viral titers than were previously possible involves amplification by consecutive transfer between ecotropic and amphotropic packaging cell lines, the so-called "ping-pong" method, see e.g., Kozak et al., J. Virol. 64:3500-3508, 1990; Bodine et al., Prog. Clin. Biol. Res. 319: 589-600, 1989. In addition, a techniques for increasing viral titers permit the use of virus-containing supernatants rather than direct incubation with virus-producing cell lines to attain efficient transduction, see e.g., Bodine et al., Prog. Clin. Biol. Res. 319:589-600, 1989. Because replication of cellular DNA is required for integration of retroviral vectors into the host genome, it may be desirable to increase the frequency at which target stem cells which are actively cycling e.g., by inducing target cells to divide by treatment in vitro with growth factors, see e.g., Lemischka et al., Cell 45:917-927, 1986; Bodine et al., Proc. Natl. Acad. Sci. 86:8897-8901, 1989, or to expose the recipient to 5-fluorouracil, see e.g., Mori et al., Jpn. J. Clin. Oncol. 14 Suppl. 1:457-463, 1984.

Its contemplated, in some embodiments, that the during the introduction of the transgene into the animal, the transgene is inserted into the endogenous gene, thereby knocking-out function of the endogenous gene. In other embodiments, the exogenous gene is inserted into the animal genome in a location such that the expression of the endogenous gene is preserved. Thus, the transgenic animal may express all or part of the endogenous polynucleotide that corresponds to the human transgene polynucleotide inserted into the animal.

Methods of Detecting an Immunogenic Event

U.S. Pat. Nos. 5,470,560 and 5,670,134 describe a method to detect immunogenicity of proteins using a transgenic mammal containing a DNA sequence encoding the polypeptide of interest, which is heterologous to the transgenic mammal, and to which the animal is tolerant because it is perceived as an endogenous gene. A preparation comprising a polypeptide similar to or identical to the expressed transgene is administered to the tolerant animals and the development of antibodies specific for the polypeptide is determined using radioimmunoassays or ELISA systems. Unlike the system described in U.S. Pat. Nos. 5,470,560 and 5,670,134, the transgenic animals described herein, in some embodiments, express the human protein in place of the endogenous gene.

It is contemplated that the transgenic animals useful for identifying antibodies specific for the human blood clotting factor transgene express the human blood clotting factor at levels similar to normal expression of the endogenous protein in a control animal, and are tolerant to the protein encoded by the human transgene, i.e., are incapable of making a strong immune response to the protein when the protein is administered exogenously.

Transgenic animals that are tolerant to the heterologous polypeptide are contacted with a preparation comprising the human blood clotting factor to be analyzed in any fashion calculated to induce an immune response in a non-tolerant animal. In one embodiment, the host animal is contacted with the heterologous polypeptide using the same route of administration, carriers and frequency of administration intended for the preparation in its in vivo therapeutic or diagnostic setting for human patients. If the dose, route and schedule of injection and buffer have not been established in patients, then these parameters are derived from pre-clinical animal studies or from in vitro experiments. In the case of therapeutic proteins or polypeptides this may be by parenteral, intramuscular or subcutaneous administration in a pharmacologically-acceptable isotonic carrier such as saline, 5% dextrose, or phosphate buffer. Immunostimulants or adjuvants or neoantigens are optionally included in the preparation. Multiple administrations of the therapeutic or diagnostic dose are also evaluated. In one embodiment, the preparation contains the heterologous polypeptide encoded by the transgene. In another embodiment, the preparation contains a fragment, variant or analog of the heterologous blood factor polypeptide encoded by the human transgene.

In one instance, it may be desired to determine the immunogenicity of a polypeptide fragment, variant or analog having such desired characteristics as greater solubility or stability, resistance to enzyme digestion, improved biological half-life, and other features known to those skilled in the art. In this case the DNA used for transfection to generate the transgenic animal encodes the native primary amino acid sequence of the heterologous polypeptide, while the test preparation contains a heterologous polypeptide having a structure which is a fragment, analog or variant of the native heterologous polypeptide.

In a further embodiment, the preparation contains a therapeutic or diagnostic agent that is expected to interact in vivo with the heterologous polypeptide encoded by the human transgene to produce an immunogenic or toxic response in the animal. For example, the preparation for administration may comprise the heterologous protein fused to another therapeutic agent, wherein the agent may be a polypeptide, a chemical moiety, or other therapeutic agent known in the art.

The immunogenicity of the test preparation optionally is compared to the immunogenicity of any native and/or denatured forms of proteins present in the preparation. These forms of the protein are negative and positive controls, respectively. The protein is denatured for the positive controls by various procedures known to those skilled in the art, such as heating at 100° C. for 1-2 minutes or treatment with denaturing agents such as sodium dodecyl sulfate, 7M guanidine chloride or 8M urea. The positive control will establish whether the transgenic animals have the immune repertoire to respond to the protein treated to ensure that it is conformationally non-native. An additional immunogenicity positive control is performed by combining the native test protein with an adjuvant to enhance the immune response in the transgenic host. Another positive control is to use the polypeptide from a third source, e.g., bovine growth hormone, Chinese hamster tPA or pig Factor VIII. In certain embodiments, the adjuvant is any that is known to enhance the immunogenicity of the test protein in particular, or that are generally used to enhance the immunogenicity of proteins. Two commonly used techniques are to emulsify the protein in aqueous buffer with an equal volume of Freund's complete (FA) (for the first injection) or incomplete adjuvant (for later injections) or to co-precipitate the protein from solution using alum. The mixture of adjuvant and protein is then injected subcutaneously or intramuscularly into the transgenic animals. Although the injection schedule can be varied, two injections at 2 week intervals would be commonly used to test the immunogenicity of a protein. The doses tested may range from 1 to 1000 µg per injection, including 1, 2, 5, 10, 15, 20, 50, 100, 150, 200, 250, 300, 50, 400, 450, 500, 550, 600, 650, 700, 750, 800, 850, 900, 950 and 1000 µg per injection.

The detecting agent in the immunoassay may be linked to a detectable moiety or a label. Detectable moiety or label refers to a composition detectable by spectroscopic, photochemical, biochemical, immunochemical, or chemical means. The detectable moiety often generates a measurable signal, such as a radioactive, chromogenic, or fluorescent signal, that is used to quantitate the amount of bound detectable moiety in a sample. In some embodiments, the detectable moiety is incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety is directly or indirectly detectable. Indirect detection can involve the binding of a second directly or indirectly detectable moiety to the detectable moiety. For example, without limitation, the detectable moiety is the ligand of a binding partner, such as biotin, which is a binding partner for streptavadin, or a nucleotide sequence, which is the binding partner for a complementary nucleotide sequence, to which it can specifically hybridize. The binding partner may itself be directly detectable, for example, an antibody may be itself labeled with a fluorescent molecule. In related embodiments, the binding partner also is indirectly detectable, for example, a nucleic acid having a complementary nucleotide sequence is a part of a branched DNA molecule that is in turn detectable through hybridization with other labeled nucleic acid molecules. (See, e.g., P D. Fahrlander and A. Klausner, Bio/Technology 6:1165, 1988). Quantitation of the signal is achieved by, e.g., scintillation counting, densitometry, or flow cytometry.

Examples of labels suitable for use in the immunogenic assay methods of the invention include, radioactive labels (e.g., $^{32}P$, $^{35}S$) fluorophores (e.g., fluorescein), electron-dense reagents, enzymes (e.g., as commonly used in an ELISA), biotin, digoxigenin, or haptens as well as proteins which are made detectable, e.g., by incorporating a radiolabel into the hapten or peptide, or used to detect antibodies specifically reactive with the hapten or peptide. Also contemplated are proteins for which antisera or monoclonal antibodies are available, or nucleic acid molecules with a sequence complementary to a target, a nanotag, a molecular mass bead, a magnetic agent, a nano- or micro-bead containing a fluorescent dye, a quantum dot, a quantum bead, a fluorescent protein, dendrimers with a fluorescent label, a micro-transponder, an electron donor molecule or molecular structure, or a light reflecting particle.

Additional labels contemplated for use with present invention include, but are not limited to, fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold, colored glass or plastic beads (e.g., polystyrene, polypropylene, latex, etc.), and luminescent or chemiluminescent labels (e.g., Europium (Eu), MSD Sulfo-Tag).

The label may be coupled directly or indirectly to the desired component of the assay according to methods well known in the art. In one embodiment, the label is covalently bound to the component using an isocyanate or N-hydroxysuccinimide ester reagent for conjugation of an active agent useful in the invention. In one aspect of the invention, bifunctional isocyanate reagents are used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels are used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently hound to the molecule. The ligand then hinds to another molecules (e.g., streptavidin) molecule, which is either inherently detectable or covalently bound to a signal system, such as a detectable enzyme, a fluorescent compound, or a chemiluminescent compound.

The compounds useful in the method of the invention, are, in certain aspects, conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds suitable for use as labels include, but are not limited to, those listed above as well as fluorescein derivatives, rhodamine and its derivatives, dansyl, umbelliferone, eosin, TRITC-amine, quinine, fluorescein W, acridine yellow, lissamine rhodamine, B sulfonyl chloride erythroscein, ruthenium (tris, bipyridinium), europium, Texas Red, nicotinamide adenine dinucleotide, flavin adenine dinucleotide, etc. Chemiluminescent compounds suitable for use as labels include, but are not limited to, MSD Sulfa-TAG, Europium (Eu), Samarium (Sm), luciferin and 2,3-dihydrophthalazinediones, e.g., luminol. For a review of various labeling or signal producing systems that are useful in the methods of the present invention, see U.S. Pat. No. 4,391,904.

Means for detecting labels are well known to those of skill in the art. Thus, for example, where the label is radioactive, means for detection include a scintillation counter (e.g., radioimmunoassay, scintillation proximity assay) (Pitas et al., Drug Metab Dispos. 34:906-12, 2006) or photographic film, as in autoradiography. Where the label is a fluorescent label, it may be detected by exciting the fluorochrome with the appropriate wavelength of light and detecting the resulting fluorescence (e.g., ELISA, flow cytometry, or other methods known in the art). The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands are used in the diagnosis of a disease or health condition.

In one embodiment the labeled compositions useful in the methods of the invention are linked to a solid support, including but not limited to, filters, plates or membranes. It is further contemplated that the labeled compounds may be labeled and interact in solution. For example, the capture antibody may be labeled with a fluorescent resonance energy transfer (FRET) donor molecule and the target molecule is labeled with a FRET acceptor molecule such that the molecules are in proximity when binding occurs. Alternatively, the target molecule may be labeled with the FRET donor and the antibody molecule the FRET acceptor. Another possibility is to separate quenching and fluorescent molecule both present on the antibody or target when target and antibody hybridize. The target molecule is only close enough for its label to emit if it is interacting with the reagent. This produces a system where the molecule only emits when it interacts with the reagent (direct monitoring). A narrow band pass filter is used to block all wavelengths except that of the molecule's label. FRET molecule pairs are commercially available in the art (e.g., from Invitrogen, Carlsbad, Calif.), and may be used according to the manufacturer's protocol. FRET emissions are detected using optical imaging techniques, such as a CCD camera.

Another method of detecting antibody-antigen interactions is to label it with an electron donor. This donor label would give electrons to an electrical contact to which the reagent is bound. See, for example, Ghindilis, A. (Biochem Soc Trans. 28:84-9, 2000) and Dai et al. (Cancer Detect Prev. 29:233-40, 2005) which describe enzymes useful in and methods for electro immunoassays. The electron contact would then be read by an A to D (analog to digital) converter and quantified. The higher the electron count the more interactions took place.

One embodiment of a label capable of single molecule detection is the use of plasmon-resonant particles (PRPs) as optical reporters, as described in Schultz et al., *Proc. Nat'l Acad. Sci.*, 97:996-1001 (2000), incorporated herein by reference. PRPs are metallic nanoparticles, typically 40-100 nm in diameter, which scatter light elastically with remarkable efficiency because of a collective resonance of the conduction electrons in the metal (i.e., the surface plasmon resonance). The magnitude, peak wavelength, and spectral bandwidth of the plasmon resonance associated with a nanoparticle are dependent on the particle's size, shape, and material composition, as well as the local environment. By influencing these parameters during preparation, PRPs are formed that have scattering peak anywhere in the visible range of the spectrum. For spherical PRPs, both the peak scattering wavelength and scattering efficiency increase with larger radius, providing a means for producing differently colored labels. Populations of silver spheres, for example, are reproducibly prepared for which the peak scattering wavelength is within a few nanometers of the targeted wavelength, by adjusting the final radius of the spheres during preparation. Because PRPs are bright, yet nanosized, they are used as indicators for single-molecule detection; that is, the presence of a bound PRP in a field of view can indicate a single binding event.

In another exemplary embodiment, the device is a test strip for use in the rapid detection of a blood clotting factor, using immunoassay methods in which a blood clotting factor in a fluid sample competes with an immobilized blood clotting factor for limited labeled antibody binding sites. In the assay procedure, the body fluid sample mixes with labeled antibody-dye conjugate and migrates along a porous membrane. When the concentration of a blood clotting factor is below the detection limit of the test, unbound antibody-dye conjugate binds to a blood clotting factor receptor conjugate immobilized on the membrane, producing a color band in the "negative" test zone. Conversely, when the blood clotting factor level is at or above the detection limit, free blood clotting factor competes with the immobilized blood clotting factor conjugate on the membrane by binding to antibody-dye conjugate, forming an antigen-antibody complex, and thus preventing the development of a color band. Regardless of the blood clotting factor levels in the sample, a color band is produced in each control zone, which serves as a quality control measures that verifies that the reagents are chemically active.

Antigen-antibody complexes are also detected using nanoparticle-derived techniques. See, for example, Ao et al. (Anal Chem. 78:1104-6, 2006) which describes gold nanoparticle quenching, Chen et al., (Biomaterials 27:2113-21, 2006) which describes SiO(2)/Au nanoparticle surfaces in antibody detection, and Lieu et al. (J Immunol Methods. 307:34-40, 2005), which describes silicon dioxide nanoparticles containing dibromofluorescein for use in solid substrate-room temperature phosphorescence immunoassay (SS-RTP-IA).

For the methods of the invention, the antibody or blood clotting factor may be hound to a variety of solid supports, including but not limited to filters, PVC membranes, PDVF membranes, PVC plates and other plates which bind protein, microcarriers, macro solid phase beads, magnetic beads, made out of for example, polystyrene, nanoparticles, such as bimetallic silver-gold nanoparticles (Yan Cui et al., J. Phys. Chem. B, 110:4002-06, 2006), and polyamide membrane (PAM) sheets (Sun et al, Analytical Letters 34:1627-37, 2001)

For example, microspheres with multiple fluorescent molecular fillings, different materials, surface texture, surface patterns, etc. are utilized as identification tags. It is contemplated that either the capture antibody or the lysosomal enzyme is covalently bound to the bead and reacted against the opposite binding partner to assay the amount of lysosomal enzyme-specific antibody in serum. See, for example, Current Protocols in Immunology, Unit 6.11). Fluorescently filled microspheres are currently available from Molecular Probes, Inc. and other companies. Microspheres as small as 20 nm diameter polystyrene beads are currently available.

The blood clotting factor or antibodies are attached to the solid support using standard protocols in the art, e.g., as described by the manufacturer of the support, or using standard chemical crosslinking techniques known in the art. See e.g., Pierce Biotechnology, Inc. (Rockford, Ill.) crosslinking kits.

Candidate Agents

Candidate agents useful in the methods of the invention to identify a tolerance breaking agent are available in the art. It is contemplated that candidate agents useful in the present invention are any organic or inorganic molecule, complex or substance. Exemplary candidate agents are obtained from a chemical library, a natural substance library or a combinatorial library.

In one embodiment, agents are obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Anticancer Drug Des., 12:145, 1997). Such libraries may either be prepared by one of skill in the art (see e.g., U.S. Pat. Nos. 4,528,266 and 4,359,535, and Patent Cooperation Treaty Publication Nos. WO 92/15679, WO 92/15677, WO 90/07862, WO 90/02809, or purchased from commercially available sources (e.g., New England Biolabs Ph.D.™. Phage Display Peptide Library Kit).

In one embodiment of the invention organic molecules are selected from either a chemical library, wherein chemicals are assayed individually, or from combinatorial chemical libraries where multiple compounds are assayed at once, then deconvoluted to determine and isolate the most active compounds.

Numerous chemical libraries exist in the art, e.g., as proprietary libraries of pharmaceutical companies, and compounds in such libraries are suitable candidate agents. Representative examples of such combinatorial chemical libraries include those described by Agrafiotis et al., "System and method of automatically generating chemical compounds with desired properties," U.S. Pat. No. 5,463,564; Armstrong, R. W., "Synthesis of combinatorial arrays of organic compounds through the use of multiple component combinatorial array syntheses," WO 95/02566; Baldwin, J. J. et al., "Sulfonamide derivatives and their use," WO 95/24186; Baldwin, J. J. et al., "Combinatorial dihydrobenzopyran library," WO 95130642; Brenner, S., "New kit for preparing combinatorial libraries," WO 95/16918; Chenera, B. et al., "Preparation of library of resin-bound aromatic carbocyclic compounds," WO 95/16712; Ellman, J. A., "Solid phase and combinatorial synthesis of benzodiazepine compounds on a solid support," U.S. Pat. No. 5,288,514; Felder, E. et al., "Novel combinatorial compound libraries," WO 95/16209; Lerner, R. et al., "Encoded combinatorial chemical libraries," WO 93/20242; Pavia, M. R et al., "A method for preparing and selecting pharmaceutically useful non-peptide compounds from a structurally diverse universal library," WO 95/04277; Summerton, J. E. and D. D. Weller, "Morpholino-subunit combinatorial library and method," U.S. Pat. No. 5,506,337; Holmes, C., "Methods for the Solid Phase Synthesis of Thiazolidinones, Metathiaza ones, and Derivatives thereof," WO 96/00148; Phillips, G. B. and G. P. Wei, "Solid-phase Synthesis of Benzimidazoles," Tet. Letters 37:4887 90, 1996; Ruhland, B. et al., "Solid-supported Combinatorial Synthesis of Structurally Diverse .beta.-Lactams," J. Amer. Chem. Soc. 111:253 4, 1996; Look, G. C. et al., "The Identification of Cyclooxygenase-1 Inhibitors from 4-Thiazolidinone Combinatorial Libraries," Bioorg and Med Chem. Letters 6:707 12, 1996.

Candidate agents of the invention include fusion proteins, polypeptides, peptidomimetics, prodrugs, receptors, binding agents, ribozymes, small molecules, peptides, antibodies, or other drugs which are screened for the ability to modulate tolerance to blood clotting factor proteins. Exemplary candidate agents include, but are not limited to, penicillin, fludarabine, interferon-alpha, a chemotherapeutic agent, an antibiotic, an anti-psychotic agent, a ligand for toll-like receptors, a pro-inflammatory cytokine and any other compound that induces the release of proinflammatory cytokines in vivo.

Ligands for toll-like receptors are described for example, in Jin et al., Immunity 29:182-91, 2008 and Wales et al., Expert Rev Vaccines. 6:971-80, 2007.

A candidate agent is considered a tolerance breaking agent if the presence of anti-blood clotting factor inhibitors is detected using any of the immunologic assays as described above or other inhibitor assay, such as the Bethesda Unit scale assay, upon administration of the human blood clotting factor to the transgenic animal.

Kits

Kits are also contemplated within the scope of the invention. A typical kit can comprise a first antibody that specifically binds to a human blood clotting factor, optionally linked to a detectable label, and a blood clotting factor standard containing a known quantity of a blood clotting factor. Other components may optionally include reagents for carrying out an immunoassay such as a second antibody linked to a detectable label that either binds to a blood clotting factor or to the first antibody; if the label is an enzyme, the kit may also include a substrate from which the enzyme releases a detectable signal.

Additional aspects and details of the invention will be apparent from the following examples, which are intended to be illustrative rather than limiting.

EXAMPLES

Example 1

Human Factor VIII Knock-In Transgenic Mice

In order to study the in vivo effects of inhibitors of Factor VIII (FVIII) on FVIII activity, mice which express human FVIII [Genbank Accession Nos. NM_000132 (isoform a precursor), NM_019863 (isoform b precursor)] in place of the murine gene were developed.

For FVIII knock-in mice, a plasmid containing a full-length cDNA of human FVIII was created using the pBlue-FVIII vector (#307, FIG. 1A). FVIII cDNA (7.2 kB) was cut from pBlue-FVIII #307 plasmid via Xho1/Not1 restriction enzymes denatured and the FVIII insert purified using a gene extraction kit (Qiagen, Valencia, Calif.) using the manufacturers protocol. The FVIII insert was then inserted into either a pCMV-Sport6 vector (Gibco BRL) (FIG. 1) or a liver specific expression vector pBS-Alb/aFeto (Kellendonk et al., Genesis 126:151-53, 2000).

For cloning into the pCMV-Sport6 vector, the vector was cut with restriction enzymes Sal1/Not1, dephosphorylated using APEX™ (heat liable alkaline phosphotase from Epicentre, Madison, Wis.) and denatured followed by agarose gel electrophoresis. Fragments of 4.4 kb and 21 bp were obtained. The vector fragments were cleaned with gel extraction kit (Qiagen). The prepared FVIII insert was ligated into pCMV-Sport6 vector using LIGATE-IT™ ligation kit (USB, Cleveland, Ohio) and the plasmid was transformed into OMNIMAX2™-T1r bacterial cells (Invitrogen, Carlsbad, Calif.). Clones were grown in LB medium and the plasmids isolated by miniprep (Qiagen). Ten clones were then analyzed by enzymatic digestions using Xho1 or Kpn1 restriction enzymes followed by agarose gel electrophoresis. Correct clones were then isolated using midipreps (Qiagen). From the generated pCMV-Sport6-FVIII sense (11.6 kb) the insert was cut with Sal1/Xho1/pvu1 enzymes. Fragments of 7.2 and 4.4 kb were obtained. The 7.2 kb fragment (FVIII insert) was extracted from agarose gel and cleaned with gel extraction kit (Qiagen).

Figure 1B:
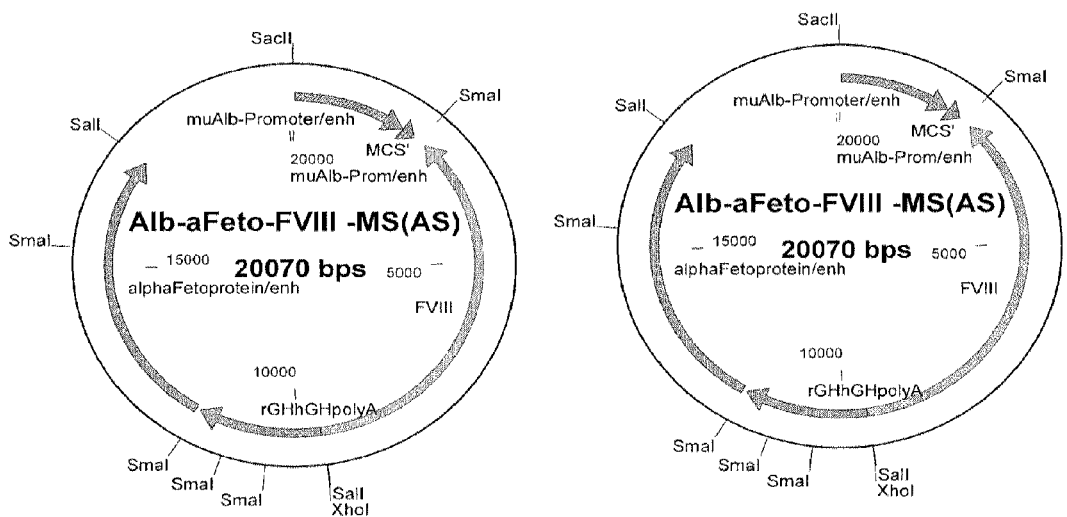

The cleaned FVIII insert from the pCMV-Sport6-FVIII vector was ligated using T4 Ligase (Fermentas, Ontario, Canada) into the prepared target vector pBS-Alb/aFeto (FIG. 1B). The material was transformed into OMNIMAX2™-T1R bacterial cells (Invitrogen). Clones were grown in LB Medium and minipreps were done to isolate plasmid. The clones were examined by restriction with Xho1 and SacII/Xba1, Not1, Pvu1 and SexA1 enzymes followed by agarose gel electrophoresis. Sense and antisense clones (20.1 kb) were obtained. Next, one clone of pBS-Alb/aFeto-FVIII sense plasmid was grown in LB Medium and then isolated using a Giaprep protocol (Qiagen). The plasmid was examined by digestion with Xba1, SacII/Xba1, Not1 and BglII enzymes followed by agarose gel electrophoresis. Sequence analysis was performed by VBC Biotech Service GmbH (Austria).

For the generation of the transgenic mice the plasmid above was linearized with Xho1 restriction enzyme and delivered in Tris buffer (50 mM Tris-HCl (pH8.5), 10 mM MgCl2, 50 mM NaCl). The plasmid was microinjected into the male pronucleus of fertilized oocytes obtained from either E17 hemophilic mice (E17ko deletion on a C57BL/6J background) or from wildtype C57BL/6.1 mice according to Rülicke et al. (Exp Physiol 85: 589-601, 2000).

Positive clones are selected for injection into blastocyt and generation of chimeric cells. Blastocysts are isolated from pregnant C57BL/6J females. The positive human FVIII-containing ES clones are injected into the blastocysts and the injected blastocysts are re-implanted into OF1 pseudo-pregnant females. The presence of the ES cells is assessed initially using coat color markers. The chimeras are then bred with C57Bl/6 strains to populate the F1 generation.

Example 2

Human vWF Knock-In Transgenic Animals

Von Willebrand Factor (vWF) [Genbank Accession No. NM_000552] is required for the normal adhesion of platelets to the subendothelium for primary hemostasis, and is involved in stabilizing Factor VIII. vWF is synthesized in endothelial cells as pre-pro-vWF and processed intracellularly to propeptide and mature vWF. vWF disease is a common inherited bleeding disorder having a large number of subtypes that share a common characteristic, all involve a defect in pro-vWF. A mouse model for vWF disease has been generated using a knock-out strategy (Denis et al., Proc Natl Acad Sci. USA 95:9524-29, 1998), which mimics severe human vWF disease (type III). Injection of recombinant human vWF in vwf in knock-out mice stabilizes FVIII suggesting the human protein can function normally in murine host. In order to generate an animal model tolerant to the human vWF protein that allows for the evaluation of vWF compounds for administration to human patients, a humanized mouse model for vWF was developed, wherein the murine vWF is replaced by human vWF.

Figure 2A:
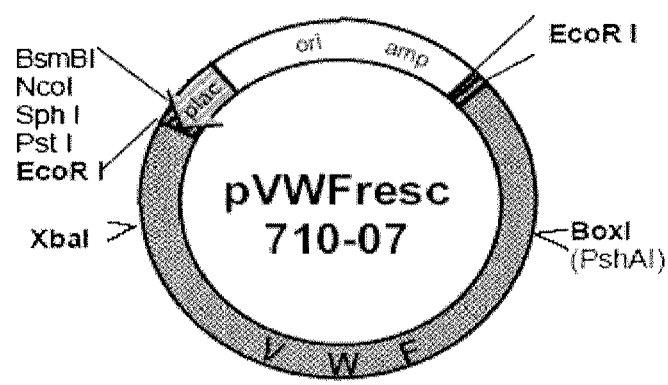
FIGS. 2A and 2B illustrate plasmids comprising a human vWF polynucleotide for insertion into a non-human animal genome.
Figure 2B:
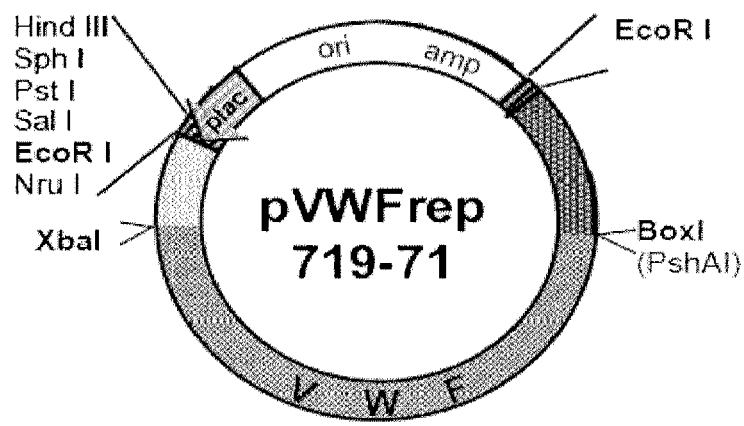

The mouse vWF gene is located on chromosome 6 and extends over 154.1 kB. The gene comprises 57 exons separated by 56 introns. For inserting the human gene, it was determined that the human gene would be inserted into the first coding regions of the mouse gene, at exons 6 and 7. In order to begin the protocol, it was first necessary to clone the homologous sequences in the mice that were to be the insertion points of the human gene (FIG. 3). Three independent clones were generated: (1) an approximate 3.6 kb fragment containing 5' sequences between exons 4 and 5, used to generate the distal part of the 5' long homology win of the targeting vector, LAdi; (2) an approximate 4.7 kb fragment containing the exon 5 and neighboring intronic sequences, used to generate proximal part of the 5' long homology arm, LApr; (3) an approximate 3.8 kb fragment located downstream of exon 6 and used to generate the 3' short homology arm of the targeting vector, $SA_{max}$, and for the positive control vector. FIGS. 2A and 2B show representative vectors for cloning the human vWF gene into transgenic animals.

To generate the vwf clones, DNA amplifications were performed on genomic 129/Sv Pas ES cell DNA using the primers in Table 1, at the following conditions: 94° C. 2 min for one cycle, and 15-20 cycles of 94° C. for 30 seconds, 65° C. for 30 seconds and 68° C. for 7 minutes. The PCR products were subcloned into the pCR4-TOPO vector (Invitrogen) via TA-cloning. TA-cloning takes advantage of the terminal transferase activity of the DNA polymerases (Taq) and adds a single, 3'-A overhang to each end of the PCR product. This makes it possible to clone this PCR product directly into a linearized cloning vector with single, 3'-T overhangs. The resulting plasmids were designated TOPO-LAdi, TOPO-LApr (or TOPOP-LApr-mod) and TOPO-SA-T1.

TABLE 1

| Subclone name | Primer name | Primer sequence 5'-3' | Expected PCR size |
|---|---|---|---|
| LAdi | A1 | ACTATGCCTGCGGCTCTTGATGG (SEQ ID NO: 1) | 3607 BP |
|  | B1 | TCGTGGTCTCTCTGTGTTCACAGCC (SEQ ID NO: 2) |  |
| LApr | C1 | TGTGCAGGCTGTTGAGTGGCTAAGG (SEQ ID NO: 3) | 4662 BP |
|  | D1 | CCATCACATGGTACAATCGTGTGCTACC (SEQ ID NO: 4) |  |
| SA | E1 | TTCTGAGAATGTGGAGGGCAGTGG (SEQ ID NO: 5) | 3775 BP |
|  | F1 | TCCACCTAGAGAAGGAGCCTGTGTAAGG (SEQ ID NO: 6) |  |

The targeting vector (1-HR) containing the human vwf gene was generated comprising: a homology regions isogenic with the 129 SV/PAS ES cell line genome; the replacement of the coding region of mouse vwf with human vwf gene; a positive selection neomycin gene flanked by LoxP recombination site; and, the Diptheria Toxin (DTA) negative selection marker. For the humanized vwf vector, the selection cassette was excised by transfection of the targeting vector into Cre-expressing bacteria.

In order to generate the targeting vector, first a synthetic fragment script-Tg linker containing the human vWF sequence from the KpnI-MluI-HpaI-MfeI restrictions together with a 242-bp Tg 3' part synthesis (from EcoR'V to EcoRI excluded), and the BstBI-EcoRI-Sac1 restriction sites is generated [script-Tg linker, (SEQ ID NO: 7)]

```
GGTACCGGACGCGTGTTAACCAATTGCCGATATCCACTACTGCCAGGGCAAATGTGCCAGCAAAGCCATGTACTC

CATTGACATCAACGATGTGCAGGACCAGTGCTCCTGCTGCTCTCCGACACGGACGGAGCCCATGCAGGTGGCCCT

GCACTGCACCAATGGCTCTGTTGTGTACCATGAGGTTCTCAATGCCATGGAGTGCAAATGCTCCCCCAGGAAGTG

CAGCAAGTGAGGCTGCTGCAGCTGCATGGGTGCCTGCTGCTGCCGGCTTCGAATCGAATTCTGGAGCTC-.
```

These sites allow subsequent cloning steps to be performed exclusively using cohesive ligations, thus securing the efficiency and speed of the construction steps. The introduced sites also facilitate the validation of homologous recombination and recombinase excision events using Southern blot analysis and provide unique linearization sites for the targeting vector.

Next a larger linker fragment GA1-linker is developed comprising the Pac1-Pmel-Hpal restriction sites together with the LAdi 3' synthesis from EcoRI to NheI), a LA 3' part synthesis 3' end from NsiI to intron 5 and the Mlu1-Mfel-BsiW1-SnaB1-Avrl1-Nru1-Ascl restriction sites, which results in the 906 bp GA1 linker fragment [GA1 linker, ATTAATTAAGTTTAAACGAGTTAACTA-GAATTCTGGCTTTATTAATCTCTGTTCT-TCACATTCTTCCATGCACTT TTCTCTOAACTCTGA-CAAATACGAGAACCTTAAAATACTCTGCGATTGTC ACTGCCCTTTGTGCCTACTGTCTAG TTCTCTGGCTC-CACCTTGTTCTCCTTTT-TACGTCTTTTTCTTGAAACCGTACCG-TAAGCATTGCCCATCTTCCTG CCTCAGCCCCCTGTTTATTTATTACTT-TAACTTTTTAATTTCTCACTATTACTOT-TATTGTOTTATGAAGTCACT GCCTGTTCACATTTAC-CTCATAACTACCAAATTCTCTGTTGATTTTTTTTT TTTTTTTGAGACAGGGTTTCTCT GTGTAGCCCTG-GCTGTCCTGGAACTCACTOTGTAGAC-CACGCTGGCCTCAAACTCAGAGATCCGC-CTGCCTCTGC CTCCCGAGTGCTGGGATTAAAGGCAT-GCGCCACCACTGCCAGGCCTOTCTGT-TGCTTTTTATTTCTAGCATTTTC TCTCTGGGTT-TAACTTCCTTCTTCCTGAAGAACCTTCTTTAGCA GTCCATTCAGCAAGGCAGGGGATGGCAAGCT CATCTTTTTCTGGCAAGAGAAGATGGC-CCTAACTCTGAATGATGACTTAGT-TCTGGGAACTAGTTACTACCCCCT CTTCCACAG-CACTCAGACCTAACTCATCTGAGACCGATCTCTG TGACTATOTGCAGGCTCTTGAGTCOCTAAGGA AACAGTCCTGGCTACCACATGCAT-TGATGGTAGCTTGTCCTTCCCAC-CTCTCTGGACGGTGAGAACCAGCTCATT TCCTTTT-TATTTTATTTTATTTTGCAGACGCGTTGCAATTGC GTACGCTTACGTAGTCCTAGGAATCGCGATTGG CGCGCC (SEQ ID NO: 8)]. Next a sequence comprising the SwaI, Eco4711 and Bsu361 restriction sites of the mouse vwf as inserted into the G2 vector (GenOway, Lyon, F R) containing a neo selection cassette. This vector is referred to as the G2-mod vector.

To generate positive control vectors, a 2306 bp HpaI/EcoRE LAdi fragment isolated from the TOPOLadi-T4 plasmid was ligated into the GA1 vector resulting in the LAdi vector (6061 bp). To insert the transgene, a 8268 bp EcoRI/EcoRV fragment isolated from the 1-cDNA plasmid was ligated into the script-Tg vector using MfeI/EcoRV (the plasmid is referred to as the 1-Tg vector). A polyA sequence (632 bp ClaI/EcoRI isolated from G136) was inserted into the 1-Tg vector at the BstI/EcoRI site (1-TG-pA vector).

Next a 4255 bp NheI/NsiI fragment from the TOPO-LApr plasmid was ligated into the LAdi vector (1-LA vector). To insert the neo short arm fragment, a 3672 bp SmaI/NheI fragment from the SA-C+ plasmid was ligated into the 1-LA vector (1-SA vector). To insert the transgene, a 9155 bp MluI/EcoRI fragment from the 1-Tg-pA plasmid was inserted into the 1-LA vector, creating the 1-LA-C+ vector). To insert the long homology mill into the targeting vector, a 15314 bp PmeI/BsiWI fragment isolated from LA-C+ vector was inserted into the 1-SA vector. This is one version of the final targeting vector referred to as the 1-LSA vector. To insert the diphtheria toxin negative selection marker a 19013 AscI/PmeI fragment isolated from 1-LSA vector is inserted into the G141 plasmid (GenOway) resulting in the final targeting vector 1-HR.

The SA-C+ vector referred to above was created as a short homology arm positive control by ligating a 3258 bp Bsu361/DraI fragment isolated form the TOPO-SA-T1 plasmid into the G2-mod vector cut using Bsu361/Eco47III.

PCR screening and Southern blot analysis confirmed the excision events as well as the identification of positive cloning in the ES cells. Southern blot was performed using the following conditions: hybridization in 4×SSC, 1% SDS, 0.5% skimmed milk, 20 mM EDTA, 65° C., 18 hours; wash 2 times in 3×SSC, 1% SDS 65 C for 15 minutes then 2×0.5× SSC, 1% SDS at 65 C for 1 minute.

For insertion into ES cells, the 1-HR vector was linearized by Nru1 and purified by phenol/cholorform extraction and ethanol precipitation. 129 Sv/PAS ES cells were transfected with the linearized 1-HR vector by electroporation ($5 \times 10^6$ ES cells, 40 µg linearized plasmid, 260 V, 500 µF) and grown in G418 selection media (200 µg/ml G418). G418 resistant clones were isolated and amplified in 96-well plates. Positive clones were screened for recombination events by PCR (94° C. 2 minutes, 1 cycle; 94° C. 30 seconds, 65° C. 30 seconds, 68° C. 5 minutes, 35 cycles; 68° C. 8 minutes, one cycle) using the primers GX1406 5'-CTACTTCCATTTGT-CACGTCCTGCACG-3' (SEQ ID NO: 9) and GX6310 5'-CAGCTCCTGCCTTGTTACTGTGACCC-3' (SEQ ID NO: 10), leading to a fragment of 2872 bp.

Additional Southern blot analysis using a 5' homologous recombination strategy detected the presence of the correct wild-type (6865 bp) and recombination events (14897 bp) in the positive clones. Southern blot analysis using 3' homologous recombination strategy results in wild type fragments of 9470 bp and recombination event fragments of 11080 bp. The hybridization also confirmed that no additional randomly integrated copies of the DNA were carried by the ES cells.

Four positive clones were selected for injection into blastocyt and generation of chimeric cells. Blastocysts were isolated from pregnant C57BL/6J females. The positive human vwf-containing ES clones were injected into the blastocysts and the injected blastocysts were re-implanted into OF1 pseudo-pregnant females. The presence of the ES cells was assessed initially using coat color markers. Chimeras were generated at a range of 50% to 80%. The chimeras will next be bred with C57Bl/6 and Cre-deleter strains to populate the F1 generation.

In vivo recombination events may be monitored as above by Southern blot analysis. For inducing the recombination event in vivo and production of the humanized vwf allele, the targeted animals carrying the transgene are bred with Cre-recombinase expressing "deleter" mice (See for example, Tang et al., Genesis 32:199-202, 2002; Jorgez et al., Genesis 44:183-8, 2006).

Example 3

Human Factor VII Knock-In Transgenic Animals

Factor VII [Genbank Accession Nos. NM_000131 (isoform a precursor), NM_019616 (isoform b precursor)] is a significant molecule in the clotting cascade and defects in factor VII result in bleeding disorders and reduced ability to stimulate the coagulation pathway (Osterud B., Blood Coagul Fibrinolysis 1:175-81, 1990). Congenital defects in FVII have been treated with plasma-derived and recombinant EVII (Bauer K., Haemostasis 26 Suppl 1:155-8, 1996).

To create a humanized transgenic mouse expressing the human Factor VII gene, a pB4-EVII vector containing the factor VII cDNA was digested by EcoRI to extract the cDNA. The FVII cDNA was ligated into a pBS-Alb/αFeto vector containing the albumin specific promoter. The pBS-Alb/αFeto vector was first prepared by XhoI restriction digest and then dephosphorylated using calf intestinal phosphatase (CIP) treatment. After Klenow treatment, the FVII cDNA was ligated into the pBS-Alb/αFeto vector using Quick Ligase (Ozyme, France). Recombinant clones were verified by restriction digest and agarose gel analysis.

The pBS-Alb/αFeto vector was digested by NotI to extract the FVII transgene for insertion into a GATEWAY® pENTRY vector. The pENTRY vector containing an albumin promoter, a poly A sequence and the αFetoprotein enhancer was first digested with DraI and EcoRV and dephosphorylated with CIP treatment as above. After Klenow treatment, the FVII cDNA was ligated into the pENTRY vector using Quick ligase and clone insertion confirmed using PCR and gel analysis.

Figure 4:
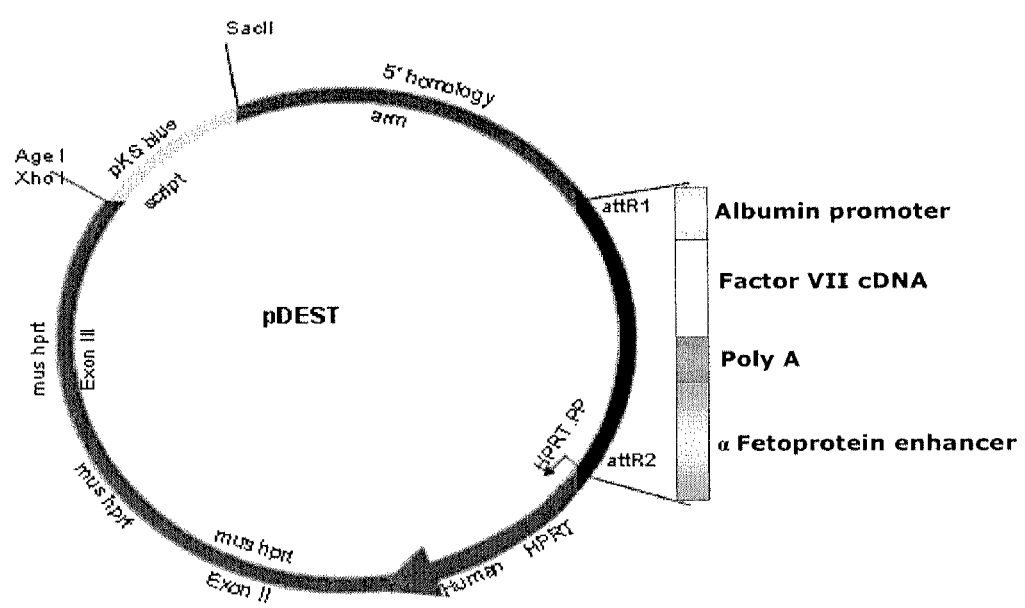
FIG. 4 illustrates a vector containing the human Factor VII gene.

The FVII cDNA was then removed from the pENTRY vector and inserted into the GATEWAY® pDEST™ vector (Invitrogen, Carlsbad, Calif.) which contains part of the human HPRT gene. The transgene was inserted by homologous recombination between attR1 and attR2 recombination sites on the pENTRY and pDEST plasmids (FIG. 4). Recombination events and clone insertion was analyzed by restriction analysis. The resulting vector was linearized by PvuI, phenol/chloroform extracted and electroporated into ES cells.

The ES cells used are BPES cells which exhibit a hybrid background based on the murine C57Bl/6 and 129 genomes. The EVII transgene is inserted at the hprt docking site of the ES cell. The positive clones, which still express a functional hprt gene, are then selected in HAT (hypoxanthine, aminopterin, thymidine) media. The loss of HPRT expression renders the cells sensitive for growth in HAT culture media. Positive clones are then microinjected into blastocysts as described above.

Example 4

Double Transgenic Mice Expressing Human Blood Clotting Factor and Human MHC Genes While transgenic mice expressing human proteins are useful to determine the potential immunogenicity of the human protein when administered as a therapeutic to a tolerant animal, another method to measure the immunogenicity of an exogenously administered protein is to assess the immunogenicity of the protein in the context of the human immune system. In order to stimulate the production of autoantibodies, the exogenous peptide must be presented to T cells in the context of the natural MHC proteins. During a typical immune response, an exogenous antigen is taken up by antigen presenting cells expressing MHC class I or class II molecules, the antigen is processed in the cytoplasm into its antigenic epitope fragments, and the peptide epitopes are presented on the surface of the antigen presenting cell in the pocket of the MHC class I or class II molecule. Binding of a cognate T cell receptor on the surface of T cell to an MHCII-antigen complex activates a cascade of events that may lead to antibody production.

In order to determine which peptides of the human blood clotting factors are antigenic in the context of the human environment, the transgenic non-human mammal expressing a human blood clotting factor may be modified to express human MHC genes. Typically, in the case of an exogenous protein administered that is not a microbiological protein, the protein will be taken up and presented by MHC class II proteins. Therefore, to determine the immunogenicity of a human blood clotting factor in the context of the human immune system. Tg animals described above are further modified to express the human MHC class II genes in place of the native class II genes.

Transgenic mice lacking endogenous class II proteins are known in the art. Sec, for example, Madsen et al., Proc. Natl. Acad. Sci USA 96:10338-343, 1999, which describes a generation of a Tg mouse lacking all endogenous MHCII genes using targeted disruption of the endogenous genes. Additionally, mice expressing human MHC class II genes are known in the art. See for example, Fugger et al., Proc. Natl. Acad. Sci. USA. 91, 6151-6155, 1994, which describes mice expressing the human DR4 gene and human CD4 protein; and Cheng et al., Journal of Autoimmunity 21:195-199, 2003, and Madsen et al., Nature Genetics 23:343-47, 1999, both of which describe Tg mice expressing human MHCII DR and DQ proteins.

In a first method, the transgenic animal expressing a human blood clotting factor is crossed with a transgenic non-human mammal of the same species expressing human major histocompatibility (MHC) genes. The double transgenic animals may be made by crossing a transgenic animal expressing the human blood clotting factor with a second animal expressing the human MHC class II genes, such that the offspring will express both transgenes. For example, a transgenic human vWF mouse (Tg-hu vWF), Tg-hu FVIII, Tg-hu FVII, Tg-hu FIX mouse or mouse expressing a different human blood clotting factor is crossed with a Tg mouse expressing human MHC class II genes of interest, including but not limited to, the human DR2, DR4, or DQ genes. See for example, WO2006/056769; Madsen et al., Nature Genetics supra; and Cheng et al, supra. The mice are then genotyped using techniques known in the art, such as PCR confirmation of insertion of the transgene sequence, to identify a subject having the double transgenic genome.

Using an alternative method, an embryo from a Tg animal expressing the human blood clotting factor may be further modified to express a second transgene encoding the human MHC class II genes. For example, an embryo is isolated from a pregnant Tg heterozygous or homozygous Tg-hu vWF, Tg-hu FVIII, Tg-Hu FVII or Tg-hu FIX mouse as described in the previous examples, and is subsequently transformed with an expression cassette encoding the human MHC class II genes, such as those described in WO2006/056769, Madsen et al., Nature Genetics supra; and Cheng et al, supra. The double transgenic embryos are then implanted into a pseudopregnant mice and double transgenic mice bred as described above. The mice are positively identified as double transgenic by genotyping using techniques known in the art, such as PCR confirmation of insertion of the transgene sequence.

Mice expressing both the human blood clotting factor genes and the human MHCII genes will be tolerant to the human blood clotting factor and also, in the event that the exogenous protein causes antigen-specific antibodies to arise, will present the antigen in the context of the human immune system. Using the human MHC genes allows for presentation of the natural antigenic epitope, and therefore the portion of an exogenously administered protein, such as a blood clotting factor, which is immunogenic in human patients is determined. Identifying antigenic epitopes assists in developing improved therapies for patients having blood clotting and coagulation disorders.

Example 5

Screening for Antibodies Against the Exogenously Administered Protein in Animals Tolerant to the Human Protein Humanized mice expressing the human Factor VIII, human vWF, human Factor IX or human Factor VII transgenes and, optionally, also expressing human MHC Class II, should be tolerant to the related human protein when that protein is administered exogenously. The humanized animals make it possible to screen for the spontaneous development of antibodies against the protein of interest, and to assay for development of anti-self antibodies after administration of exogenous protein or a variant thereof to the humanized animals.

In order to test for any endogenous anti-self antibody production, blood factor-specific antibody levels in the humanized mouse are measured by ELISA or radioimmunoassay using monoclonal antibodies specific for the blood clotting factor. For example, in the humanized vWF mouse, serum samples are obtained from animals expressing the human vWF protein and the baseline levels of anti-vWF specific antibodies are assayed by ELISA (See for example Soff et al., *J Lab Clin Med.* 121:424-30, 1993; and Mohri et al., *Blood* 91:3623-9, 1998). Briefly, serum samples from the subjects are added in increasing concentration to the wells of a 96-well polystyrene plate coated with vWF for 1 hour at 22° C. After washing with PBS, 0.05% Tween 20, horseradish peroxidase (HRP)-conjugated isotype-specific Igs is added to each well. Then a peroxidase substrate (o-phenylenediamine; Zymed) is added and the reaction was stopped with 2 mol/L $H_2SO_4$. The amount of antibody detected is then compared to a standard curve and the levels of anti-vWF antibody determined.

Animals are then administered purified human vWF or a fragment, analog or variant of the human vWF protein which could be used therapeutically, and anti-vWF serum levels assessed at specified time points. Serum samples are taken at different time points, including, but not limited to 4 hours, 12 hours, 24 hours, 48 hours and 72 hours after administration of therapeutic protein. When therapeutic protein is given over multiple doses or in subsequent weeks, serum samples are taken repeatedly upon re-administration of the therapeutic protein to the host animal to determine if there is delayed development of antigen-specific antibodies. The serum samples are assayed by ELISA as set out above.

The antigen-specific antibody assay set out above, or similar assay, may also be carried out using either the FVII or FVIII humanized animals. See for example Lindgren et al., *Haemophilia* 8:644-8, 2002 and Sahud et al., *Haemophilia* 13:317-22, 2007, which describe ELISA assays to detect anti-FVIII antibodies. Briefly, using protocols and techniques known in the art, purified FVIII is coated onto a substrate, usually a polystyrene plate, after washing and blocking steps, serum samples putatively containing anti-FVIII antibodies is then incubated with the FVIII-coated plate. The plate is washed to remove excess antibody and serum and bound antibody is detected using well-known detection methods, e.g., anti-isotype antibody conjugated to a detection enzyme (e.g, Alkaline phosphatase or horseradish peroxidase) detected using the cognate detection reagent.

Similar assays are useful to detect antibodies to FVII. Human FVII is coated to a 96 well plate using standard ELISA protocols. Serum isolated from humanized FVII animals is applied to the FVII-coated wells. FVII-specific antibodies are then detected as described above.

Example 6

Expression of FVII and FVIII RNA in Transgenic Animals

To determine the gene expression pattern of human factor VII (huFVII) in huFVII transgenic mice, quantitative Polymerase Chain Reaction (QPCR) was used: nine organs were analyzed for transgene expression: liver, lymph nodes, lung, spleen, kidneys, heart, bone marrow, muscle of upper thigh, and brain.

Organs were harvested and placed immediately into RNA stabilizing reagent (RNAlater, Qiagen, Germantown, Md.) for storage and transport. RNA of the organs was isolated following the protocol of the RNeasy Mini Kit (Qiagen, Cat. no. 74104). The concentration of the isolated RNA was determined and diluted accordingly. Residual amounts of contaminating genomic DNA were removed from the RNA preparation using gDNA Wipeout Buffer (part of the QuantiTect Reverse Transcription Kit, Qiagen) Reverse Transcription cDNA was synthesized from RNA samples according to the protocol of the QuantiTect Reverse Transcription Kit.

The quantification of huFVII gene expression (4 male huFVII transgenic mice the organ panel was conducted using the following setup.

```
Primers:
                                       (SEQ ID NO: 11)
huFVII MS2 for 5' GAA TGG AGC TCA GTT GTG 3';

(SEQ ID NO: 12)
huFVII MS2 rev 5' ATC AGG TTC CTC CAG TTC 3'.
```

The PCR was set up using the PerfeCTa SYBR Green PCR MasterMix, Quanta Biosciences (Gaithersburg, Md.), and Applied Biosystems 7500 Fast Real-Time PCR System and 7000 Real-Time PCR system (Foster City, Calif.) using the following parameters: Activation, 95° C. 10 min: 40 cycles of DNA denaturation, 95° C. 15 sec; Annealing/Elongation: 58° C. 1 min.

Results shown in Table 2 (ranked by Ct values (n.d.=not detectable) indicate that the highest expression of human FVII RNA is found in the liver of all animals investigated.

TABLE 2

| Rank | Mouse 1 Organ | Ct | Mouse 2 Organ | Ct | Mouse 3 Organ | Ct | Mouse 4 Organ | Ct |
|---|---|---|---|---|---|---|---|---|
| 1 | liver | 20.33 | liver | 20.12 | liver | 25.15 | liver | 23.07 |
| 2 | lymph nodes | 27.08 | lung | 27.12 | lymph nodes | 30.84 | lung | 30.23 |
| 3 | lung | 27.40 | spleen | 27.66 | spleen | 31.20 | spleen | 31.12 |
| 4 | spleen | 28.89 | lymph node | 28.41 | lung | 31.41 | lymph nodes | 31.20 |
| 5 | kidneys | 29.81 | kidneys | 29.80 | bone marrow | 32.29 | kidneys | 32.93 |
| 6 | brain | 30.92 | heart | 34.70 | kidneys | 33.58 | heart | 34.82 |
| 7 | heart | 34.11 | thigh | 37.77 | heart | 34.77 | muscle | 35.88 |
| 8 | muscle | 34.76 | brain | 37.91 | muscle | 36.34 | bone marrow | 36.47 |
| 9 | | | | | brain | 38.34 | brain | n.d. |

To determine the gene expression pattern of human factor VIII (huFVIII) in human factor VIII transgenic mice, quantitative polymerase chain reaction (QPCR) was used. Three different sublines of huFVIII mice were investigated and studied the expression of huFVIII in the following eight organs: liver, lymph nodes, lung, spleen, kidneys, heart, muscle of upper thigh, and neonatal thymus.

Organs were harvested and placed immediately into RNA stabilizing reagent for storage and transport and the RNA prepared as described above.

The quantification of huFVIII gene expression in the organ panel was conducted as described below.

To confirm absence of contaminating gDNA and to check the integrity of cDNA and endogenous control was used [Mouse ACTB (actin, beta), VIC/MGB Probe, (Applied Biosystems Cat. no. 4352341E)].

The Human FVIII RNA was amplified using the following probe and primers:

```
Probe: huFVIII-FAM:
                                  (SEQ ID NO: 13)
CCAAAGCTGGAATTTGGCGGGTG-BHQ
(comprising the fluorophore/quencher pair FAM/
Black Hole Quencher (BHQ ®) dye);

Primer forward huFVIII:
                                  (SEQ ID NO: 14)
GGCACTGTACAATCTCTATCCAGGT;

Primer reverse huFVIII:
                                  (SEQ ID NO: 15)
GATGCTCGCCAATAAGGCAT
```

PCR was carried out using the Taqman Universal PCR Master Mix, (Applied Biosystems) on an Applied Biosystems: 7500 Fast Real-Time PCR System and Applied Biosystems: 7000 Real-Time PCR system with the following parameters: Activation, 95° C. 10 min, 40 cycles; DNA denaturation, 95° C. 15 sec.; Annealing/Elongation: 60° C. 1 min.

Results indicate that the highest expression of huFVIII RNA is found in the liver of sublines E and I. The Ct-values from 2 females and 2 males of each of the 3 sublines are shown in Tables 3-8.

Table 3 shows the expression of huFVIII in liver, kidney, heart, lung, lymph nodes, muscle, spleen of 2 female mice and 2 male mice of huFVIII transgenic mice, subline E (n.d.=not detectable).

TABLE 3

| Rank | Female Mouse 1 Organ | Ct | Female Mouse 2 Organ | Ct | Male Mouse 1 Organ | Ct | Male Mouse 2 Organ | Ct |
|---|---|---|---|---|---|---|---|---|
| 1 | liver | 32.95 | liver | 34.05 | liver | 31.87 | liver | 32.84 |
| 2 | kidney | 37.36 | kidney | 36.12 | lung | n.d. | kidney | 39.75 |
| 3 | lung | 39.41 | lymph nodes | 37.53 | kidney | n.d. | muscle | n.d. |
| 4 | lymph nodes | 39.45 | muscle | 38.58 | heart | n.d. | spleen | n.d. |
| 5 | muscle | 39.77 | heart | 38.78 | spleen | n.d. | lymph nodes | n.d. |
| 6 | spleen | 39.86 | spleen | 38.78 | lymph nodes | n.d. | heart | n.d. |
| 7 | heart | n.d. | lung | n.d. | muscle | n.d. | lung | n.d. |

Table 4 shows the expression of huFVIII in neonatal thymus of 2 female and 2 male mice of huFVIII transgenic mice, subline E.

TABLE 4

| Rank | Female Mouse 1 Organ | Ct | Female Mouse 2 Organ | Ct | Male Mouse 1 Organ | Ct | Male Mouse 2 Organ | Ct |
|---|---|---|---|---|---|---|---|---|
| 1 | Neonatal thymus | 33.66 | Neonatal thymus | 33.50 | Neonatal thymus | 33.66 | Neonatal thymus | 32.67 |

Table 5 shows the expression of huFVIII in liver, kidney, lung, lymph nodes, muscle and spleen of 2 female mice and two male mice of huFVIII transgenic mice, subline G (n.d.=not detectable).

TABLE 5

| Rank | Female Mouse 1 Organ | Ct | Female Mouse 2 Organ | Ct | Male Mouse 1 Organ | Ct | Male Mouse 2 Organ | Ct |
|---|---|---|---|---|---|---|---|---|
| 1 | liver | 39.24 | liver | 37.93 | muscle | 37.64 | liver | 35.33 |
| 2 | lymph nodes | n.d. | lymph nodes | n.d. | liver | 39.34 | lymph nodes | n.d. |
| 3 | lung | n.d. | lung | n.d. | lymph nodes | n.d. | lung | n.d. |
| 4 | spleen | n.d. | spleen | n.d. | lung | n.d. | spleen | n.d. |
| 5 | heart | n.d. | heart | n.d. | spleen | n.d. | heart | n.d. |
| 6 | kidney | n.d. | kidney | n.d. | heart | n.d. | kidney | n.d. |
| 7 | muscle | n.d. | muscle | n.d. | kidney | n.d. | muscle | n.d. |

Table 6 shows the expression of huFVIII in neonatal thymus of 2 female mice and 2 male mice of huFVIII transgenic mice, subline G.

TABLE 6

| Rank | Female Mouse 1 Organ | Ct | Female Mouse 2 Organ | Ct | Male Mouse 1 Organ | Ct | Male Mouse 2 Organ | Ct |
|---|---|---|---|---|---|---|---|---|
| 1 | Neonatal thymus | 30.66 | Neonatal thymus | 35.09 | Neonatal thymus | 30.40 | Neonatal thymus | 31.72 |

Table 7 shows the expression of huFVIII in liver, kidney, lung, lymph nodes, muscle and spleen of 2 female mice and two male mice of huFVIII transgenic mice, subline I (n.d.=not detectable).

TABLE 7

| Rank | Female Mouse 1 | | Female Mouse 2 | | Male Mouse 1 | | Male Mouse 2 | |
|---|---|---|---|---|---|---|---|---|
| | Organ | Ct | Organ | Ct | Organ | Ct | Organ | Ct |
| 1 | liver | 35.51 | liver | 30.94 | liver | 32.06 | liver | 30.51 |
| 2 | lung | n.d. | muscle | 38.79 | lymph nodes | n.d. | lung | n.d. |
| 3 | spleen | n.d. | lung | n.d. | lung | n.d. | spleen | n.d. |
| 4 | heart | n.d. | spleen | n.d. | spleen | n.d. | lymph nodes | n.d. |
| 5 | lymph nodes | n.d. | heart | n.d. | heart | n.d. | heart | n.d. |
| 6 | kidney | n.d. | kidney | n.d. | muscle | n.d. | kidney | n.d. |
| 7 | muscle | n.d. | lymph nodes | n.d. | kidney | n.d. | muscle | n.d. |

Table 8 shows the expression of huFVIII in neonatal thymus of 2 female mice and 2 male mice of huFVIII transgenic mice, subline I.

TABLE 8

| Rank | Female Mouse 1 | | Female Mouse 2 | | Male Mouse 1 | | Male Mouse 2 | |
|---|---|---|---|---|---|---|---|---|
| | Organ | Ct | Organ | Ct | Organ | Ct | Organ | Ct |
| 1 | Neo-natal thymus | 37.95 | Neo-natal thymus | 36.31 | Neo-natal thymus | 35.24 | Neo-natal thymus | 36.36 |

The RNA analysis demonstrates that the transgene is expressed in the liver and neonatal thymus of all three transgenic mouse sublines generated. These organs are highly relevant during generation of the animal immune system, and expression in the neonatal thymus often can lead to tolerance to the protein expressed in the thymus during immune system development.

Example 7

Transgenic Mice are Tolerant to Exogenous Native Human FVIII or FVIIa

To determine whether the transgenic mice expressing human blood factors are tolerant to subsequent administration of the human native protein, hemophilic mice (FVIII knockout) were crossed with the mice expressing human FVIII as described above (sublines E, G and I). Mice were administered human FVIII and subsequent anti-FVIII antibody responses measured.

Three sublines of transgenic mice (sublines E, G and I) were administered i.v. doses of huFVIII at weekly intervals, 200 ng huFVIII (ADVATE®, Baxter Healthcare SA, Vienna, Austria) per dose in 200 µL volume. Serum samples were taken after 4 or 8 weekly doses and anti-FVIII antibody titer measured using a standard ELISA protocol.

Figure 5A:
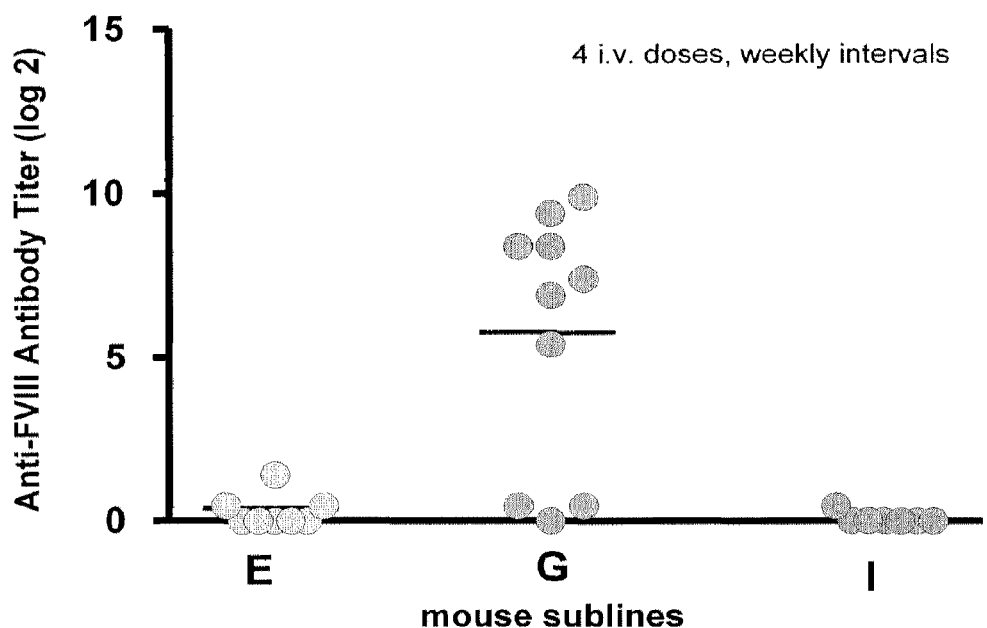
FIGS. 5A and 5B show the anti-FVIII antibody production in different sublines of mice transgenic for human FVIII. Mice in subline G generated anti-FVIII antibodies when given either 4 (FIG. 5A) or 8 weekly doses (FIG. 5B). Mice in sublines E and I generated no anti-FVIII antibodies in either dose regimen.
Figure 5B:
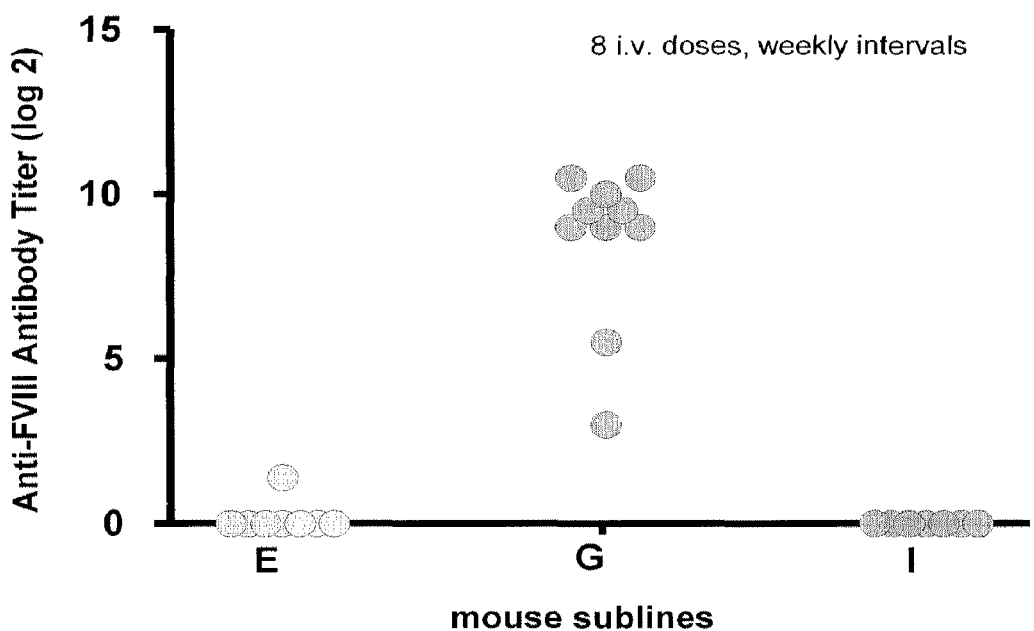

Results demonstrated that mice in subline G generated anti-FVIII antibodies when given either 4 or 8 weekly doses (FIGS. 5A and 5B). Mice in sublines E and I generated no anti-FVIII antibodies in either dose regimen. These studies show that 2 of the 3 transgenic sublines are tolerant to human FVIII. Additionally, antibody titers of specific IgG subclasses and IgA were analyzed.

Figure 6:
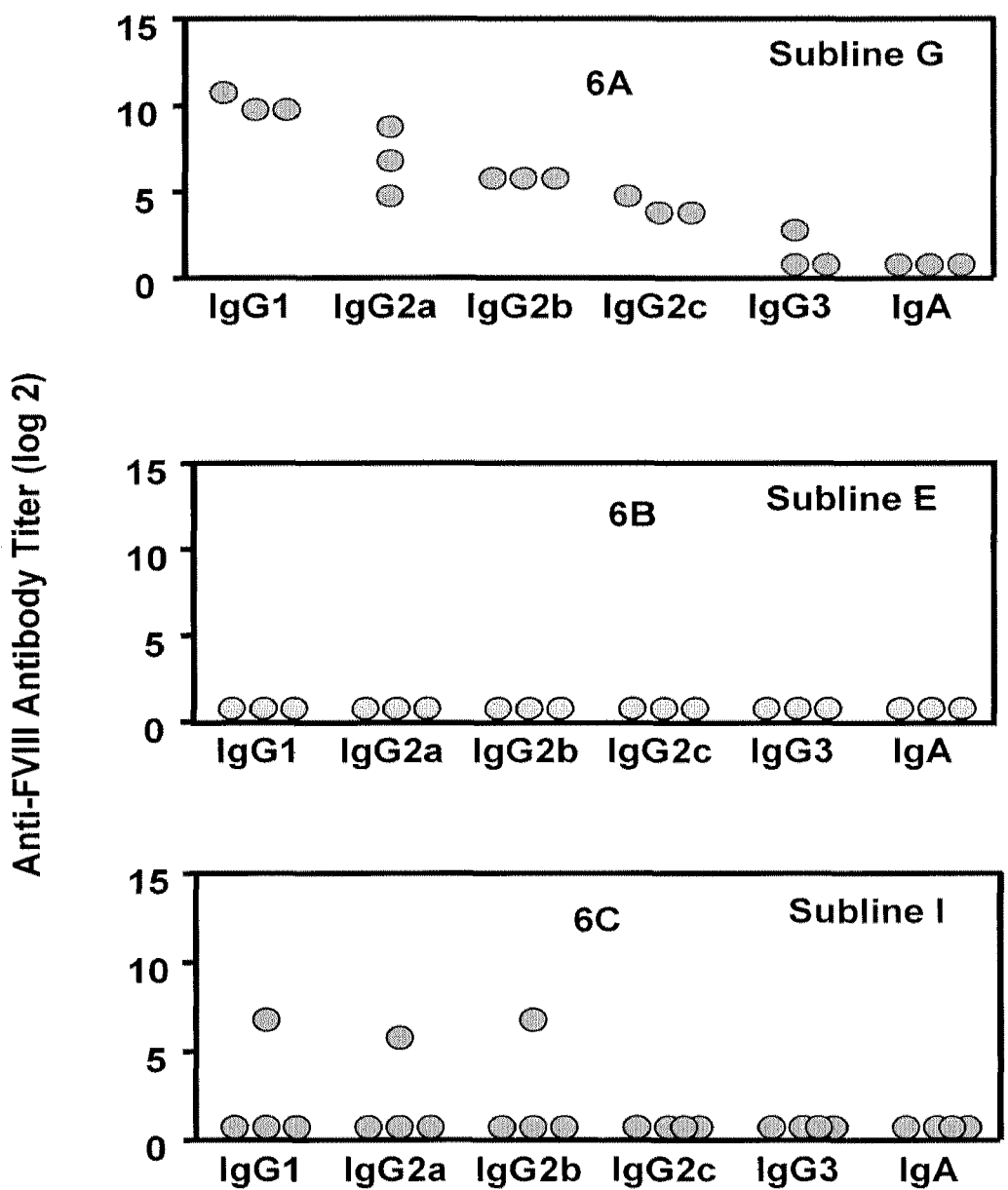
FIG. 6 shows the anti-FVIII antibody production of different IgG subclasses and of IgA in different sublines of mice transgenic for human FVIII. Mice in subline G generated anti-FVIII antibodies of IgG subclasses IgG1, IgG2a, IgG2b, IgG2c when given 8 weekly doses (FIG. 6A). Mice in sublines E did not generate anti-FVIII antibodies of any IgG subclass (FIG. 6B). 1 out of 4 mice of subline I generated anti-FVIII antibodies of IgG subclasses IgG1, IgG2a, IgG2b (FIG. 6C).

Results demonstrated that mice of subline G generated anti-FVIII antibodies of IgG subclasses IgG1, IgG2a, IgG2b and IgG2c but no IgA antibodies when given 8 weekly doses of FVIII (FIGS. 6A, 6B and 6C). Mice of subline E did not generate any anti-FVIII antibodies when given 8 weekly doses of FVIII. 1 out of 4 mice of subline I generated anti-FVIII antibodies of IgG subclasses IgG1, IgG2a and IgG2b when given 8 weekly doses of FVIII. These results demonstrate that mice of subline E are completely tolerant to human FVIII, mice of subline I are partly tolerant, and mice of subline G are not tolerant to human FVIII.

In order to determine if transgenic mice expressing human FVIIa are tolerant to exogenous protein, FVIIa transgenic mice were assessed for anti-FVIIa antibodies upon administration of exogenous FVIIa (Baxter Healthcare SA, Vienna, Austria).

Figure 8:
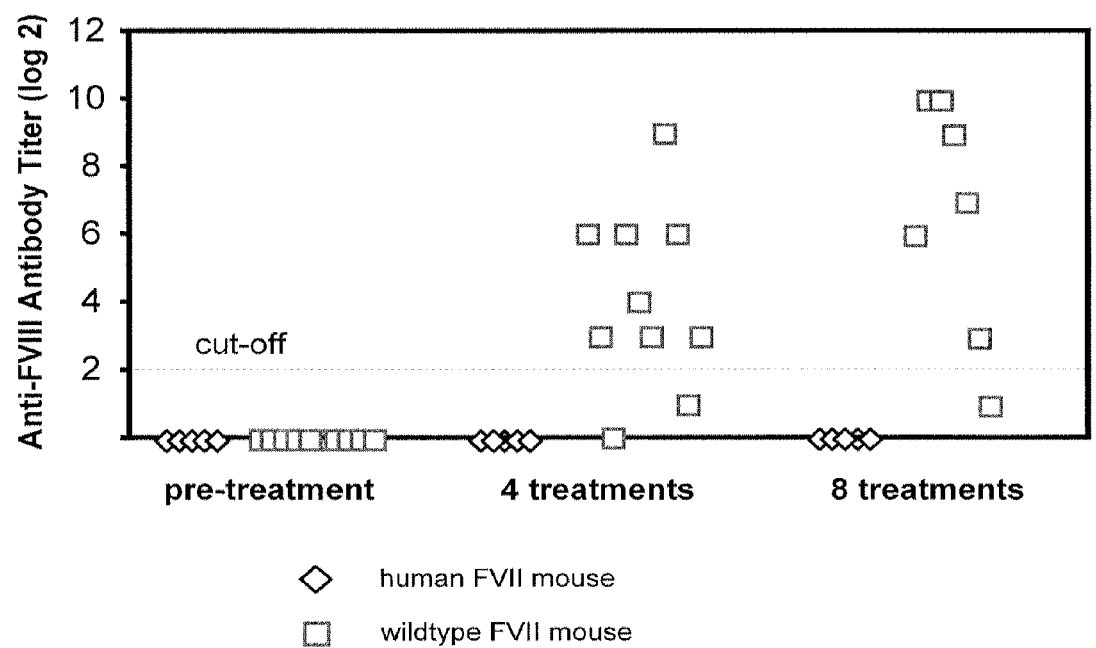
FIG. 8 illustrates the antibody production in transgenic mice expressing human FVII and in control mice after receiving exogenous human FVII.

Ten control wildtype mice and 5 FVIIa transgenic mice were administered i.v. doses of huFVIIa at weekly intervals, 10 µg huFVIIa per dose in 200 µL volume. Serum samples were taken after 4 or 8 weekly doses and anti-FVIIa antibody titer measured using a standard ELISA protocol. FIG. 8 shows that mice expressing human FVII do not produce anti-FVII antibodies in response to exogenous human FVII whereas control mice produce high titers of anti-FVII antibodies.

The above experiments demonstrate that one subline (subline E) of transgenic animals expressing human blood clotting factor VIII and the line of mice that expresses human blood clotting factor VII are tolerant to exogenous administration of native human blood clotting factors VIII or VII, respectively. These transgenic animals provide a useful animal model to study in vivo responses to administration of human blood factors and the development of inhibitors to therapeutic blood clotting factors which commonly arise in human patients receiving replacement therapy, and can arise spontaneously in acquired blood factor disorders such as acquired hemophilia A.

Example 8

Breaking of Tolerance in Transgenic Animals by Blood Clotting Factors that Carry Neoantigens In order to show that immune tolerance to human blood clotting factors in transgenic animals that express human blood clotting factors can be broken, animals of subline E (immune tolerant to native human FVIII) were treated with a model substance that comprises a human FVIII that carries neoantigens. Neoantigens were generated by chemical modification of the native human FVIII. Animals were treated with native human FVIII or with the human FVIII that carries neoantigens.

Mice were treated with 4 weekly doses of 200 ng FVIII. (ADVATE, Baxter Healthcare SA, Vienna, Austria) or 200 ng FVIII carrying neoantigens (generated by Baxter Healthcare SA, Vienna, Austria) in 200 µL. Serum samples were taken after the last dose and anti-FVIII antibody titers were measured using a standard ELISA protocol.

Figure 7:
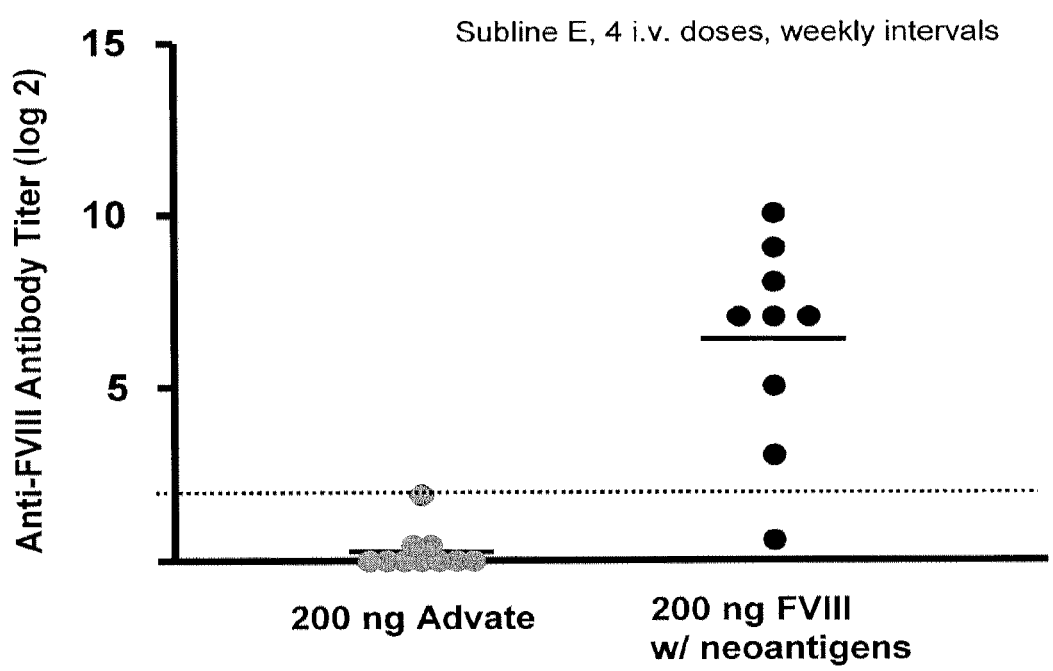
FIG. 7 illustrates the anti-FVIII antibody production in mice that express the human FVIII transgene (subline E) after application of 4 weekly doses of either native FVIII or FVIII that carries neoantigens.

Results shown in FIG. 7 demonstrate that mice treated with ADVATE® did not develop anti-FVIII antibodies. However, 8 out of 9 mice that were treated with the FVIII comprising neoantigens did develop anti-FVIII antigens. These results demonstrate that these transgenic animals provide a useful model to recognize neoantigen formation in human blood clotting factors.

Example 9

Study of Blood Factor Tolerance in Transgenic Animals Expressing Blood Clotting Factors The development of inhibitors to therapeutic blood factors, or spontaneous development of anti-blood factor antibodies are significant blockades to effective treatment of bleeding disorders. For example, hemophilic patients receiving FVIII therapy may develop antibodies to the therapeutic protein which render the treatment ineffectual (Reding Mont., Haemophilia 12(suppl 6):30-36, 2006). Additionally, acquired hemophilia A (AHA) develops when an individual spontaneously generates antibodies against FVIII. There is no definitive etiology of acquired hemophilia to date, but incidents of AHA is higher in individuals having an autoimmune disease, those having certain types of cancer, and has been shown to result from an allergic reaction to drug treatment, such as penicillin, fludarabine, or interferon-alpha (Franchini et al., Med Sci Monit 13:RA55-61, 2007).

While animal models of hemophilia have been used to study the development of FVIII inhibitors in hemophilic patients (Reipert et al., Brit J Heamatol 136:12-25, 2006), no adequate animal model exists to study the breaking of tolerance in acquired hemophilia A or other types of breaking of tolerance in hemophilic patients. The transgenic animals expressing human blood factors described herein are useful models to study acquired hemophilia A and other spontaneous autoimmunity or spontaneous inhibitor development against blood clotting factors.

In one embodiment, transgenic animals expressing human FVIII are treated with drugs known to cause AHA, such as penicillin, fludarabine or interferon-alpha, and the animals are assessed for development of anti-FVIII antibodies. In another embodiment, transgenic animals are administered proinflammatory cytokines, ligands for toll-like receptors or any other compound that induces the release of proinflammatory cytokines in vivo to break tolerance to FVIII. To determine the extent of inhibitor induction, blood clotting factor inhibitors are measured using techniques well-known in the art. For example the Bethesda Unit (BU) scale is used to assess the extent of FVIII inhibitors (Franchini M., Haematology 11:119-25, 2006). ELISA methods as described herein are also used to measure anti-blood factor antibodies. The levels of cytokines and immune-related molecules are also determined before and after treatment to examine the reaction of the immune system to induction of autoantibodies and other inhibitors.

The transgenic animals are also useful to study effective treatment of AHA, other spontaneous autoimmunity to blood clotting factors, or other inhibitors of blood clotting factors that arise after repeated administration of therapeutic blood clotting factor. Transgenic mice that have developed blood factor inhibitors are treated with agents that inhibit the humoral immune response and acquired immune response, for example, steroids, cyclosporine, gamma-globulin, and biologics such as rituximab (see e.g., Collins, P W. Haemophilia 12(Suppl 6):94-101, 2006; Alvarado et al., Clin Appl Thrombosis/Hemostasis 13:443-48, 2007) are administered, and the levels of autoantibodies and other inhibitors are assessed.

Inhibitors are also known to develop in patients receiving FIX treatment for hemophilia B (DiMichele D., Brit J Haematol 138:305-15, 2007). Mice transgenic for FIX are useful in the study of the development of inhibitors in hemophilia B patients using similar regimens as described above for FVIII and hemophilia A.

The transgenic animals described herein enable the discovery of antigen-specific antibodies which arise in response to therapeutic human proteins and provides a valuable tool for predicting which therapies could be harmful to patients and those that may be most beneficial.

Numerous modifications and variations in the invention as set forth in the above illustrative examples are expected to occur to those skilled in the art. Consequently only such limitations as appear in the appended claims should be placed on the invention.

What is claimed:

1. A transgenic mouse having a genome comprising a human transgene polynucleotide sequence encoding a human Factor VIII blood clotting factor, wherein the polynucleotide sequence is operably linked to a promoter polynucleotide sequence, wherein the mouse does not express all or part of a polynucleotide encoding an endogenous mouse Factor VIII, wherein the mouse also comprises in its genome a human major histocompatibility class II gene in place of a major histocompatibility class II gene endogenous to the transgenic mouse, and wherein the mouse is tolerant to administration of the exogenous human Factor VIII.

2. The transgenic mouse of claim 1, wherein the polynucleotide sequence comprises a poly A polynucleotide sequence.

3. A transgenic mouse comprising a transgene polynucleotide sequence encoding a human Factor VIII blood clotting factor, said human Factor VIII having physiological activity of the human Factor VIII, said transgenic mouse having in its genome an exogenous transgene construct comprising:
    (a) transcriptional regulatory polynucleotide sequences,
    (b) DNA encoding said human Factor VIII, and
    (c) a polyadenylation signal,
wherein (A), (B) and (C) are operably linked in said exogenous gene construct to obtain production of said human Factor VIII in said transgenic mouse, wherein the mouse does not express all or part of a polynucleotide encoding an endogenous mouse factor VIII, and wherein the genome of the transgenic mouse also comprises a polynucleotide encoding a human major histocompatibility class II gene in place of the a major histocompatibility class II gene endogenous to the transgenic mouse, and wherein the mouse is tolerant to administration of the exogenous human Factor VIII.

4. The transgenic mouse of claim 3, wherein the transcriptional regulatory polynucleotide sequences are selected from the group consisting of 5' transcriptional regulatory polynucleotide sequences, 3' transcriptional regulatory polynucleotide sequences, internal transcriptional regulatory polynucleotide sequences, and combinations thereof.

5. A method of producing a transgenic mouse comprising a polynucleotide transgene encoding a human Factor VIII blood clotting factor comprising:
    a) introducing a polynucleotide sequence encoding said human Factor VIII into the genome of a mouse lacking the endogenous mouse Factor VIII gene to provide a transgenic mouse whose genome comprises a polynucleotide encoding human Factor VIII and does not comprise in its genome the endogenous mouse Factor VIII gene; and
    b) introducing a polynucleotide sequence encoding an human major histocompatibility class II gene into the genome of the mouse resulting from step (a) to replace all or part of a major histocompatibility class II gene endogenous to the mouse.

6. The transgenic mouse of claim 1, wherein the mouse is homozygous for said human Factor VIII transgene.

7. The transgenic mouse of claim 1, wherein the mouse is heterozygous for said human Factor VIII transgene.

8. A method for producing a transgenic mouse comprising a polynucleotide encoding a human Factor VIII blood clotting factor comprising:
    a) providing a polynucleotide sequence encoding a human Factor VIII blood clotting factor and a positive selectable marker gene, said marker gene flanked by loxP sites;

b) introducing said polynucleotide sequence into an embryonic stem cell from the same animal species as said mouse under conditions such that said polynucleotide sequence is homologously recombined into a genomic locus of said embryonic stem cell to produce an embryonic stem cell containing a polynucleotide encoding a human Factor VIII and said selectable marker gene;

c) injecting said homologously recombined embryonic stem cell into a blastocyst of said mouse;

d) introducing said injected blastocyst into a pseudo-pregnant female mouse; and e) permitting said pseudo-pregnant female mouse to deliver one or more transgenic mice containing said homologously recombined DNA sequence, wherein said one or more transgenic mice express said human Factor VIII, wherein the method further comprises introducing a polynucleotide sequence encoding a human major histocompatibility class II gene into the genomic DNA of the mouse, said polynucleotide sequence encoding a human major histocompatibility class II gene replacing all or part of a major histocompatibility class II gene endogenous to the transgenic mouse such that the transgenic mouse does not express its endogenous major histocompatibility class II gene.

9. An experimental mouse model that is a transgenic mouse comprising a transgene encoding human Factor VIII in its genome, wherein the mouse does not generate a significant antibody titer against human Factor VIII when human Factor VIII is administered, wherein the mouse does not express all or part of a polynucleotide encoding an endogenous mouse Factor VIII gene, wherein the genome of the transgenic mouse also comprises a polynucleotide encoding a human major histocompatibility class II gene in place of the major histocompatibility class II gene endogenous to the transgenic mouse.

10. The mouse model of claim 9, which is an experimental animal model for acquired hemophilia A or hemophilia B.

11. The transgenic mouse of claim 1, wherein the promoter is selected from the group consisting of a liver-specific promoter, a muscle-specific promoter, a pancreatic-specific promoter, a neural-specific promoter, an endothelial cell-specific promoter, a smooth muscle-cell specific promoter, a tyrosinase-specific promoter, a blood clotting factor promoter, an adipose tissue promoter and an inducible promoter.

* * * * *